United States Patent
Arai et al.

(10) Patent No.: US 10,733,426 B2
(45) Date of Patent: Aug. 4, 2020

(54) DRIVER STATE DETERMINATION DEVICE AND DRIVER STATE DETERMINATION METHOD

(71) Applicants: DAIKIN INDUSTRIES, LTD., Osaka-shi, Osaka (JP); TOKYO INSTITUTE OF TECHNOLOGY, Meguro-ku, Tokyo (JP)

(72) Inventors: Junichiro Arai, Osaka (JP); Takashi Gotou, Osaka (JP); Makoto Iwakame, Osaka (JP); Kenichi Hino, Osaka (JP); Tomoya Hirano, Osaka (JP); Yasunori Kotani, Tokyo (JP); Yoshimi Ohgami, Tokyo (JP); Taro Tomatsu, Tokyo (JP)

(73) Assignees: Daikin Industries, Ltd., Osaka (JP); Tokyo Institute of Technology, Tokyo (JP)

( * ) Notice: Subject to any disclaimer, the term of this patent is extended or adjusted under 35 U.S.C. 154(b) by 106 days.

(21) Appl. No.: 15/767,965

(22) PCT Filed: Oct. 17, 2016

(86) PCT No.: PCT/JP2016/080754
§ 371 (c)(1),
(2) Date: Apr. 12, 2018

(87) PCT Pub. No.: WO2017/065315
PCT Pub. Date: Apr. 20, 2017

(65) Prior Publication Data
US 2018/0307902 A1    Oct. 25, 2018

(30) Foreign Application Priority Data

Oct. 15, 2015  (JP) ................. 2015-203355
Feb. 29, 2016  (JP) ................. 2016-038480
Feb. 29, 2016  (JP) ................. 2016-038482

(51) Int. Cl.
*G06K 9/00* (2006.01)
*A61B 5/01* (2006.01)
(Continued)

(52) U.S. Cl.
CPC ............ *G06K 9/00308* (2013.01); *A61B 5/00* (2013.01); *A61B 5/01* (2013.01); *A61B 5/024* (2013.01);
(Continued)

(58) Field of Classification Search
CPC .......... G06K 9/00308; G06K 9/00268; B60W 30/00; B60W 2600/00; B60Q 9/00;
(Continued)

(56) References Cited

U.S. PATENT DOCUMENTS 6,092,058 A     7/2000  Smyth
8,069,125 B2 *  11/2011 Jung ................. A61B 5/04842
                                        706/11
(Continued)

FOREIGN PATENT DOCUMENTS

JP    2008-220602 A    9/2008
JP    2013-176406 A    9/2013
JP    2014-100227 A    6/2014

OTHER PUBLICATIONS

N Dahal et al.; TVAR modeling of EEG to detect audio distraction during simulated driving; Journal of Neural Engineering; May 8, 2014; 2014 IOP Publishing Ltd.
(Continued)

*Primary Examiner* — Amir Alavi
(74) *Attorney, Agent, or Firm* — Global IP Counselors, LLP

(57) ABSTRACT

A driver state determination device includes a facial change information acquisition unit acquiring facial change information indicating a time-series change in facial data of a
(Continued)

subject, and a driver state determination unit determining the driver state of the subject based on the facial change information. The subject is selected from the group consisting of a subject driving a machine from when brain function activation information that activates human brain function is provided, a subject driving a machine from when the brain function activation information provided to the subject driving the machine is detected, and a subject performing a predetermined operation on a machine.

24 Claims, 43 Drawing Sheets

(51) Int. Cl.
    *A61B 5/00*     (2006.01)
    *A61B 5/024*     (2006.01)
    *A61B 5/16*     (2006.01)

(52) U.S. Cl.
    CPC ............ *A61B 5/165* (2013.01); *A61B 5/4064* (2013.01); *G06K 9/00268* (2013.01); *A61B 2560/0242* (2013.01)

(58) Field of Classification Search
    CPC ..... B62D 15/025; A61B 5/4064; A61B 5/024; A61B 5/743; A61B 5/165; A61B 5/16; A61B 5/01; A61B 5/0064
    See application file for complete search history.

(56) References Cited

U.S. PATENT DOCUMENTS

| | | | | |
|---|---|---|---|---|
| 8,892,274 | B2* | 11/2014 | Baudry | B64C 19/00 340/945 |
| 8,989,854 | B2* | 3/2015 | Sundstrom | G06F 3/015 600/545 |
| 9,509,818 | B2* | 11/2016 | Li | H04L 51/22 |
| 9,789,869 | B2* | 10/2017 | Fujita | B60W 30/00 |
| 10,242,713 | B2* | 3/2019 | Rothschild | G11B 27/10 |
| 10,474,914 | B2* | 11/2019 | Banno | G06T 7/593 |
| 2018/0307902 | A1* | 10/2018 | Arai | A61B 5/024 |
| 2019/0069832 | A1* | 3/2019 | Arai | A61B 5/165 |

OTHER PUBLICATIONS

European Search Report of corresponding EP Application No. 16 855 566.2 dated Jul. 12, 2019.
International Preliminary Report of corresponding PCT Application No. PCT/JP2016/080754 dated Apr. 26, 2018.
International Search Report of corresponding PCT Application No. PCT/JP2016/080754 dated Jan. 10, 2017.

* cited by examiner

| SUBJECT | BRAIN FUNCTION ACTIVATION INFORMATION / PREDETERMINED OPERATION | INTERPRETATION OF CORRELATION COEFFICIENT r | USE/PURPOSE |
|---|---|---|---|
| AUTOMOBILE DRIVER (INCLUDING AUTOMATIC DRIVING) | DRIVING OPERATION, EXTERNAL REGRESSOR (e.g. DISPLAY OF RED TRAFFIC LIGHT) | HIGHER CORRESLATION COEFFICIENTS ARE BETTER | PREVENTION OF CARELESS DRIVING AND DROWSY DRIVING |
| AUTOMATIC MACHINE OPERATOR (OBSERVER) | SIGNALS FROM AUTOMATICALLY MOVING MACHINE | HIGHER CORRESLATION COEFFICIENTS ARE BETTER | PREVENTION OF CARELESSNESS MONITORING AND DROWSY MONITORING |
| TRAIN DRIVER | RAILWAY SIGNS, STOPPING TARGETS | HIGHER CORRESLATION COEFFICIENTS ARE BETTER | PREVENTION OF CARELESS DRIVING, DROWSY DRIVING, AND MISSING OF SIGNS |
| AIRCRAFT PILOT | SIGNALS FROM INSTRUMENTS, COMMANDS FROM CONTROL TOWER | HIGHER CORRESLATION COEFFICIENTS ARE BETTER | PREVENTION OF MISOPERATION, PREVENTION OF OVERLOOKING OF INSTRUCTIOSN |
| DRIVER WITH INTENT TO PERFORM ACT OF TERROR | SIGNALS INDICATING INTENT TO CAUSE HARM (NEGATIVE REGRESSOR) | DANGER EXISTS WHEN CORRELATION VALUE TO NEGATIVE REGRESSOR IS HIGH | PREVENTION OF ACTS OF TERROR |
| INEXPERIENCED DRIVER | DRIVING OPERATION, EXTERNAL REGRESSOR (e.g. DISPLAY OF RED TRAFFIC LIGHT) | APPROPRIATE CORRELATION VALUE LEVEL IS PREFERRABLE | EVALUATION OF DRIVING SKILL |

FIG. 40

DRIVER STATE DETERMINATION DEVICE AND DRIVER STATE DETERMINATION METHOD

CROSS-REFERENCE TO RELATED APPLICATIONS

This U.S. National stage application claims priority under 35 U.S.C. § 119(a) to Japanese Patent Application Nos. 2015-203355, filed in Japan on Oct. 15, 2015, 2016-038480, filed in Japan on Feb. 29, 2016, and 2016-038482, filed in Japan on Feb. 29, 2016, the entire contents of which are hereby incorporated herein by reference.

TECHNICAL FIELD

The present invention relates to a driver state determination device and a driver state determination method.

BACKGROUND ART

In the prior art, there are studies on technology for monitoring driver states of subjects driving machines. For example, Japanese Unexamined Patent Application Publication No. 2014-100227 and similar documents disclose devices for determining concentration levels of subjects driving automobiles.

SUMMARY

Technical Problems

However, preparation work is complicated when taking electroencephalograms. For example, the electrodes must be pretreated before being applied to the subject. The tremendous cost involved in taking electroencephalograms is also a problem. Consequently, it is difficult to appropriately monitor the driver state of a subject driving a machine.

An object of the present invention is to provide a driver state determination device and a driver state determination method that enable an easy determination of the driver state of a subject driving a machine.

Solutions to Problems

A driver state determination device according to a first aspect of the present invention includes a facial change information acquisition unit, a facial change information decomposition unit, and a driver state determination unit. The facial change information acquisition unit acquires facial change information indicating time-series changes in facial data of a subject. The facial change information decomposition unit decomposes the facial change information into a plurality of components by singular value decomposition, principal component analysis, or independent component analysis. The driver state determination unit determines the driver state of the subject on the basis of a determination component extracted from the plurality of components.

In this specification, the term "driver state" represents the mental state and the physical state of the subject driving the machine. The mental state is represented by indicators corresponding to mental fatigue, mental stress, a state of carelessness, a state of concentration, and so on. The physical state is represented by indicators corresponding to physical fatigue, physical stress, and so on.

With the driver state determination device according to the first aspect, the plurality of components is obtained by subjecting the facial change information to singular value decomposition, principal component analysis, or independent component analysis, and the determination component is extracted from the plurality of components. As such, the presence/absence of brain activity of the subject can be easily estimated without using electrodes or the like that require pretreatment before being applied. As a result, the driver state of the subject driving the machine can be easily determined on the basis of the determination component corresponding to the brain function of the subject.

A driver state determination device according to a second aspect of the present invention is the driver state determination device of the first aspect, further including a brain function activation information provision unit and a determination component extraction unit. The brain function activation information provision unit provides brain function activation information, which activates human brain function, to the subject driving the machine. The determination component extraction unit extracts, from the plurality of components, a component related to the brain function activation information as the determination component.

With the driver state determination device according to the second aspect, the plurality of components is obtained by subjecting the facial change information to singular value decomposition, principal component analysis, or independent component analysis, and the determination component related to the provided brain function activation information is extracted from the plurality of components. As such, the presence/absence of brain activity of the subject can be easily estimated without using electrodes or the like that require pretreatment before being applied. As a result, the driver state of the subject driving the machine can be easily determined on the basis of the determination component corresponding to the brain function of the subject.

A driver state determination device according to a third aspect of the present invention is the driver state determination device of the first aspect, further including a brain function activation information detection unit and a determination component extraction unit. The brain function activation information detection unit detects brain function activation information, which activates human brain function, provided to the subject driving the machine. The determination component extraction unit extracts, from the plurality of components, a component related to the brain function activation information as the determination component.

With the driver state determination device according to the third aspect, the plurality of components is obtained by subjecting the facial change information to singular value decomposition, principal component analysis, or independent component analysis, and the determination component related to the detected brain function activation information is extracted from the plurality of components. As such, the presence/absence of brain activity of the subject can be easily estimated without using electrodes or the like that require pretreatment before being applied. As a result, the driver state of the subject driving the machine can be easily determined on the basis of the determination component corresponding to the brain function of the subject.

A driver state determination device according to a fourth aspect of the present invention is the driver state determination device of the first aspect, further including a brain activity related change amount extraction unit and a determination component extraction unit. The brain activity related change amount extraction unit extracts, as a brain activity related change amount, an amount of change related to human brain activity from a predetermined amount of change caused by a predetermined operation on a machine. The determination component extraction unit extracts, from the plurality of components, a component related to the brain activity related change amount as the determination component.

With the driver state determination device according to the fourth aspect, the plurality of components is obtained by subjecting the facial change information to singular value decomposition, principal component analysis, or independent component analysis, and the determination component related to the brain activity related change amount is extracted from the plurality of components. As such, the presence/absence of brain activity of the subject can be estimated without using electrodes or the like that require pretreatment before being applied. As a result, the driver state of the subject driving the machine can be easily determined on the basis of the component corresponding to the brain function of the subject. A driver state determination device according to a fifth aspect of the present invention is the driver state determination device of any one of the second to fourth aspects, wherein the determination component extraction unit extracts the determination component on the basis of a value of a critical rate.

With the driver state determination device according to the fifth aspect, the component related to the brain function activation information is extracted on the basis of the value of the critical rate. As such, reliability of the determination can be enhanced.

A driver state determination device according to a sixth aspect of the present invention is the driver state determination device of any one of the second to fifth aspects, further including a determination information storage unit. An amount of change of a predetermined range is associated with a driver state level and stored as determination information in the determination information storage unit. The amount of change is defined as an amount of change, of a correlation value of a determination component calculated for the brain function activation information or a brain activity related change amount, from a reference correlation value of a reference determination component calculated for the brain function activation information or the brain activity related change amount. Additionally, the driver state determination unit calculates the correlation value of the determination component to the brain function activation information or the brain activity related change amount, and determines the driver state level of the subject on the basis of the calculated correlation value and the determination information.

With the driver state determination device according to the sixth aspect, the reference determination component obtained prior to a predetermined action can be used to easily determine the driver state level.

A driver state determination device according to a seventh aspect of the present invention is the driver state determination device of any one of the second to sixth aspects, wherein the driver state determination unit calculates the correlation value of the determination component to the brain function activation information or the brain activity related change amount, and determines the driver state level of the subject on the basis of the calculated correlation value and the determination information. In this case, a determination information provision device on a network includes a determination information storage unit. An amount of change of a predetermined range is stored, associated with a driver state level, as determination information in the determination information storage unit. The amount of change is defined as an amount of change, of a correlation value of a determination component calculated for the brain function activation information or a brain activity related change amount, from a reference correlation value of a reference determination component calculated for the brain function activation information or the brain activity related change amount.

With the driver state determination device according to the seventh aspect, the determination information provision device on the network can be used to determine the driver state level of the subject.

A driver state determination device according to an eighth aspect of the present invention is the driver state determination device of any one of the second to seventh aspects, wherein the machine driven by the subject is an automatic machine including at least one from the group consisting of an automobile, a railway vehicle, an aircraft, a nuclear power generation equipment, and a plant machine.

With the driver state determination device according to the eighth aspect, the driver state of an automatic machine such as an automobile, a railway vehicle, an aircraft, a nuclear power generation equipment, and a plant can be determined.

A driver state determination device according to a ninth aspect of the present invention is the driver state determination device of the fourth aspect, wherein the machine is an automatic machine including at least one from the group consisting of an automobile, a railway vehicle, an aircraft, a nuclear a power generation equipment, and a plant machine; and the brain activity related change amount extraction unit extracts the brain activity related change amount from an amount of change in a command signal to the automatic machine.

With the driver state determination device according to the ninth aspect, the driver state of the subject driving the automatic machine, including at least from the group consisting of an automobile, a railway vehicle, an aircraft, a nuclear power generation equipment, and a plant machine, can be determined.

A driver state determination device according to a tenth aspect of the present invention is the driver state determination device of the fourth aspect, wherein the machine driven by the subject is a transportation machine including at least one from the group consisting of automobiles, railway vehicles, and aircraft; and the brain activity related change amount extraction unit extracts the brain activity related change amount from an amount of change in an acceleration of the transportation machine.

With the driver state determination device according to the tenth aspect, the driver state of the subject driving the transportation machine, including at least one from the group consisting of automobiles, railway vehicles, and aircraft, can be determined on the basis of the acceleration.

A driver state determination device according to an eleventh aspect of the present invention is the driver state determination device of the first aspect, wherein the driver state determination unit further includes brain activity estimation means and state monitoring means. The brain activity estimation means estimates brain activity of the subject on the basis of the plurality of components. The state monitoring means monitors a physiological state of the subject on the basis of the brain activity of the subject estimated by the brain activity estimation means.

With the driver state determination device according to the eleventh aspect, the brain activity of an operator is estimated on the basis of time-series facial skin temperature data and/or facial blood circulation volume data acquired by the facial change information acquisition unit. As such, with this driver state determination device, the brain activity of the operator can be estimated without using electroencephalogram electrodes or other sensors that require pretreatment before being applied. As a result, the brain activity of the operator can be easily estimated.

A driver state determination device according to a twelfth aspect of the present invention is the driver state determination device of the eleventh aspect, wherein the state monitoring means includes an analysis unit. The analysis unit analyzes a consciousness level of the subject with respect to an operation on the basis of the brain activity of the subject. As such, with this driver state determination device, the consciousness level of the operator with respect to the operation can be analyzed.

A driver state determination device according to a thirteenth aspect of the present invention is the driver state determination device of the twelfth aspect, wherein the state monitoring means includes a notification unit. The notification unit gives notice to the subject to pay attention when the consciousness level analyzed by the analysis unit declines to less than or equal to a certain level. As such, with this driver state determination device, the operator can be called to attention when the consciousness level of the operator declines.

A driver state determination device according to a fourteenth aspect of the present invention is the driver state determination device of any one of the eleventh to thirteenth aspects, further including information acquisition means. The information acquisition means enables an administrator managing the machine operated by the subject to acquire information related to the physiological state of the subject. As such, with this driver state determination device, the administrator can ascertain the physiological state of the operator.

A driver state determination device according to a fifteenth aspect of the present invention includes a step selected from the group consisting of: a brain function activation information provision step, a brain function activation information detection step or a machine change amount detection step and a brain activity related change amount extraction step; a facial change information acquisition step; a facial change information decomposition step; a determination component extraction step; and a driver state determination step. In the brain function activation information provision step, brain function activation information, which activates human brain function, is provided to the subject driving the machine. In the brain function activation information detection step, the brain function activation information, which activates human brain function and is provided to the subject driving the machine, is detected. In the machine change amount detection step, a predetermined amount of change caused by a predetermined operation on the machine is detected. In the brain activity related change amount extraction step, an amount of change related to the brain activity of the subject driving the machine is extracted, as a brain activity related change amount, from the amount of change detected in the machine change amount detection step. In the facial change information acquisition step, facial change information indicating time-series changes in facial data of the subject is acquired. In the facial change information decomposition step, the facial change information is decomposed into a plurality of components by singular value decomposition, principal component analysis, or independent component analysis. In the determination component extraction step, a component related to the brain function activation information or the brain activity related change amount is extracted from the plurality of components as a determination component. In the driver state determination step, a driver state of the subject driving the machine is determined on the basis of the determination component.

With the driver state determination method according to the fifteenth aspect, the plurality of components is obtained by subjecting the facial change information to singular value decomposition, principal component analysis, or independent component analysis, and the determination component related to the brain function activation information or the brain activity related change amount is extracted from the plurality of components. As such, the presence/absence of brain activity of the subject can be easily estimated without using electrodes or the like that require pretreatment before being applied. As a result, the driver state of the subject driving the machine can be easily determined on the basis of the determination component corresponding to the brain function of the subject.

A driver state determination method according to a sixteenth aspect of the present invention is the driver state determination method of the fifteenth aspect, wherein, in the driver state determination step, the correlation value of the determination component to the brain function activation information or the brain activity related change amount is calculated, and the driver state level of the subject driving the machine is determined on the basis of the calculated correlation value and the determination information. Here, an amount of change of a predetermined range is associated with a driver state level and stored in a determination information storage unit as determination information. The amount of change is defined as an amount of change, of a correlation value of a determination component calculated for the brain function activation information or a brain activity related change amount, from a reference correlation value of a reference determination component calculated for the brain function activation information or the brain activity related change amount.

With the driver state determination method according to the sixteenth aspect, the determination information stored in the determination information storage unit can be used to easily determine the driver state level.

A driver state determination method according to a seventeenth aspect of the present invention is the driver state determination method of the sixteenth aspect, wherein, the brain function activation information detection step, the brain function activation information provision step or the machine change amount detection step and the brain activity related change amount extraction step; the facial change information acquisition step; the facial change information decomposition step; and the determination component extraction step are executed at a predetermined timing. Then, a component related to the brain function activation information or the brain activity related change amount is extracted as a reference determination component.

With the driver state determination method according to the seventeenth aspect, the reference determination component is extracted from the facial change information of the subject at the predetermined timing. As such, a subsequent driver state of the subject can be determined with high accuracy.

A driver state determination method according to an eighteenth aspect of the present invention is the driver state determination method of the sixteenth or seventeenth aspect, wherein, in the driver state determination step, a determination information provision device is accessed when the driver state level is determined. In this case, the determination information storage unit is stored in the determination information provision device on a network.

With the driver state determination method according to the eighteenth aspect, the reference determination component stored in the determination information provision device on the external network is used to determine the driver state. As such, it is possible to streamline reference setting work. Additionally, with the method described above, big data or the like can be used to determine the driver state.

A driver state determination method according to an nineteenth aspect of the present invention is the driver state determination method of the eighteenth aspect, wherein the reference correlation value is calculated on the basis of the reference determination component which is obtained by providing the brain function activation information to a person other than the subject; or the reference correlation value is calculated on the basis of a reference determination component obtained from a brain activity related change amount during normal operation.

With the driver state determination method according to the nineteenth aspect, big data obtained from a person other than the subject or big data obtained during normal operation can be used to determine the driver state.

Advantageous Effects of the Invention

With the driver state determination device according to the first aspect, the driver state of the subject driving the machine can be easily determined.

With the driver state determination device according to the second aspect, the driver state of the subject driving the machine can be easily determined.

With the driver state determination device according to the third aspect, the driver state of the subject driving the machine can be easily determined.

With the driver state determination device according to the fourth aspect, the driver state of the subject driving the machine can be easily determined.

With the driver state determination device according to the fifth aspect, the reliability of the determination can be enhanced.

With the driver state determination device according to the sixth aspect, the driver state level can be easily determined.

With the driver state determination device according to the seventh aspect, the determination information provision device on the network can be used to determine the driver state level of the subject.

With the driver state determination device according to the eighth aspect, the driver state of the subject driving an automatic machine including at least one from the group consisting of an automobile, a railway vehicle, an aircraft, a nuclear power generation equipment, and a plant machine can be determined.

With the driver state determination device according to the ninth aspect, the driver state of the subject driving an automatic machine including at least one from the group consisting of an automobile, a railway vehicle, an aircraft, a nuclear power generation equipment, and a plant machine can be determined.

With the driver state determination device according to the tenth aspect, the driver state of the subject driving transportation machines selected from the group consisting of automobiles, railway vehicles, and aircraft can be determined on the basis of the acceleration.

With the driver state determination device according to the eleventh aspect, the brain activity of the operator can be easily estimated.

With the driver state determination device according to the twelfth aspect, the consciousness level of the operator with respect to an operation can be analyzed.

With the driver state determination device according to the thirteenth aspect, the operator can be called to attention when the consciousness level of the operator declines.

With the driver state determination device according to the fourteenth aspect, the administrator can ascertain the physiological state of the operator.

With the driver state determination method according to the fifteenth aspect, the driver state of the subject driving the machine can be easily determined.

With the driver state determination method according to the sixteenth aspect, the driver state level can be easily determined.

With the driver state determination method according to the seventeenth aspect, the driver state of the subject after a predetermined timing can be determined with high accuracy.

With the driver state determination method according to the eighteenth aspect, reference setting work can be streamlined.

With the driver state determination method according to the nineteenth aspect, big data and the like can be used to determine the driver state.

BRIEF DESCRIPTION OF THE DRAWINGS

FIG. 27 is a drawing illustrating an example in which the driver state determination device 400 according to the first embodiment includes an infrared camera 415a.

FIG. 40 is a table illustrating use examples of a driver state determination device according to a fourth embodiment.

DESCRIPTION OF EMBODIMENTS

Figure 1B:
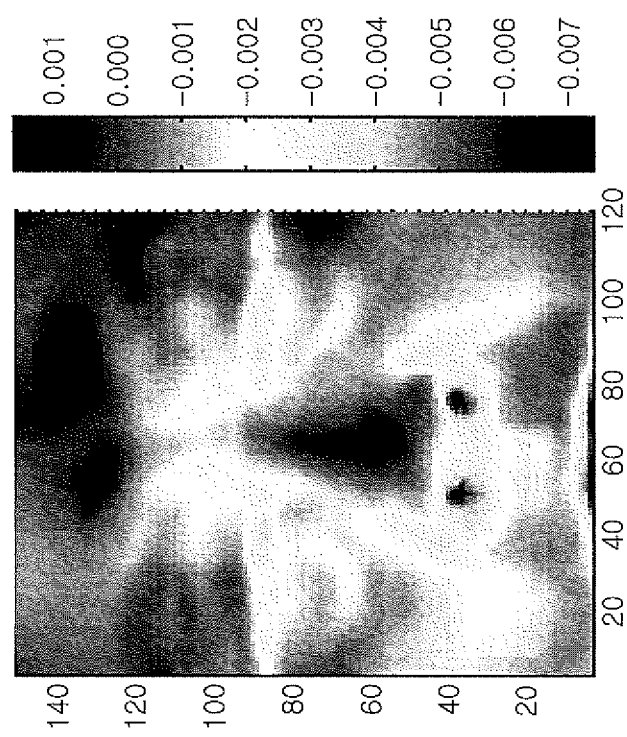
FIGS. 1A and 1B illustrate an example of photographic image data and the results of analyzing the same.

Before describing the embodiments of the present invention, the findings made by the inventors that served as an important foundation for the inventors to contrive the present invention will be described.

(1) Summary of Findings Made by the Inventors

It is known that human intellectual activity (cognitive activity and the like) and emotional activity (activity such as pleasure/displeasure) are reflected in human brain activity. Attempts to estimate human brain activity have been made in the past, but in most cases, the attempts involved using data detected by electroencephalography, magnetic resonance imaging, and/or near infrared spectroscopy.

In cases where, for example, electroencephalography is adopted as the detection method, it is necessary to attach brain wave electrodes to the subject. Additionally, resistance that occurs between the skin and the electrodes when the brain wave electrodes are attached must be reduced. Consequently, a procedure such as a process to abrade the skin or an application of a paste to the electrodes needs to be carried out. In cases where functional magnetic resonance imaging is adopted, there are restrictions on measurement conditions, such as the impossibility of measurement at any location other than an MRI room and the inability to bring metal into the measurement room. In cases where near infrared spectroscopy is adopted, a probe needs to be attached to the subject. However, wearing the probe for a long time can be painful to the subject and, in some cases, due to the contact state between the hair of the subject and the probe, the detections by the probe may not be accurate. Thus, when using conventional detection methods to measure human brain activity, a significant burden is imposed on the subject, specifically, pretreatment is needed to attach the brain wave electrodes, probes, etc., and/or the measurement conditions are limited.

Accordingly, there is a need to develop an approach whereby the burden on the subject can be reduced and also whereby human brain activity can be easily estimated.

The inventors postulated that it might be possible to estimate human brain activity on the basis of human facial skin temperature or the state of facial blood circulation, which is thought to be proportional to the facial skin temperature. Human facial skin temperature can be acquired using a measurement device such as a thermography device. The state of facial blood circulation, that is, facial blood circulation volume can be estimated from RGB data of photographic images of the facial surface, which is obtained using an imaging device. The facial skin temperature and/or photographic images of the facial surface can be acquired without using electroencephalogram electrodes, probes, or other sensors that require pretreatment before being applied.

However, it is known that human facial skin temperature changes under the influence of various factors such as outside air temperature and/or autonomic nervous activity. As such, when attempting to estimate brain activity on the basis of the facial skin temperature or on the basis of the facial blood circulation volume, which is thought to be proportional to the facial skin temperature, it is very difficult to determine whether only brain activity is reflected in the acquired data.

After much research, the present inventors discovered that it is possible to identify a component indicating a change in the facial skin temperature or a change in the facial blood circulation volume in brain activity by: detecting the facial skin temperature; decomposing, into a plurality of components, time-series facial skin temperature data including the detected temperature data and position data (coordinate data) of the detection site, or decomposing, into a plurality of components, time-series facial blood circulation volume data calculated on the basis of RGB data obtained from time-series photographic image data of the facial surface, by singular value decomposition, principal component analysis, or independent component analysis; and analyzing the plurality of the decomposed components. Thus, the present inventors conceived the present invention, in which the brain activity of the subject is estimated and analyzed, thereby enabling the visualization of the physiological state of the subject on the basis of the estimated brain activity.

(2) Acquisition Method of Various Facial Data and Analysis Method of Acquired Various Facial DATA (2-1) Acquisition Method of Facial Skin Temperature Data and Analysis Method of Facial Skin Temperature Data Next, a description is given of an acquisition method of facial skin temperature data and analysis method of facial skin temperature data used by the present inventors to reach the findings described above.

In this test, facial skin temperature data was acquired from six subjects. Specifically, each subject was seated in a chair placed in an artificial climate room maintained at a room temperature of 25° C., and facial skin temperature data was acquired from the entire facial surface of the subject using an infrared thermography device. The infrared thermography device was capable of detecting infrared radiant energy emitted from the subject using an infrared camera, converting the detected infrared radiant energy to a facial temperature (herein, the temperature in Celsius) of the subject, and displaying and/or storing a temperature distribution thereof as facial skin temperature data (e.g. image data representing the temperature distribution). In this test, an R300 (manufactured by NEC Avio Infrared Technologies Co., Ltd.) was used as the infrared thermography device. The infrared camera was set in front of the subject at a position 1.5 m away from the subject. The facial skin temperature data was acquired for 30 minutes.

Additionally, in this test, brain function activation tasks were given to the subjects while the facial skin temperature data was being acquired. Thus, facial skin temperature data during brain resting time and facial skin temperature data during brain activated time were acquired. The brain function activation tasks were presented to the subjects as images on a display device or the like. Examples thereof included calculation, recognition of numbers, shapes, and colors, memorization of symbols, letters, and language, and other psychological tasks. In this test, mental multiplication was used as the brain function activation task. The subjects were instructed to multiply numbers displayed in longhand on the display device, and input answers using a keyboard. In this test, the brain function activation tasks were continuously given to the subjects for ten minutes after five minutes had elapsed since the start of acquiring the facial skin temperature data.

To analyze the facial skin temperature data, the acquired facial skin temperature data was subjected to singular value decomposition. Here, Singular Value Decomposition (SVD) of MATLAB (registered trademark) was used as the analysis tool. In the singular value decomposition, the target was set as all of the time-series facial skin temperature data acquired (30-minutes of data), the factor was set as time data of every 30 seconds (60 time points for 30 minutes), and the measure was set as the facial skin temperature data (240×320 pixels) during each period (the 30 seconds). The facial skin temperature data X was decomposed into a plurality of components by singular value decomposition. Then, for each component, a time distribution V, a space distribution U, and a singular value S representing the magnitude of the component were calculated. The relationships between these values is expressed in the following equation. Note that V' is a matrix obtained by interchanging the columns and rows of V.

$$X=(U*S)*V' \qquad \text{Equation 1}$$

Then, the time distribution V and the space distribution U of each component resulting from the singular value decomposition were plotted on graphs to create a component waveform diagram and a temperature distribution diagram for each component.

Furthermore, the component waveform diagram and the temperature distribution diagram for each component were analyzed to identify a component indicating a change in skin temperature that reflects brain activity.

The component waveform diagram for each component was analyzed to determine the presence/absence of correlation between the amplitude of the component waveform and each of the brain resting time and the brain activated time. Specifically, evaluations were conducted as to whether or not correlation existed between the amplitude shown in the component waveform diagram for each component and the brain resting time period/brain activated time period. In this test, during the period of acquiring the facial skin temperature data, the brain resting time was defined as a period of five minutes from the start of data acquisition and a period of 15 minutes from a point in time after 15 minutes had elapsed since the start point of data acquisition to the end of data acquisition. These were periods in which the brain function activation task was not given to the subjects.

Additionally, the brain activated time was defined as a period of 10-minutes from a point in time occurring after five minutes had elapsed since the start of data acquisition, up to a point in time after 10 minutes had elapsed. This was a period in which the brain function activation task was being given to the subjects. Then, evaluations were conducted to determine the presence/absence of correlation between the amplitude shown in the component waveform diagram for each component and each of the brain resting time and the brain activated time. Note that statistical correlation analysis was performed to determine the presence/absence of correlation. When the significance level ($\alpha$) was 0.05 or lower, it was determined that correlation existed.

The temperature distribution diagram for each component was analyzed to determine the presence/absence of temperature changes at a predetermined site on the facial surface. The brain has a mechanism called the selective brain cooling system whereby the brain is cooled independently of body temperature. The selective brain cooling system is known to discharge heat generated by brain activity using the forehead and the area around the paranasal sinuses (including the area between the eyebrows and the area around the nose). As such, in this test, the temperature distribution diagram for each component was evaluated to determine the presence/absence of temperature changes at the forehead and the area around the paranasal sinuses. Note that, in the temperature distribution diagrams, the presence/absence of temperature changes at the forehead and the area around the paranasal sinuses was evaluated on the basis of visual inspection, or on the basis of whether or not the temperatures of the forehead and the area around the paranasal sinuses differed one standard deviation (SD) or more from the average temperature of all measurement data of the temperatures of the forehead and the area around the paranasal sinuses.

Additionally, polarity (positive or negative) of the facial skin temperature data X is determined by the relationships between the values of the space distribution U, the singular value S, and the time distribution V. As such, in some cases, polarity may appear inverted in the temperature distribution diagram and the component waveform diagram for each component. Therefore, polarity was not considered when evaluating the component waveform diagrams and the temperature distribution diagrams.

As described above, in this case, the infrared thermography device converts the infrared radiant energy detected from the subject into temperatures, and uses the temperature distribution thereof as the facial skin temperature data. However, when acquiring the facial skin temperature of a human subject using the infrared thermography device, various temperature changes unrelated to brain activity (i.e. noise), such as facial movements and/or autonomic nervous activity, are also acquired as the facial skin temperature data (see FIG. 1A). Therefore, in order to detect such temperature changes that are unrelated to brain activity, relative facial skin temperature data was created for which an average of all of the temperature data included in the facial skin temperature data of every 30 seconds is set to "0", the created facial skin temperature data was also subjected to singular value decomposition in which the SVD of MATLAB (registered trademark) is used as the analysis tool, a component waveform diagram and a temperature distribution diagram for each component were created in accordance with the singular value S, and the diagrams were analyzed to identify a component indicating a change in skin temperature that reflects brain activity.

For the sake of convenience, in the following description, the facial skin temperature data, acquired by the infrared thermography device, is referred to as "facial skin temperature data based on temperature conversion data"; and the relative facial skin temperature data, for which the average of all of the temperature data included in the facial skin temperature data based on temperature conversion data obtained every predetermined time period (every 30 seconds in this test) is set to "0", is referred to as "facial skin temperature data based on relative temperature conversion data."

Additionally, for one of the six subjects, in addition to detecting the facial skin temperature using the infrared thermography device, electrodes were connected to the scalp of the subject and electroencephalograms were taken. An evaluation was conducted for correlation between the amplitude of the component waveform diagram and the amplitude of the $\beta$ wave, which is known as a waveform that appears when awake or when the consciousness is nervous (brain wave in the 14 to 30 Hz frequency range). Note that, when taking the electroencephalogram, the electrodes were arranged at six sites (F3, F4, C3, C4, Cz, and Pz) specified by the International 10-20 System.

It can be expected that the head of the subject may move vertically while the brain function activation task is given to the subject. If such movement occurs, the position of the face of the subject with respect to the infrared camera will change. Therefore, a control test was conducted on one subject in order to verify whether such changes in the position of the face influence the changes in skin temperature. In the control test to verify the influence of movement of the subject when acquiring the facial skin temperature data, the same infrared thermography device used in the test described above was used to acquire the facial skin temperature data of the subject. However, in this case, the subject was instructed also to operate the keyboard at random timings during the period in which the brain function activation task was not given (that is, during brain resting time). The facial skin temperature data based on temperature conversion data and the facial skin temperature data based on relative temperature conversion data acquired by the control test were also subjected to singular value decomposition in which the SVD of MATLAB (registered trademark) was used as the analysis tool, a component waveform diagram and a temperature distribution diagram for each component were created in accordance with the singular value S, and the diagrams were analyzed to identify a component indicating a change in skin temperature that reflects brain activity.

Figure 1A:
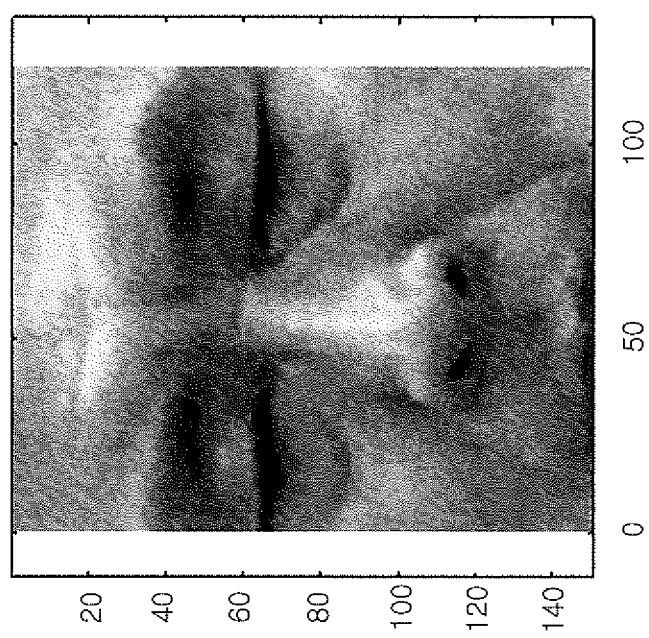

(2-2) Acquisition Method of Photographic Image Data of Facial Surface and Analysis Method of Photographic Image Data of Facial Surface FIG. 1A illustrates an example of photographic image data, captured using the imaging device, of the area around the paranasal sinuses of the facial surface of a subject. FIG. 1B illustrates an example of a blood circulation volume distribution diagram (image map).

Next, a description is given of an acquisition method of photographic image data of the facial surface and an analysis method of photographic image data of the facial surface used by the present inventors to reach the findings described above.

In this test, photographic image data of the facial surface was acquired from six subjects. Specifically, each subject was seated in a chair placed in an artificial climate room maintained at a room temperature of 25° C., and photographic image data of the area around the paranasal sinuses of the entire facial surface of the subject was acquired in time series using an imaging device capable of chronologically acquiring images.

Additionally, based on the selective brain cooling system described above, it is postulated that changes in the facial blood circulation volume, thought to be proportional to the facial skin temperature resulting from brain activity, will appear at the forehead and/or the area around the paranasal sinuses. As such, the present inventors postulated that, if the changes in the facial blood circulation volume at least at the forehead and/or the area around the paranasal sinuses could be captured, it would be possible to accurately estimate brain activity. Therefore, in this test, photographic image data of the area around the paranasal sinuses of the facial surfaces of the subjects were acquired in time series.

Additionally, in this test, an imaging device on the liquid crystal screen side of an iPad Air (registered trademark, manufactured by Apple) was used as the imaging device, and color video data was acquired as the time-series photographic image data. This imaging device was set in front of the subject at a position 1.0 m away from the subject. Then, using the imaging device, photographic image data was continuously captured for 30 minutes at an imaging period of 30 frames/second along the time axis. Thus, video data of the facial surface was acquired.

Furthermore, in this test, the brain function activation task was given to the subjects while the video data of the facial surface was being acquired. Thus, video data of the facial surface during brain resting time and video data of the facial surface during brain activated time were acquired. In this test, as in the test described above, "mental multiplication" was used as the brain function activation task. The subjects were instructed to multiply numbers displayed in longhand on the display device, and input answers using a keyboard. However, in this test, the brain function activation tasks were continuously given to the subjects for ten minutes after five minutes had elapsed since the start of acquiring the video data of the facial surface.

To analyze the video data of the facial surface, blood circulation volume data was calculated on the basis of RGB data obtained from the captured video data of the facial surface, and the calculated time-series blood circulation volume data was subjected to singular value decomposition in which SVD of MATLAB (registered trademark) was used as the analysis tool. Here, in accordance with the CIE-L*a*b* color system, an erythema index a* that correlates with skin redness and hemoglobin amount was calculated from the RGB data of the image, and this erythema index a* was used as the blood circulation volume data. In the singular value decomposition, the target was set as the blood circulation volume data (the erythema index in this case) based on the RGB data acquired from all of the chronologically acquired video data (30 minutes of data), the factor was set as time data of every 30 seconds (60 time points for 30 minutes), and the measure was set as the erythema index calculated from the RGB data for each period (every 30 seconds) (the erythema index obtained by extracting frame data of one second every 30 seconds, and calculating on the basis of the average value of the RGB values obtained from the frame data; 240×320 pixels). The time-series blood circulation volume data based on the RGB data obtained from the video data of the facial surface was decomposed into a plurality of components by singular value decomposition. Then, for each component, a time distribution V, a space distribution U, and a singular value S representing the magnitude of the component were calculated. The relationships between these values are expressed in equations similar to the above Equation 1.

Then, the time distribution V and the space distribution U of each component resulting from the singular value decomposition were plotted on graphs to create a component waveform diagram and a blood circulation volume distribution diagram for each component.

Furthermore, the component waveform diagram and blood circulation volume distribution diagram for each component were analyzed to identify a component indicating a change in the facial blood circulation volume, that is, an RGB change in the facial surface, that reflects brain activity.

The component waveform diagram for each component was analyzed to determine the presence/absence of correlation between the amplitude of the component waveform and each of the brain resting time and the brain activated time. Specifically, evaluations were conducted as to whether or not correlation existed between the amplitude shown in the component waveform diagram for each component and the brain resting time period/brain activated time period. In this test, during the period of acquiring the photographic image data of the facial surface, the brain resting time was defined as a period of five minutes from the start of data acquisition and a period of 15 minutes from a point in time after 15 minutes had elapsed since the start point of data acquisition to the end of data acquisition. These were periods in which the brain function activation task was not given to the subjects. Additionally, the brain activated time was defined as a period of 10-minutes from a point in time occurring after five minutes had elapsed since the start of data acquisition, up to a point in time after 10 minutes had elapsed. This was a period in which the brain function activation task was being given to the subjects. Then, evaluations were conducted to determine the presence/absence of correlation between the amplitude shown in the component waveform for each component and each of the brain resting time and the brain activated time. Note that statistical correlation analysis was performed to determine the presence/absence of correlation. When the significance level ($\alpha$) was 0.01 or lower, it was determined that correlation existed.

The blood circulation volume distribution diagram for each component was analyzed to determine the presence/absence of blood circulation volume changes at a predetermined site on the facial surface. The blood circulation volume distribution diagrams were created by arranging the space distributions U, calculated by pixel, at the respective positions of the pixels. The blood circulation volume distribution diagram for each component thus created was evaluated to determine the presence/absence of changes in blood circulation volume at the forehead and the area around the paranasal sinuses. Note that, in the blood circulation volume distribution diagrams, the presence/absence of a change in blood circulation volume at the forehead and the area around the paranasal sinuses was evaluated on the basis of the presence/absence of the change in the blood circulation volume that was observed through visual inspection, or on the basis of the value of the blood circulation volume at the forehead and the area around the paranasal sinuses as shown FIG. 1B was not "0.000".

Additionally, polarity (positive or negative) of the blood circulation volume data X was determined by the relationships between the values of the space distribution U, the singular value S, and the time distribution V. As such, in some cases, polarity may appear inverted in the blood circulation volume distribution diagram and the component waveform diagram for each component. Therefore, polarity was not considered when evaluating the component waveform diagrams and the blood circulation volume distribution diagrams.

Furthermore, in order to validate the correlation between the facial skin temperature and the facial blood circulation volume, while the photographic image data of the facial surfaces of the six subjects was being chronologically acquired, the facial skin temperature data was chronologically acquired using the infrared thermography device, the acquired facial skin temperature data was subjected to singular value decomposition using the SVD of MATLAB (registered trademark) as the analysis tool, a component waveform diagram for each component was created in accordance with the singular value S, and the diagrams were analyzed to determine the presence/absence of correlation between the amplitude of the component waveform and each of the brain resting time and the brain activated time. In this test, the same device described above was used as the infrared thermography device. The infrared camera was set in front of the subject at a position 1.5 m away from the subject.

When acquiring the photographic image data of the facial surface using the imaging device, in some cases sunlight or the like strikes the facial surface while imaging, reflects off the facial surface, and this reflected light enters the lens of the imaging device. In such cases, this reflected light may be recorded in the captured photographic image data of the facial surface. Here, in the RBG data obtained from the photographic image data, changes in brightness based on the facial blood circulation volume are smaller than changes in brightness based on reflected light. Consequently, if blood circulation volume calculated on the basis of RGB data obtained from photographic image data with the reflected light recorded therein is analyzed, it is considered that the RGB changes in the facial surface unrelated to brain activity (i.e. noise) could be mixed into the data. Therefore, in order to prevent the mixing of such RGB changes in the facial surface that were unrelated to brain activity, relative blood circulation volume data was created from relative RGB data obtained by setting an average of all of the RGB data taken every 30 seconds at "0". Then, the thus-created blood circulation volume data was also subjected to singular value decomposition using the SVD of MATLAB (registered trademark) as the analysis tool, and the component waveform diagram and the blood circulation volume distribution diagram for each component were created in accordance with the singular value S. Then, the diagrams are analyzed to identify a component indicating the RGB change of the facial surface that reflects brain activity.

For the sake of convenience, in the following description, the relative blood circulation volume data based on relative RGB data, for which the average of all of the RGB data obtained every predetermined time period (every 30 seconds in this test) is set to "0", is referred to as "relative conversion blood circulation volume data"; whereas the blood circulation volume data based on the RGB data before converting to the relative RGB data is referred to simply as "blood circulation volume data."

Additionally, while acquiring the time-series photographic image data of the facial surfaces of the six subjects using the imaging device, electrodes were connected to the scalps of the subjects and electroencephalogram were taken. Evaluations were conducted for correlation between the amplitude of the component waveform diagrams and the amplitude of the β wave, which are known as a waveform that appears when awake or when brain cells are active (brain waves in the 13 to 30 Hz frequency range). Note that, when taking the electroencephalograms, the electrodes were arranged at 19 sites (Fp1, Fp2, F3, F4, C3, C4, P3, P4, O1, O2, F7, F8, T3, T4, T5, T6, Fz, Cz, and Pz) on the scalp specified by the International 10-20 System.

Furthermore, it can be expected that the heads of the subjects may move vertically while the brain function activation task is given to the subjects. If such movement occurs, the positions of the faces of the subjects with respect to the imaging device will change. A control test was conducted on one subject in order to verify whether such changes in the position of the face influence the RGB changes in the facial surface. In the control test, as in the test described above, the imaging device was used to acquire the time-series photographic image data of the facial surface of the subject. However, in this case, the subject was instructed to operate the keyboard at random timings during the period in which the brain function activation task was not given (that is, during brain resting time). Furthermore, the time-series blood circulation volume data, based on the RGB data obtained from the time-series photographic image data of the facial surface captured in the control test, was subjected to singular value decomposition using the SVD of MATLAB (registered trademark) as the analysis tool, a component waveform diagram for each component was created in accordance with the singular value S Then, the diagrams were analyzed to determine the presence/absence of correlation between the amplitude of the component waveform and each of the brain resting time and the brain activated time. Additionally, an analysis was conducted to determine the presence/absence of correlation between the amplitude of each component waveform and actual facial movement. The actual facial movement was evaluated by acquiring, from the photographic image data, a two-dimensional coordinate of a point corresponding to an actual point at the face, and calculating a movement distance of the face every 30 seconds when imaging. In these calculations, the photographic image data at the start of the control test was used as a reference. Furthermore, an analysis was also conducted to determine the presence/absence of correlation between the amplitude of each component waveform and the number of inputs on the keyboard during imaging. The number of inputs on the keyboard during imaging was evaluated by calculating a simple moving average every 30 seconds in the time-series photographic image data.

(3) Analysis Results (3-1) Facial Skin Temperature Data Analysis Results

Figure 2A:
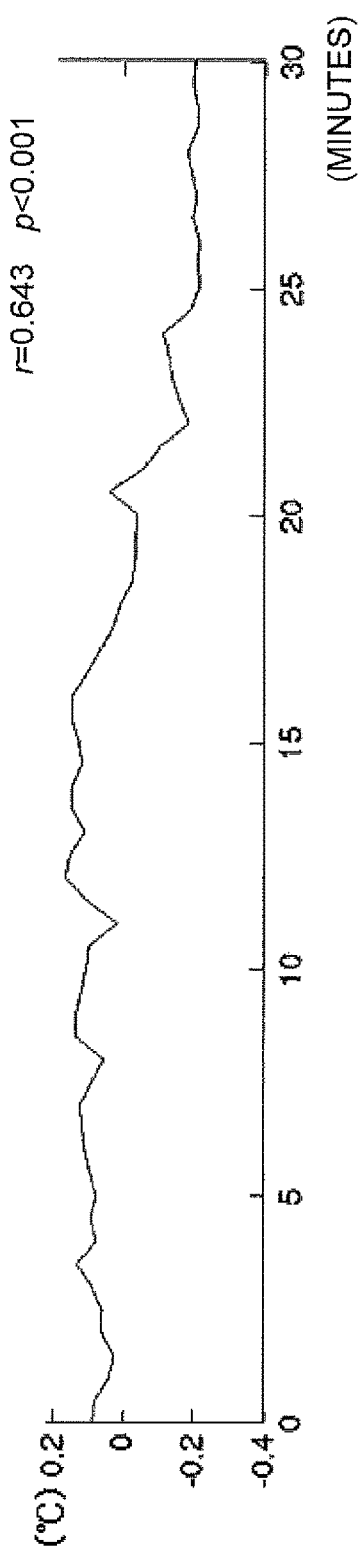
FIGS. 2A and 2B illustrate a portion of the results of analyzing facial skin temperature data.
Figure 2B:
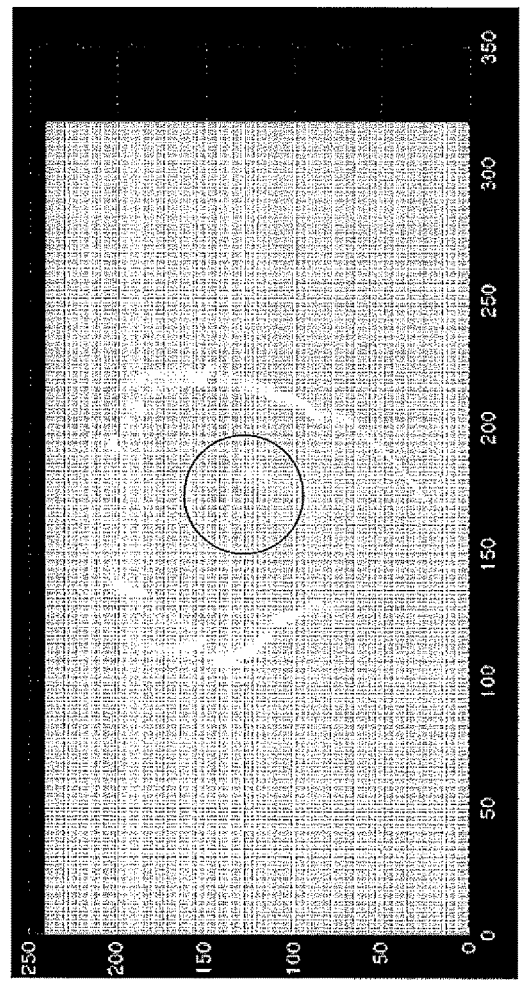
Figure 3A:
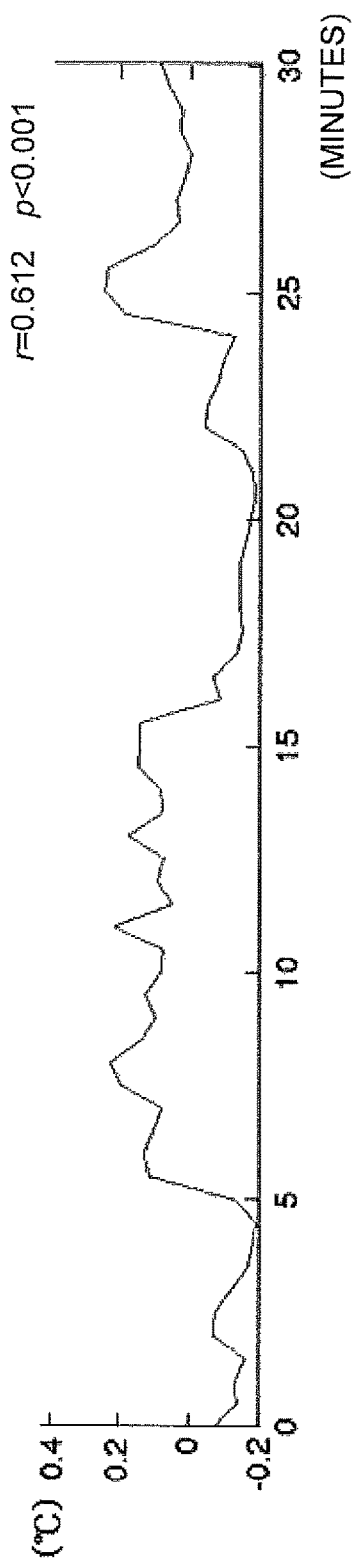
FIGS. 3A and 3B illustrate a portion of the results of analyzing the facial skin temperature data.
Figure 3B:
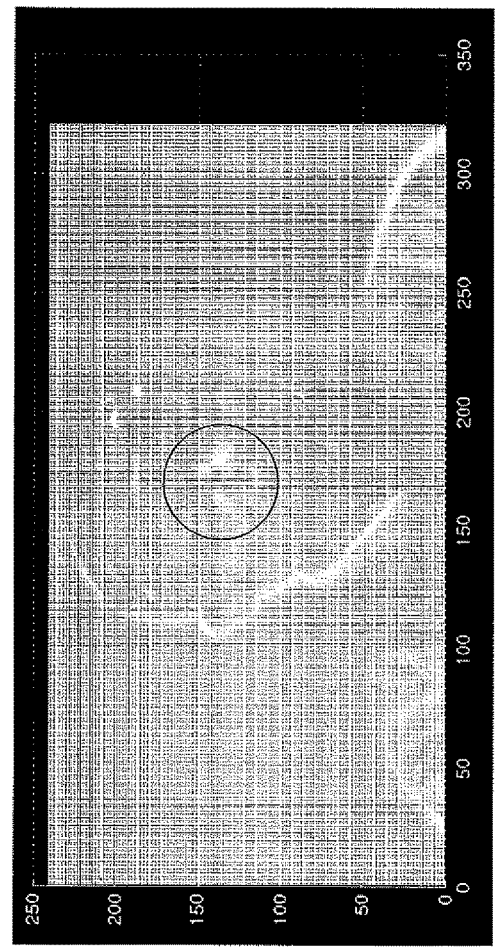
Figure 4:
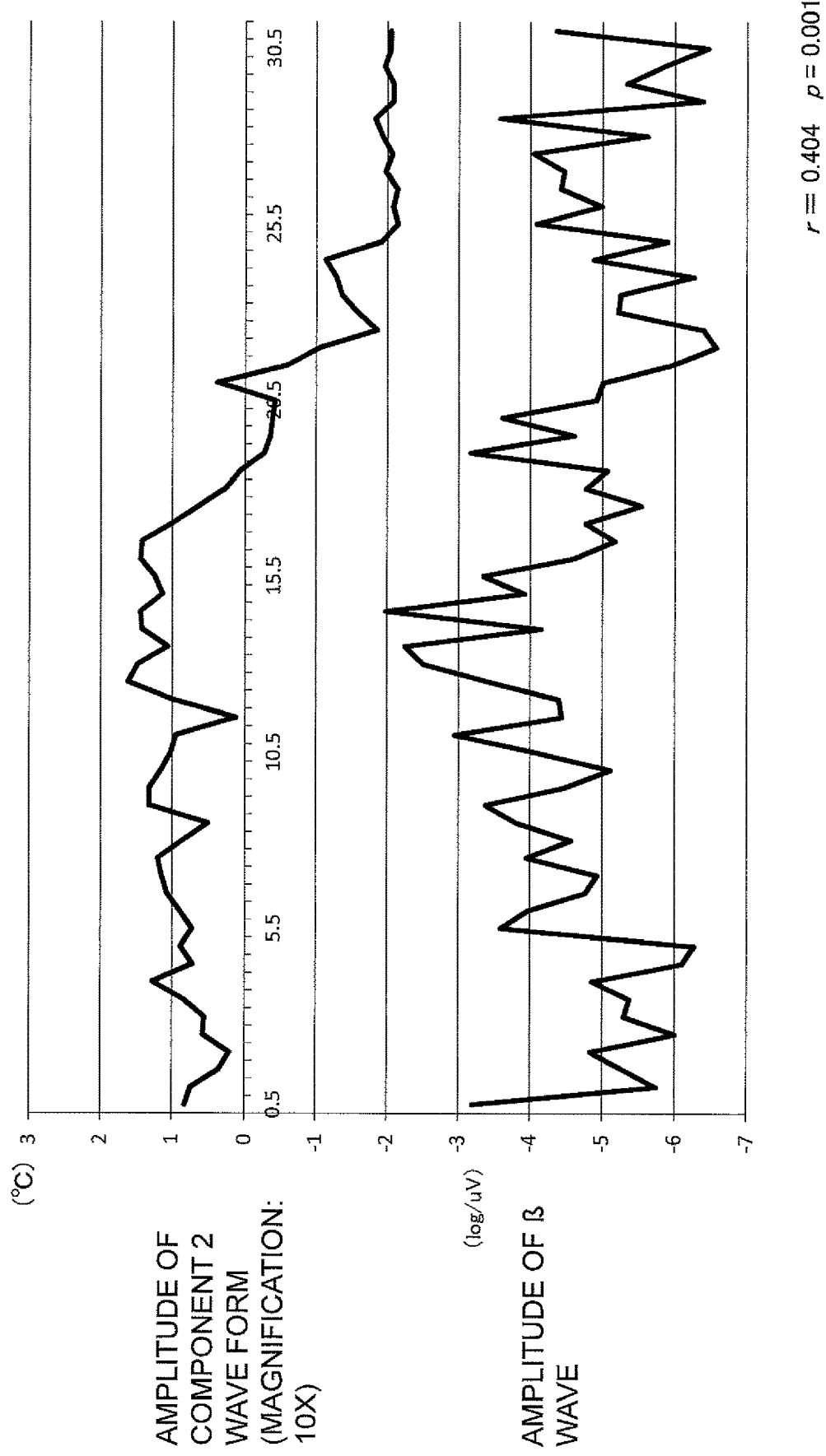
FIG. 4 is a chart illustrating the amplitude of a component waveform of a component 2, and the amplitude of the β wave of the measured brain waves.
Figure 5:
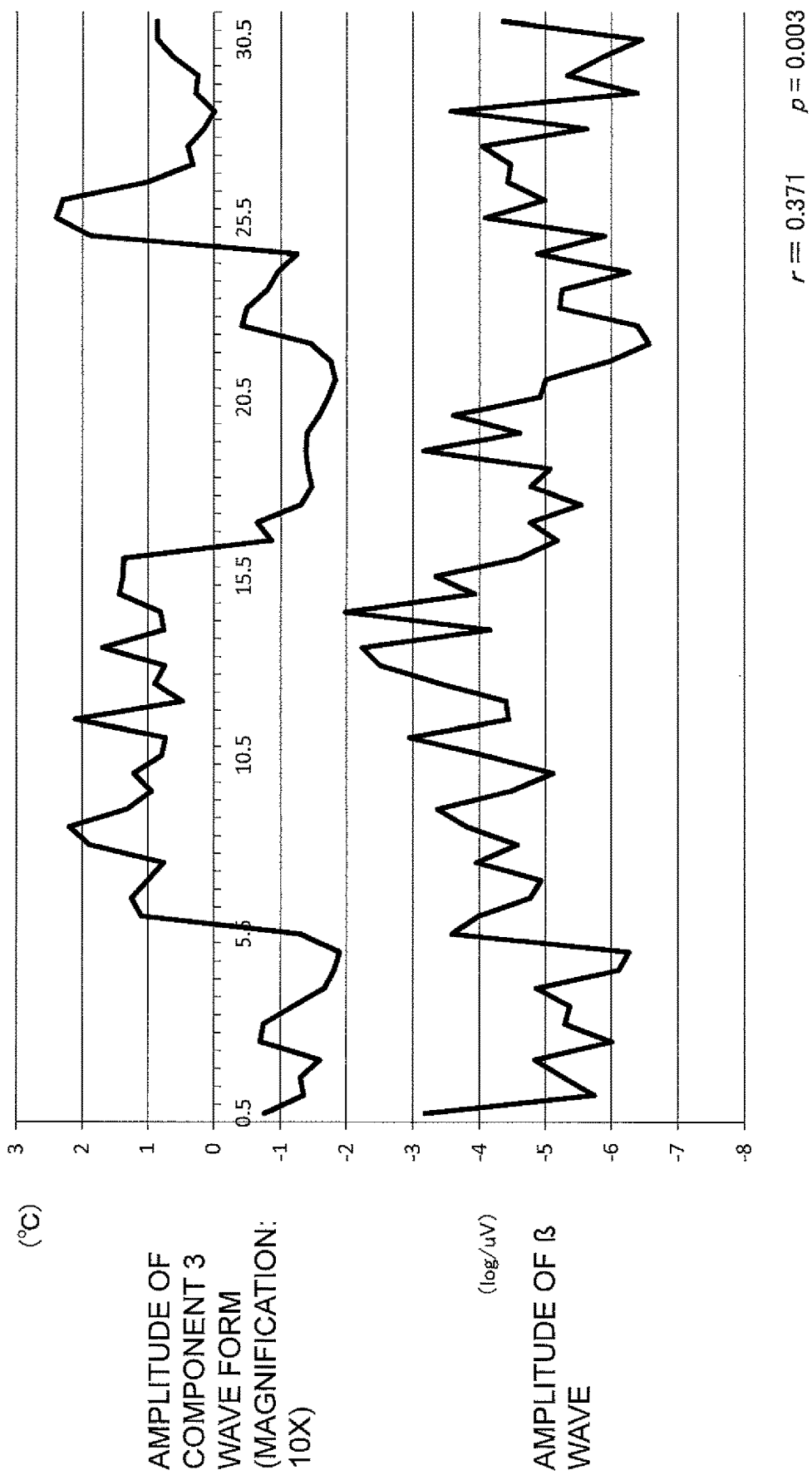
FIG. 5 is a chart illustrating the amplitude of a component waveform of a component 3, and the amplitude of the β wave of the measured brain waves.

FIG. 2 illustrate a portion of the results of analyzing the facial skin temperature data based on the temperature conversion data. FIG. 2A illustrates the component waveform diagram of a component 2 of a subject 1. FIG. 2B illustrates the temperature distribution diagram of the component 2 of the subject 1. FIG. 3A illustrates the component waveform diagram of a component 3 of the subject 1. FIG. 3B illustrates the temperature distribution diagram of the component 3 of the subject 1. FIGS. 4 and 5 illustrate relationships between the amplitudes of the component waveforms and brain waves. FIG. 4 illustrates the amplitude of the component waveform of the component 2 of the subject 1, and the amplitude of the β wave of the measured brain waves. FIG. 5 illustrates the amplitude of the component waveform of the component 3 of the subject 1, and the amplitude of the β wave of the measured brain waves. FIGS.

Figure 6A:
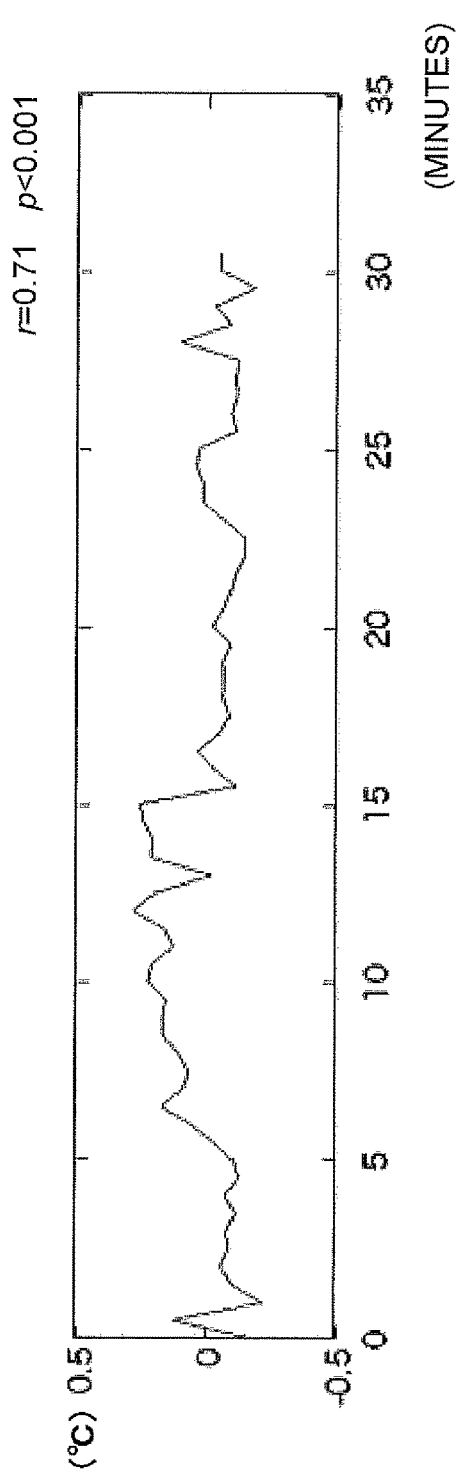
FIGS. 6A and 6B are a chart illustrating a portion of the results of analyzing the facial skin temperature data obtained in a control test.
Figure 6B:
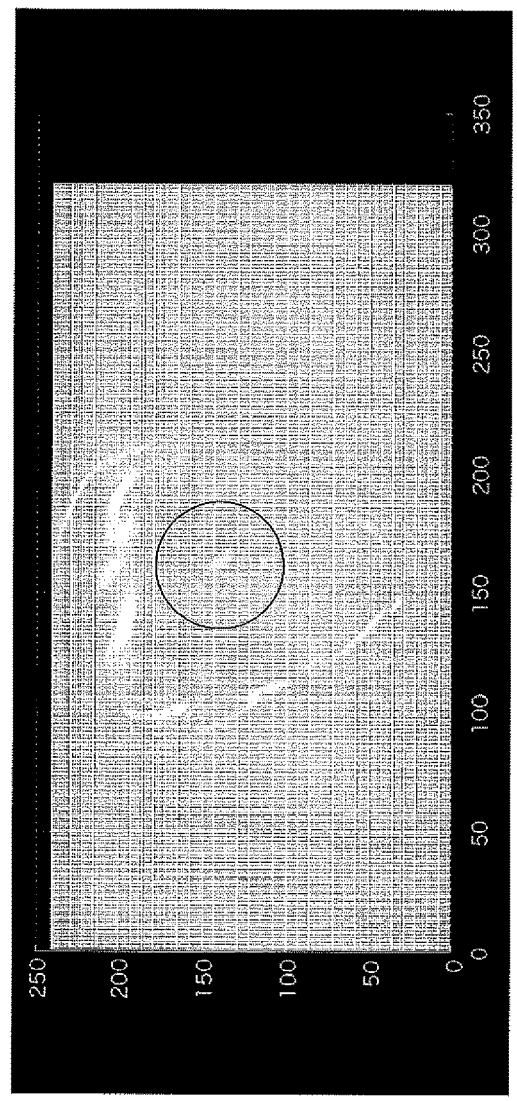

6A and 6B illustrate a portion of the results of analyzing the facial skin temperature data obtained in the control test. FIG. 6A illustrates the component waveform diagram of the component 3. FIG. 6B illustrates the temperature distribution diagram of the component 3.

Table 1 shows the results of analyzing the facial skin temperature data for each subject.

From the results obtained by analyzing the facial skin temperature data described above, significant correlation was found between human brain activity and the component 2 and/or the component 3 of the plurality of components obtained by decomposing the time-series facial skin temperature data by singular value decomposition.

TABLE 1

| Subject | Correlation in Data Based on Absolute Temperature Conversion Data | | Correlation in Data Based on Relative Temperature Conversion Data | |
|---|---|---|---|---|
| | Component waveform | Temperature distribution | Component waveform | Temperature distribution |
| Subject 1 | Component 2, Component 3 | Component 2, Component 3 | Component 2, Component 3 | Component 2, Component 3 |
| Subject 2 | Component 3 | Component 3 | Component 3 | Component 3 |
| Subject 3 | Component 1, Component 2, Component 3 | Component 2, Component 3 | Component 2, Component 3 | Component 2, Component 3 |
| Subject 4 | Component 2, Component 3 | Component 2, Component 3 | Component 2, Component 3 | Component 2, Component 3 |
| Subject 5 | Component 2, Component 3 | Component 2, Component 3 | Component 2, Component 3 | Component 2, Component 3 |
| Subject 6 | Component 2, Component 5 | Component 2, Component 5 | Component 2, Component 5 | Component 2, Component 5 |

As illustrated in FIGS. 4 and 5, from the results of analyzing the brain waves, significant correlation was found between the amplitude of the β wave of the brain waves and the amplitudes of the component 2 and the component 3.

Furthermore, in the control test, even in states where the subject moved while the facial skin temperature data was being acquired, there was significant correlation between the component 3 and human brain activity (see FIG. 6). From these results, it was found that movement by the subject when acquiring the facial skin temperature data does not influence the component 3 of the plurality of components.

Based on these results, the present inventors made the following findings.

The time-series facial skin temperature data acquired from the subjects were decomposed into the plurality of components by singular value decomposition. As a result of analyzing each of the decomposed components, it was found that the component 3 of the plurality of components is a component that is related to brain activity. Specifically, it was found that it is possible to identify a component indicating a change in skin temperature that reflects brain activity from the plurality of components by decomposing the time-series facial skin temperature data into the plurality of components by singular value decomposition, extracting components having correlation with the activation/resting of the brain from the decomposed plurality of components, and analyzing the extracted components using the selective brain cooling system. Thus, the present inventors found that it is possible to estimate brain activity on the basis of human facial skin temperature.

(3-2) Results of Analyzing Photographic Image Data of Facial Surface

Figure 7:
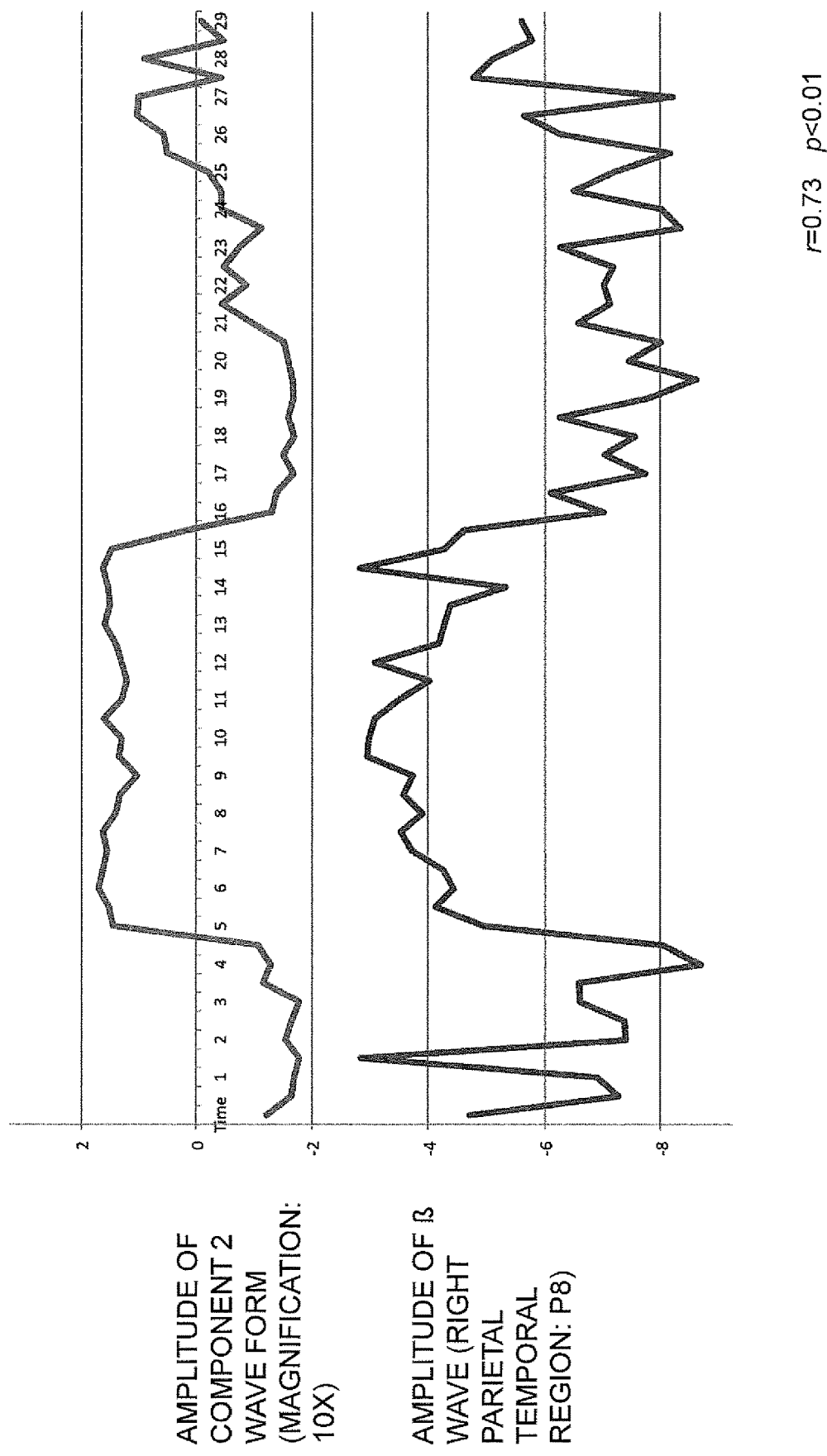
FIG. 7 is a chart illustrating a portion of the results of analyzing a component waveform based on the photographic image data of the facial surface.
Figure 8:
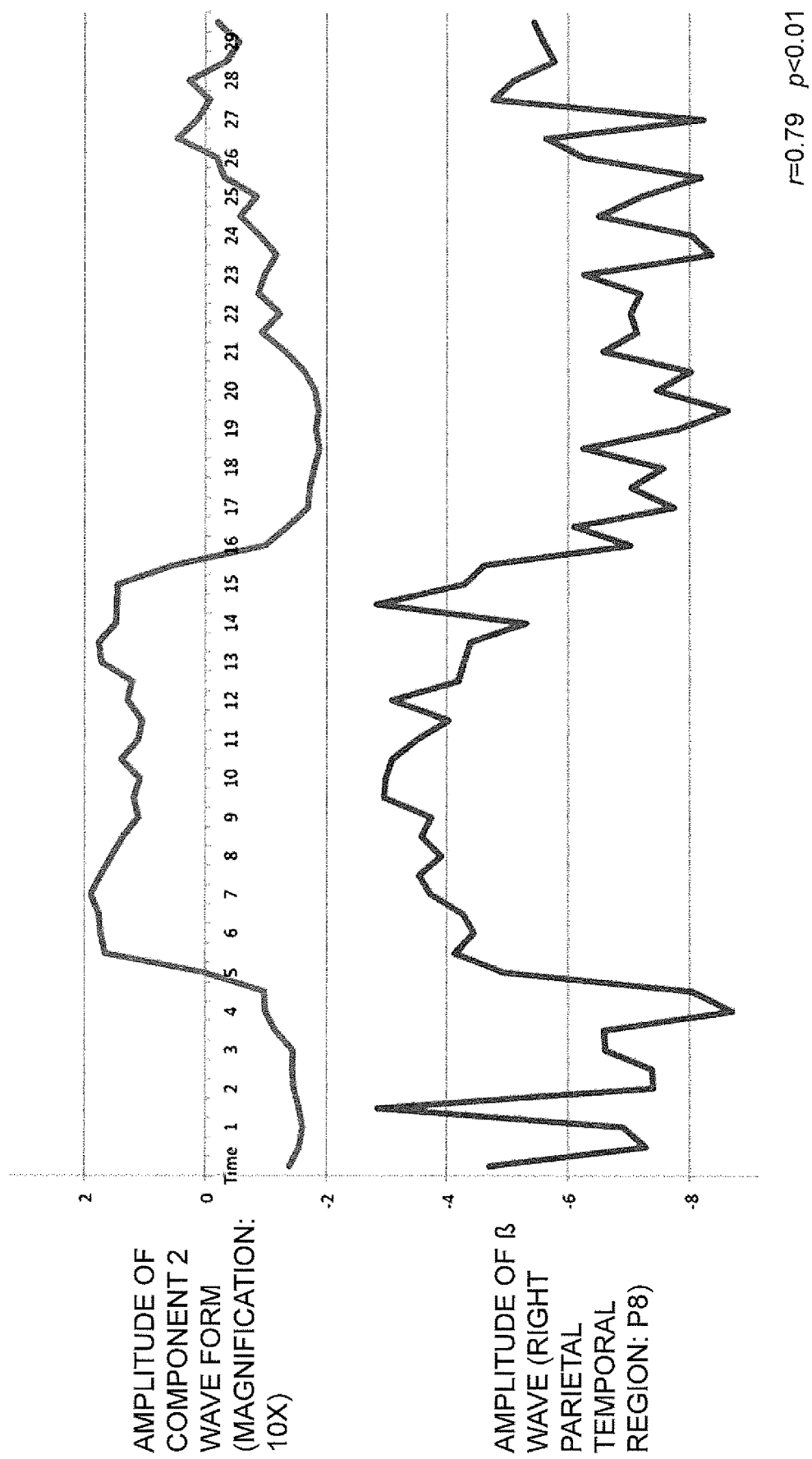
FIG. 8 is a chart illustrating a portion of the results of analyzing a component waveform based on the facial skin temperature data.
Figure 9:
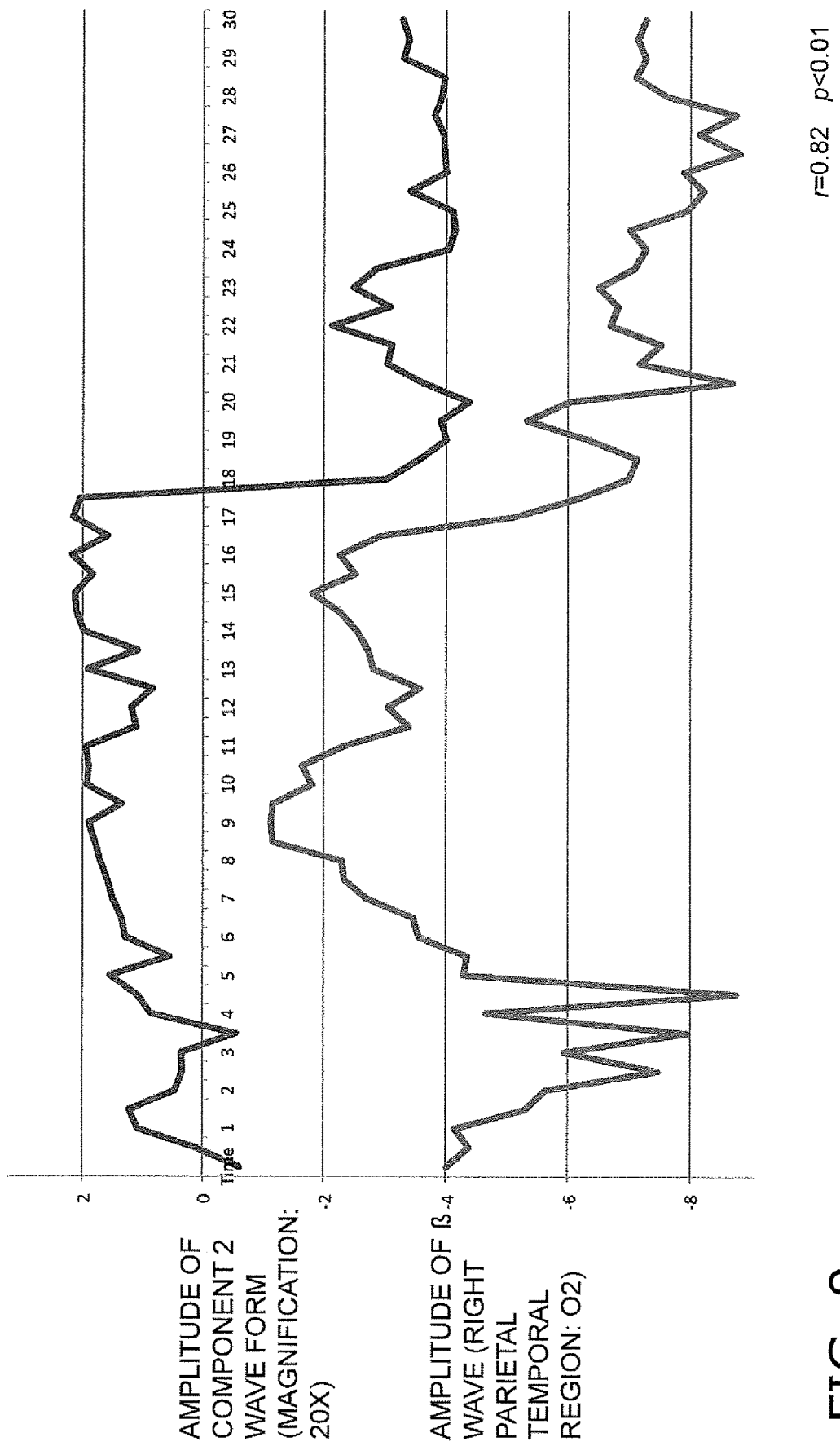
FIG. 9 is a chart illustrating a portion of the results of analyzing a component waveform based on the photographic image data of the facial surface.
Figure 10:
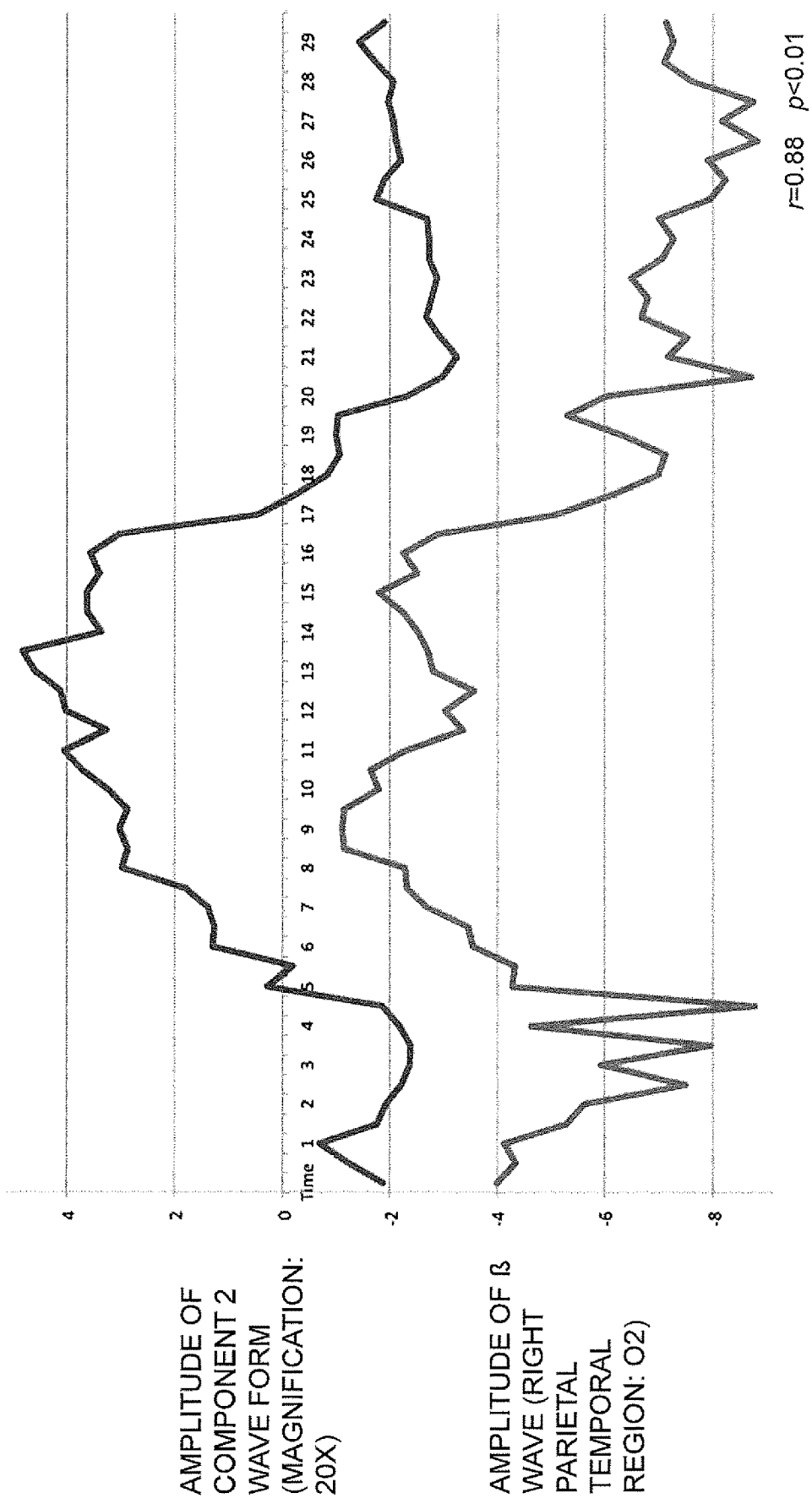
FIG. 10 is a chart illustrating a portion of the results of analyzing a component waveform based on the facial skin temperature data.
Figure 11:
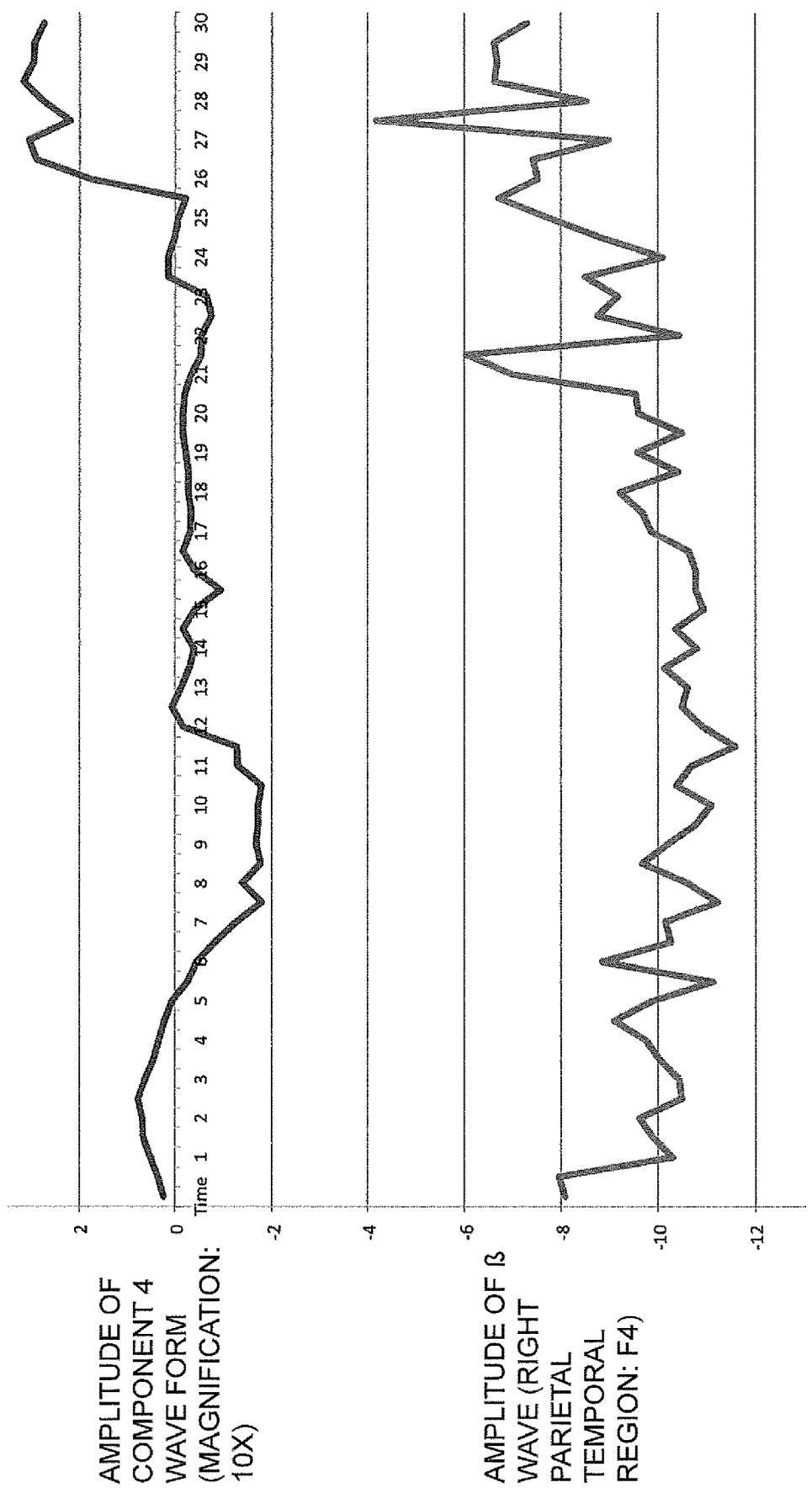
FIG. 11 is a chart illustrating a portion of the results of analyzing a component waveform based on the photographic image data of the facial surface.
Figure 12:
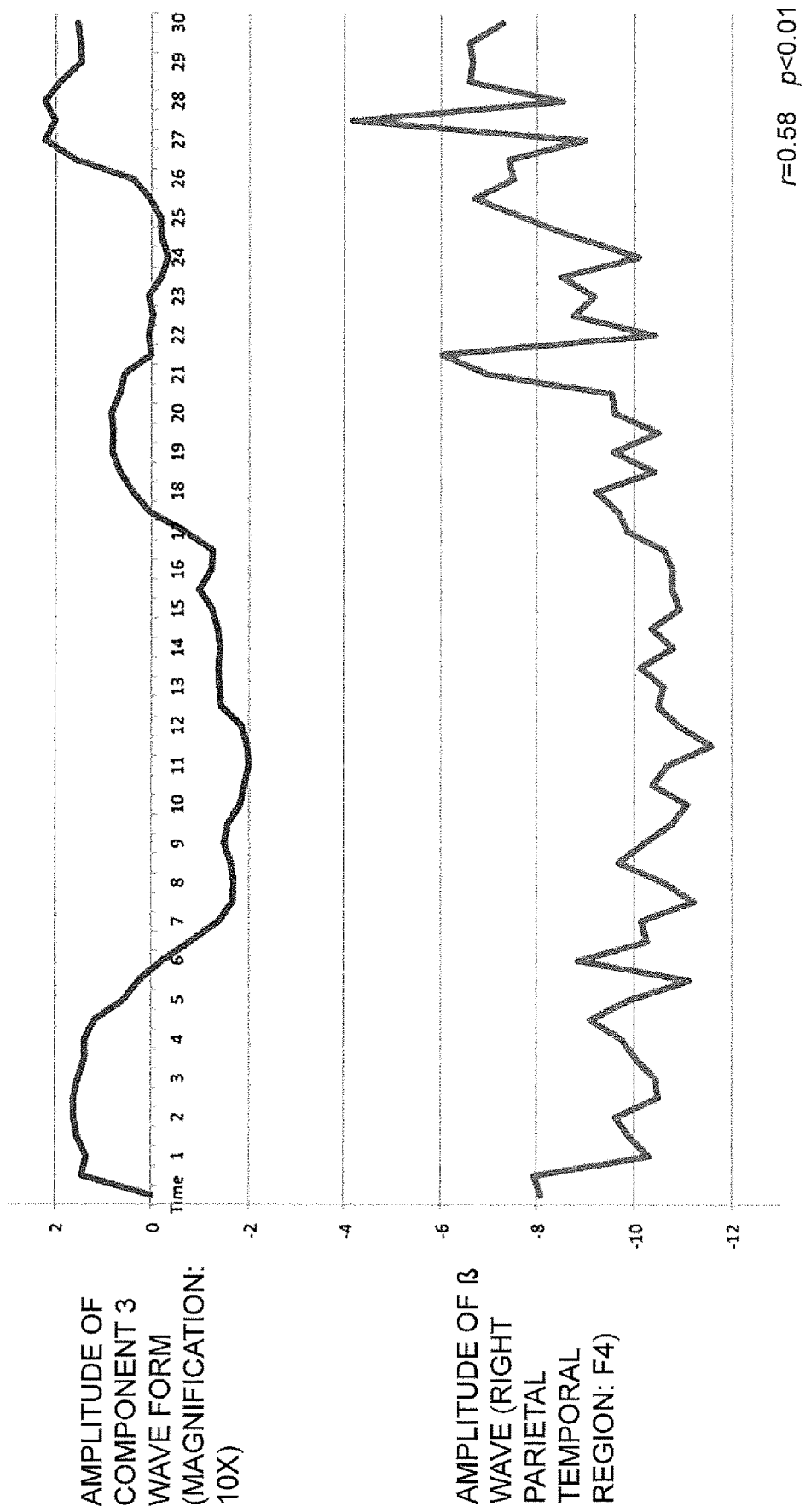
FIG. 12 is a chart illustrating a portion of the results of analyzing a component waveform based on the facial skin temperature data.
Figure 13:
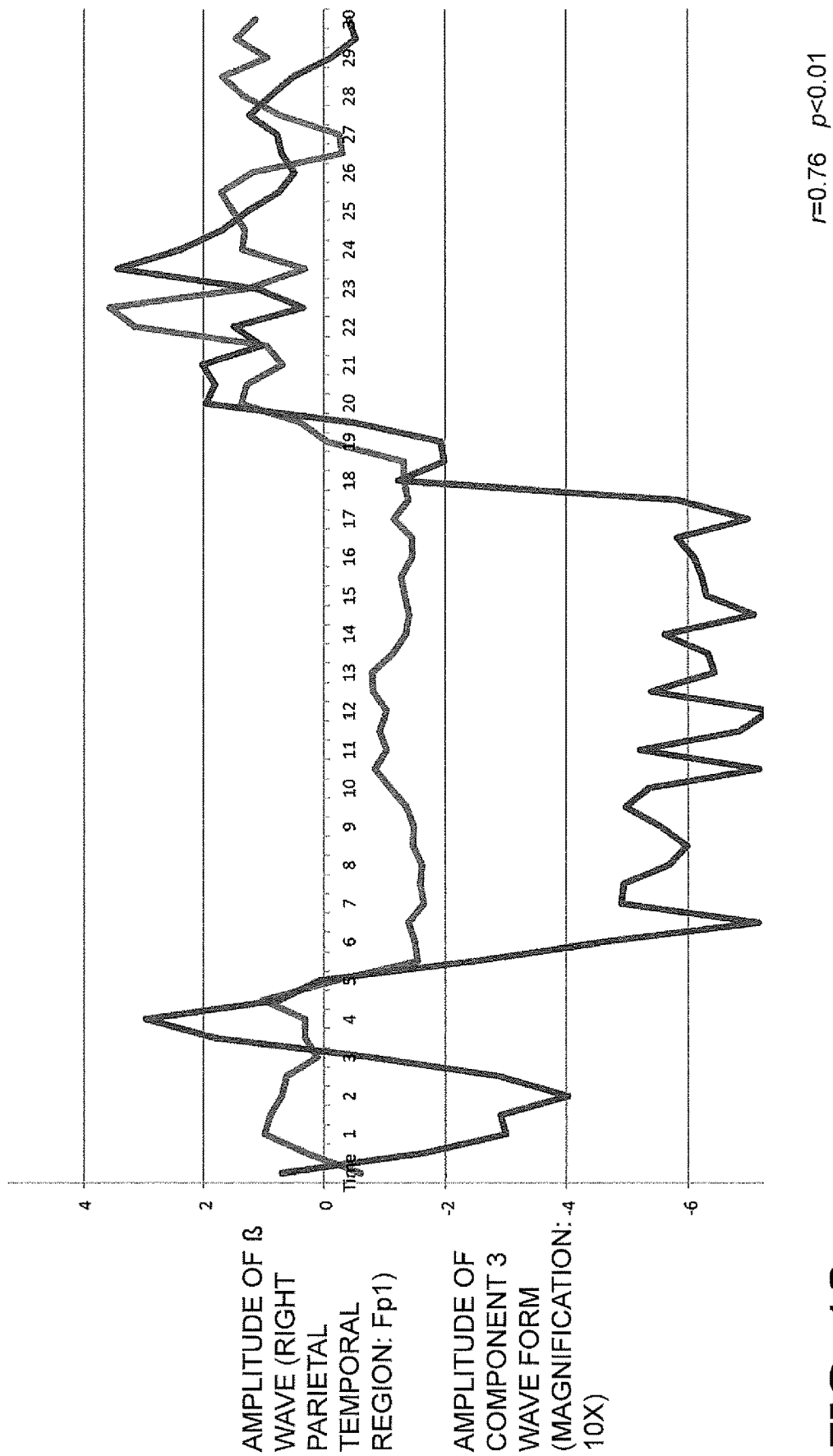
FIG. 13 is a chart illustrating a portion of the results of analyzing a component waveform based on the photographic image data of the facial surface.
Figure 14:
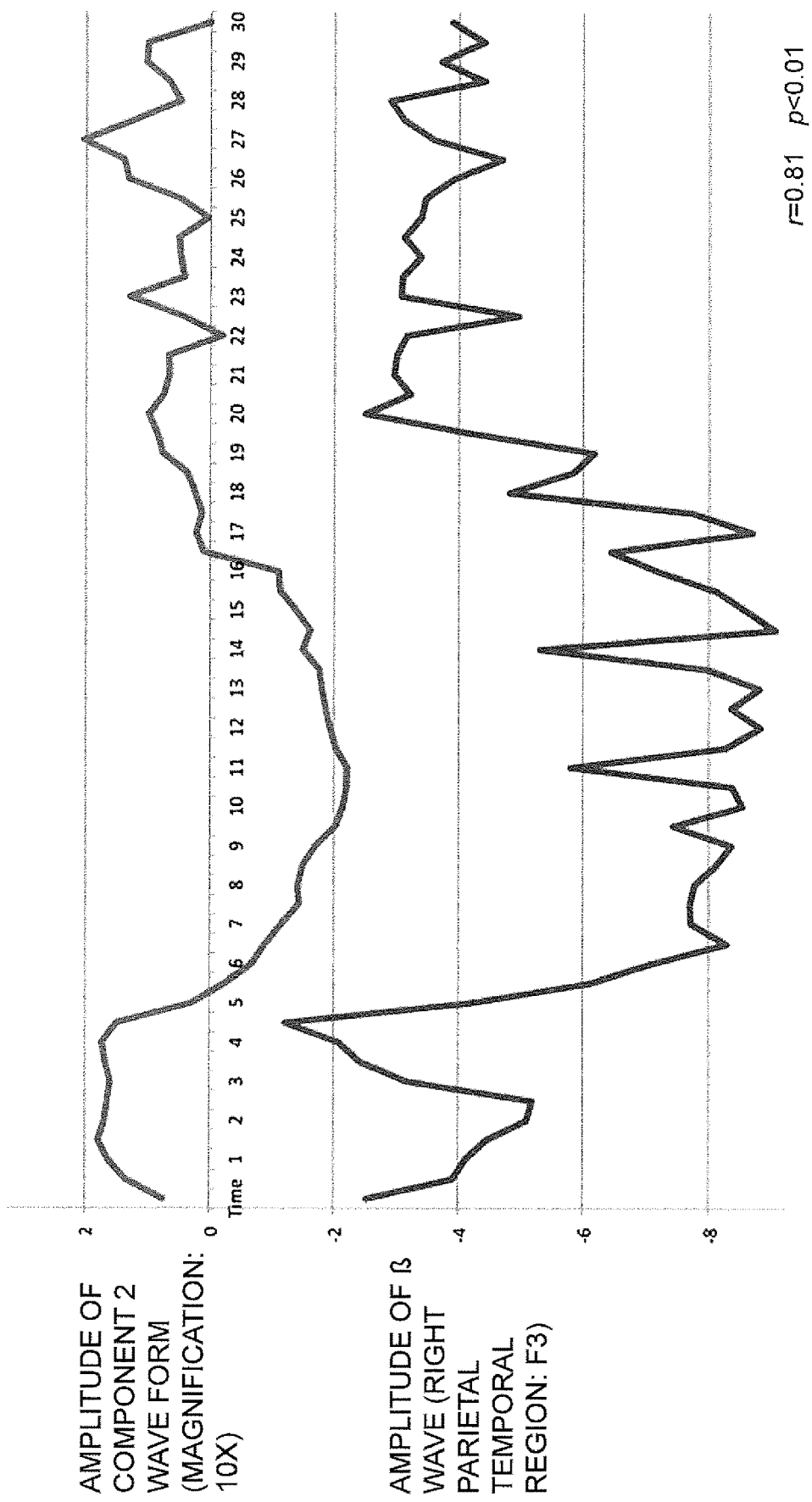
FIG. 14 is a chart illustrating a portion of the results of analyzing a component waveform based on the facial skin temperature data.
Figure 15:
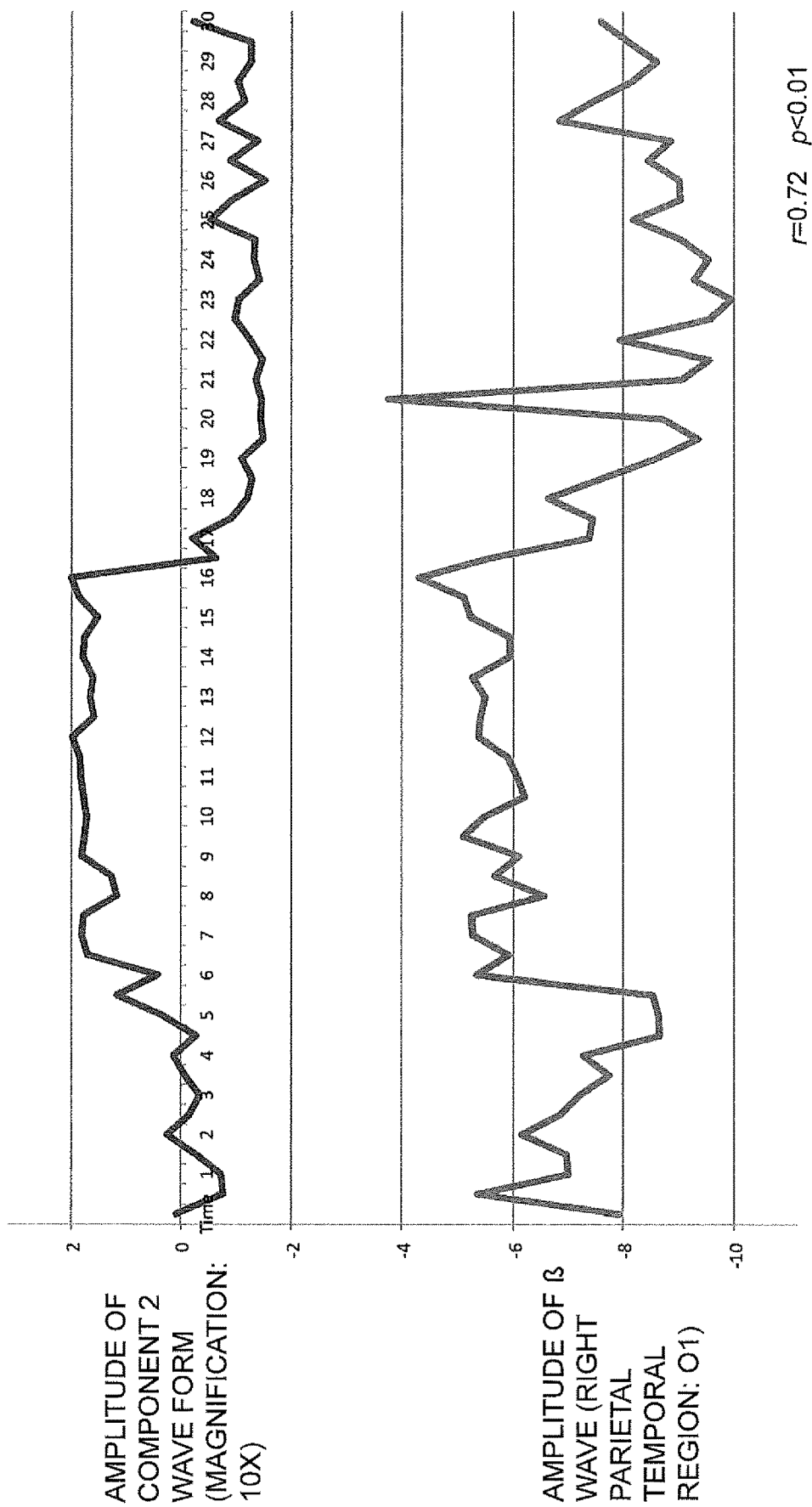
FIG. 15 is a chart illustrating a portion of the results of analyzing a component waveform based on the photographic image data of the facial surface.
Figure 16:
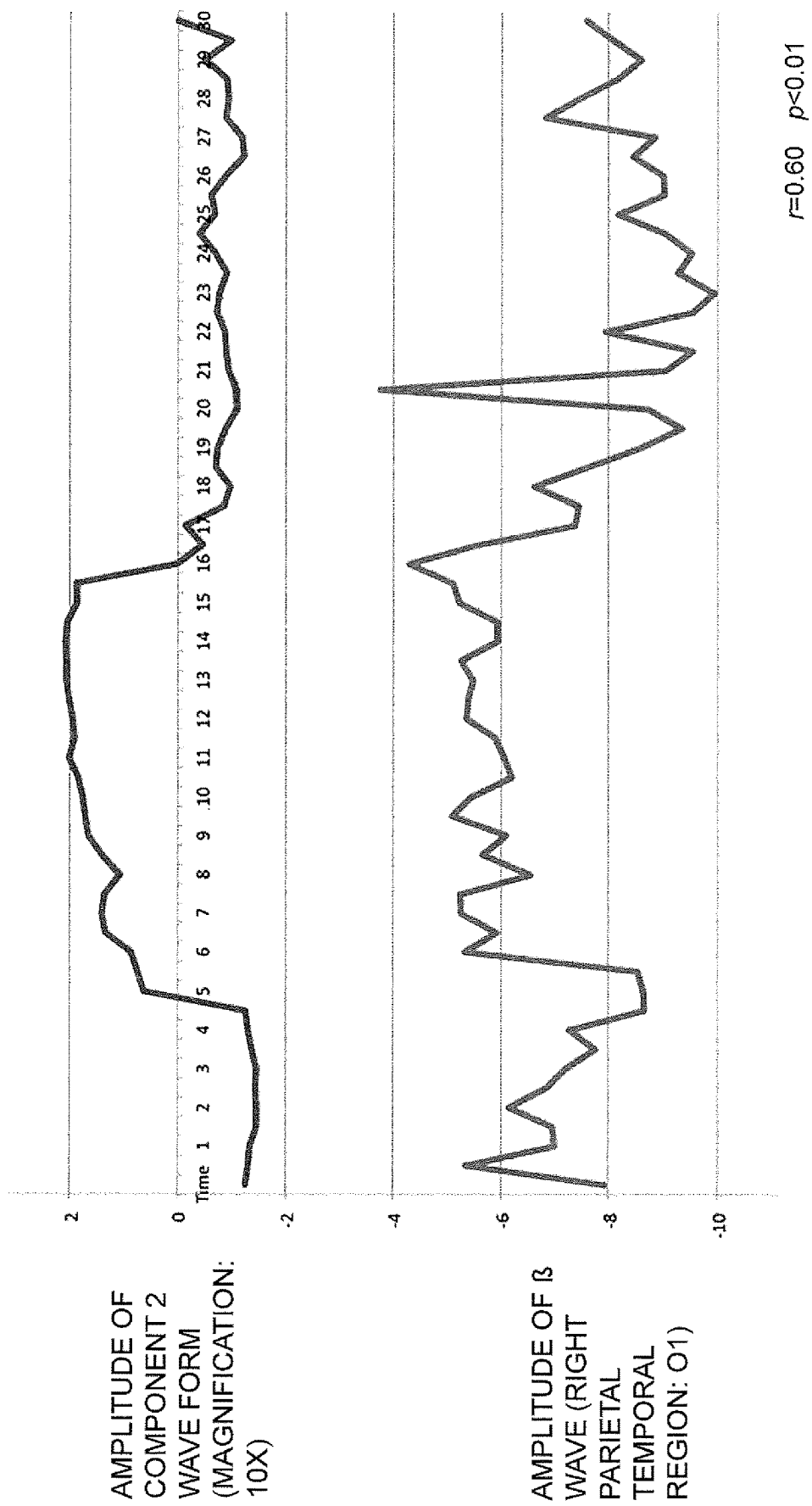
FIG. 16 is a chart illustrating a portion of the results of analyzing a component waveform based on the facial skin temperature data.
Figure 17:
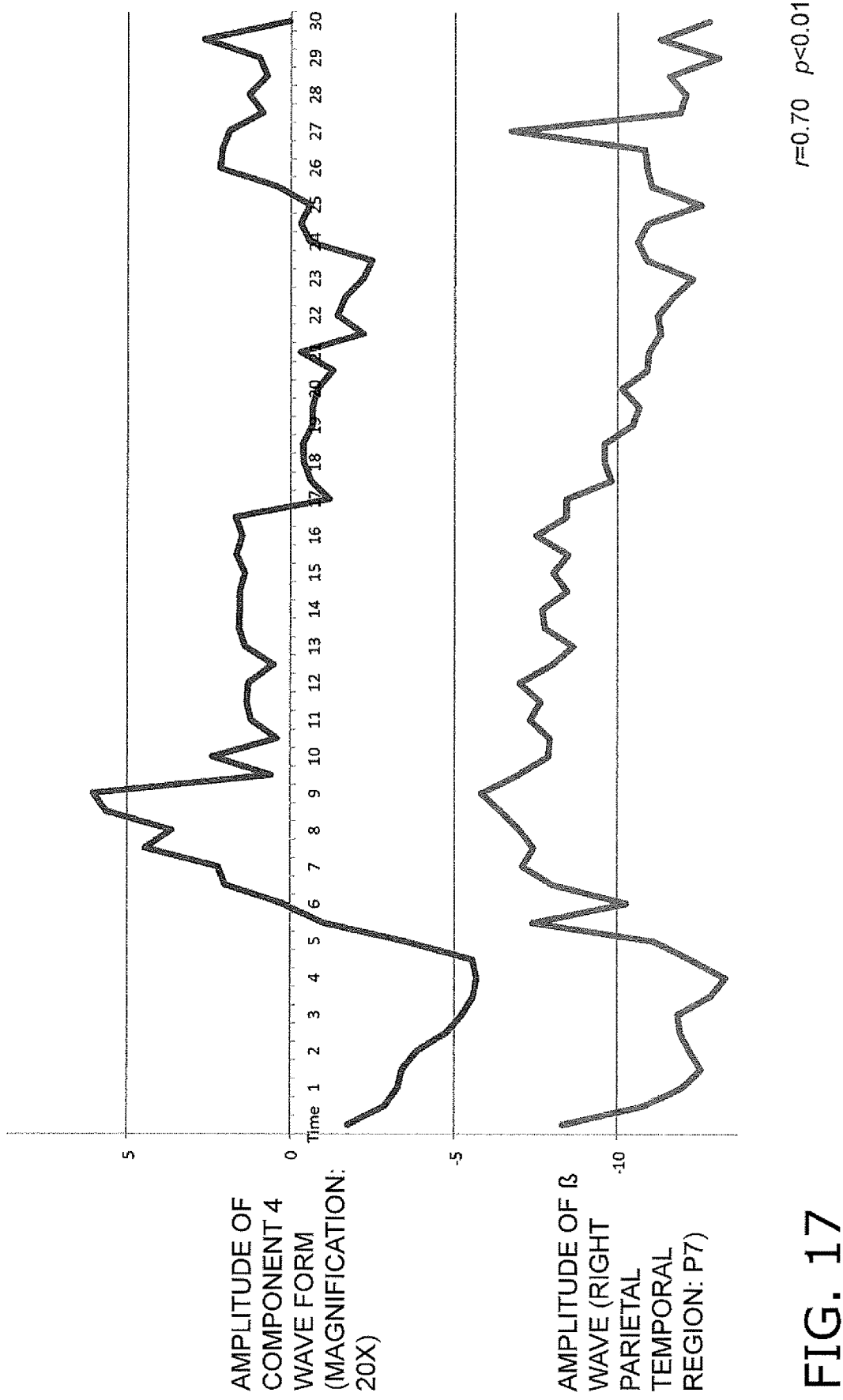
FIG. 17 is a chart illustrating a portion of the results of analyzing a component waveform based on the photographic image data of the facial surface.
Figure 18:
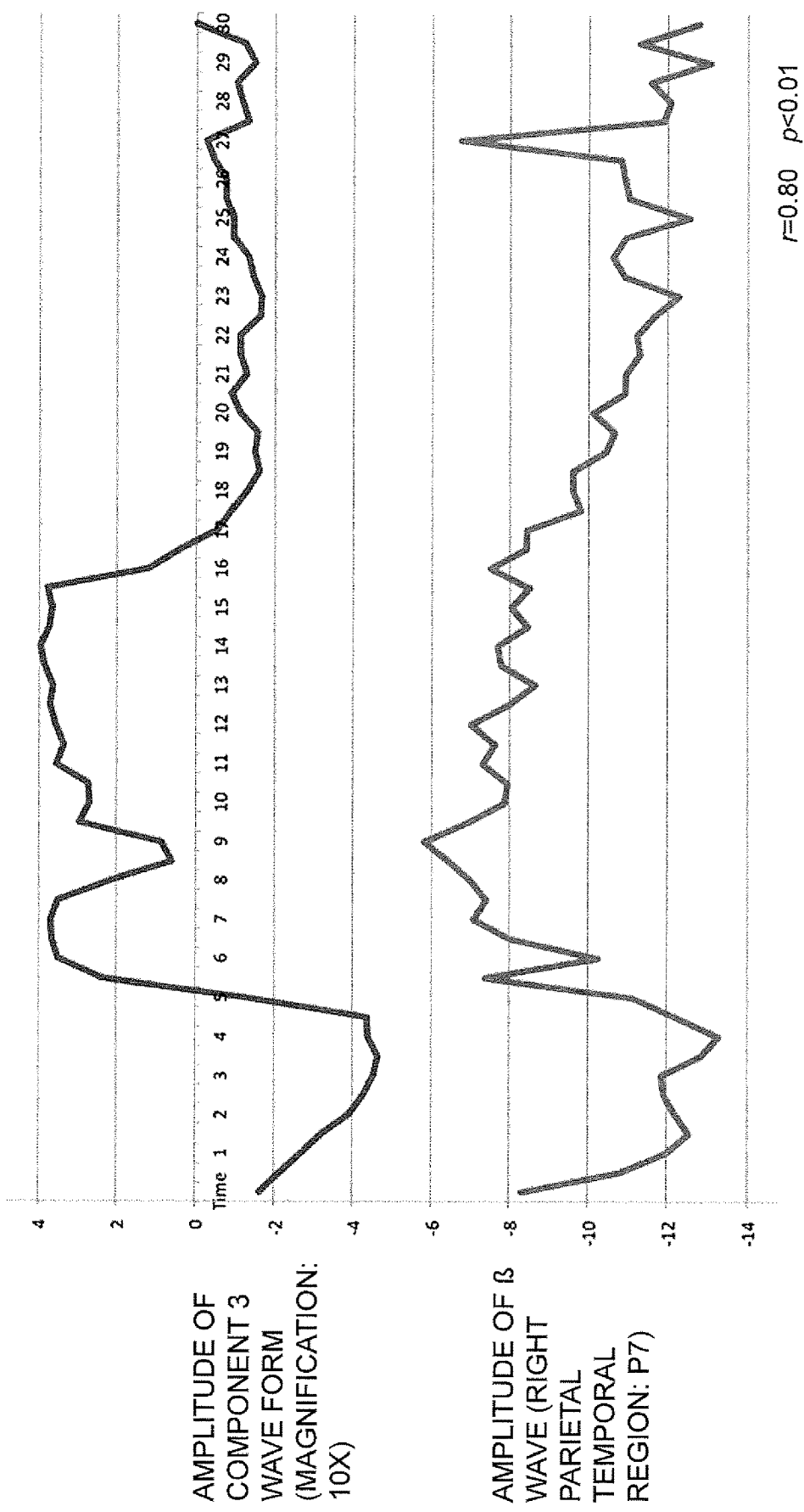
FIG. 18 is a chart illustrating a portion of the results of analyzing a component waveform based on the facial skin temperature data.

FIGS. 7 to 18 illustrate portions of the results of analyzing component waveform diagrams based on the photographic image data of the facial surface (blood circulation volume data) or facial skin temperature data. FIG. 7 illustrates the amplitude of the component waveform of the component 2 based on the photographic image data of the subject 1, and the amplitude of the β wave of the measured brain waves of the subject 1. FIG. 8 illustrates the amplitude of the component waveform of the component 2 based on the facial skin temperature data of the subject 1, and the amplitude of the β wave of the measured brain waves of the subject 1. FIG. 9 illustrates the amplitude of the component waveform of the component 2 based on the photographic image data of a subject 2, and the amplitude of the β wave of the measured brain waves of the subject 2. FIG. 10 illustrates the amplitude of the component waveform of the component 2 based on the facial skin temperature data of the subject 2, and the amplitude of the β wave of the measured brain waves of the subject 2. FIG. 11 illustrates the amplitude of the component waveform of a component 4 based on the photographic image data of a subject 3, and the amplitude of the β wave of the measured brain waves of the subject 3. FIG. 12 illustrates the amplitude of the component waveform of the component 3 based on the facial skin temperature data of the subject 3, and the amplitude of the β wave of the measured brain waves of the subject 3. FIG. 13 illustrates the amplitude of the component waveform of the component 3 based on the photographic image data of a subject 4, and the amplitude of the β wave of the measured brain waves of the subject 4. FIG. 14 illustrates the amplitude of the component waveform of the component 2 based on the facial skin temperature data of the subject 4, and the amplitude of the β wave of the measured brain waves of the subject 4. FIG. 15 illustrates the amplitude of the component waveform of the component 2 based on the photographic image data of a subject 5, and the amplitude of the β wave of the measured brain waves of the subject 5. FIG. 16 illustrates the amplitude of the component waveform of the component 2 based on the facial skin temperature data of the subject 5, and the amplitude of the β wave of the measured brain waves of the subject 5. FIG. 17 illustrates the amplitude of the component waveform of the component 4 based on the photographic image data of a subject 6, and the amplitude of the β wave of the measured brain waves of the subject 6. FIG. 18 illustrates the amplitude of the component waveform of the component 3 based on the facial skin temperature data of the subject 6, and the amplitude of the β wave of the measured brain waves of the subject 6.

As illustrated in FIGS. 7 to 18, from the results of the component waveforms and brain wave analyses, correlation was found between the facial skin temperature and the facial blood circulation volume. In each of the analyses based on the facial skin temperature data and the facial blood circulation volume data, significant correlation was found between the amplitude of each component waveform and the amplitude of the β wave measured by the electrodes attached to the top or back of the head.

Table 2 shows the results of analyzing the photographic image data of the facial surface of each subject.

TABLE 2

| Subject | Correlation in Blood Circulation Volume Data | | Correlation in Relative Conversion Blood Circulation Volume Data | |
|---|---|---|---|---|
| | Component waveform | Blood circulation volume distribution | Component waveform | Blood circulation volume distribution |
| Subject 1 | Component 2 | 0.72 | Component 1 | 0.59 |
| | | | Component 2 | 0.85 |
| Subject 2 | Component 1 | 0.82 | Component 1 | 0.62 |
| | Component 2 | 0.82 | Component 2 | 0.60 |
| Subject 3 | Component 2 | 0.33 | Component 2 | 0.45 |
| | | | Component 3 | 0.56 |
| | Component 3 | 0.31 | Component 4 | 0.56 |
| Subject 4 | Component 1 | 0.57 | Component 1 | 0.66 |
| | Component 3 | 0.71 | Component 3 | 0.65 |
| Subject 5 | Component 1 | 0.56 | Component 1 | 0.51 |
| | Component 2 | 0.72 | Component 2 | 0.83 |
| Subject 6 | Component 2 | 0.38 | Component 2 | 0.45 |
| | | | Component 3 | 0.51 |
| | Component 4 | 0.68 | Component 5 | 0.36 |

As shown in Table 2, from the results obtained by analyzing the photographic image data of the facial surface described above, significant correlation was found between human brain activity and the components 1, 2, 3, 4, and 5 of the plurality of components obtained by decomposing the time-series blood circulation volume data based on the photographic image data of the facial surface by singular value decomposition. Note that, in this case, the components found to have significant correlation based on the blood circulation volume data and significant correlation based on the relative conversion blood circulation volume data were determined to have the significant correlation with human brain activity and, in addition, the components that did not have significant correlation based on the blood circulation volume data but did have significant correlation based on the relative conversion blood circulation volume data were also determined to have the significant correlation with human brain activity.

Table 3 shows the results of the control test.

TABLE 3

| | |
|---|---|
| Components having correlation with brain resting time/brain activated time | Component 1, Component 2 |
| Components having correlation with movement distance of face | Component 1, Component 3, Component 4 |
| Components having correlation with number of keyboard inputs | Component 8 |

As shown in Table 3, in the control test, when the subject moved while the photographic image data of the facial surface was being acquired, some of the components were found to have significant correlation between the amplitude of the component waveform thereof and each of the brain resting time and the brain activated time. Among these components, the component 2 was not found to have significant correlation with movement distance or the number of keyboard inputs. As such, it was confirmed that, among the plurality of components that were obtained by conducting the singular value decomposition the blood circulation volume data based on the RGB data acquired from the photographic image data of the facial surface a component having significant correlation with brain activity could be influenced by the movement of the subject while acquiring the time-series photographic image data of the facial surface, but this influence was much smaller than the influence resulting from the brain activity (the influence resulting from the activation or resting of the brain).

Based on these results, the present inventors made the following findings.

The blood circulation volume data, obtained from the RGB data of the facial surface based on time-series photographic image data of the facial surface acquired from the subjects, was decomposed into the plurality of components by singular value decomposition. As a result of analyzing each of the decomposed components, it was found that the components 1, 2, 3, 4, and 5 of the plurality of components are components that are related to brain activity. Specifically, it was found that it is possible to identify, a component indicating an RGB change in the facial surface that reflects brain activity from the plurality of components, by decomposing the blood circulation volume data, which was obtained from the RGB data of the facial surface based on the time-series photographic image data of the facial surface into the plurality of components, extracting components having correlation with the activation/resting of the brain from the decomposed plurality of components, and analyzing the extracted components. Thus, the present inventors found that it is possible to estimate brain activity on the basis of time-series photographic image data of a human facial surface.

(4) Brain Activity Visualization Device

Next, brain activity visualization devices 10, 110 according to an embodiment of the present invention will be described. The brain activity visualization devices 10, 110 were conceived by the inventor on the basis of the findings described above. The brain activity visualization devices according to the present invention should not be construed as being limited to the following embodiments, and various types of modifications may be made without departing from the spirit or scope of the general inventive concept of the present invention.

The brain activity visualization devices 10, 110 according to the embodiment of the present invention include brain activity estimation means 30 that estimate brain activity on the basis of facial skin temperature data, and/or brain activity estimation means 130 that estimate brain activity on the basis of photographic image data of the facial surface. Before describing the brain activity visualization devices 10, 110 according to the embodiment of the present invention, each of the brain activity estimation means 30, 130 will be described.

Figure 19:
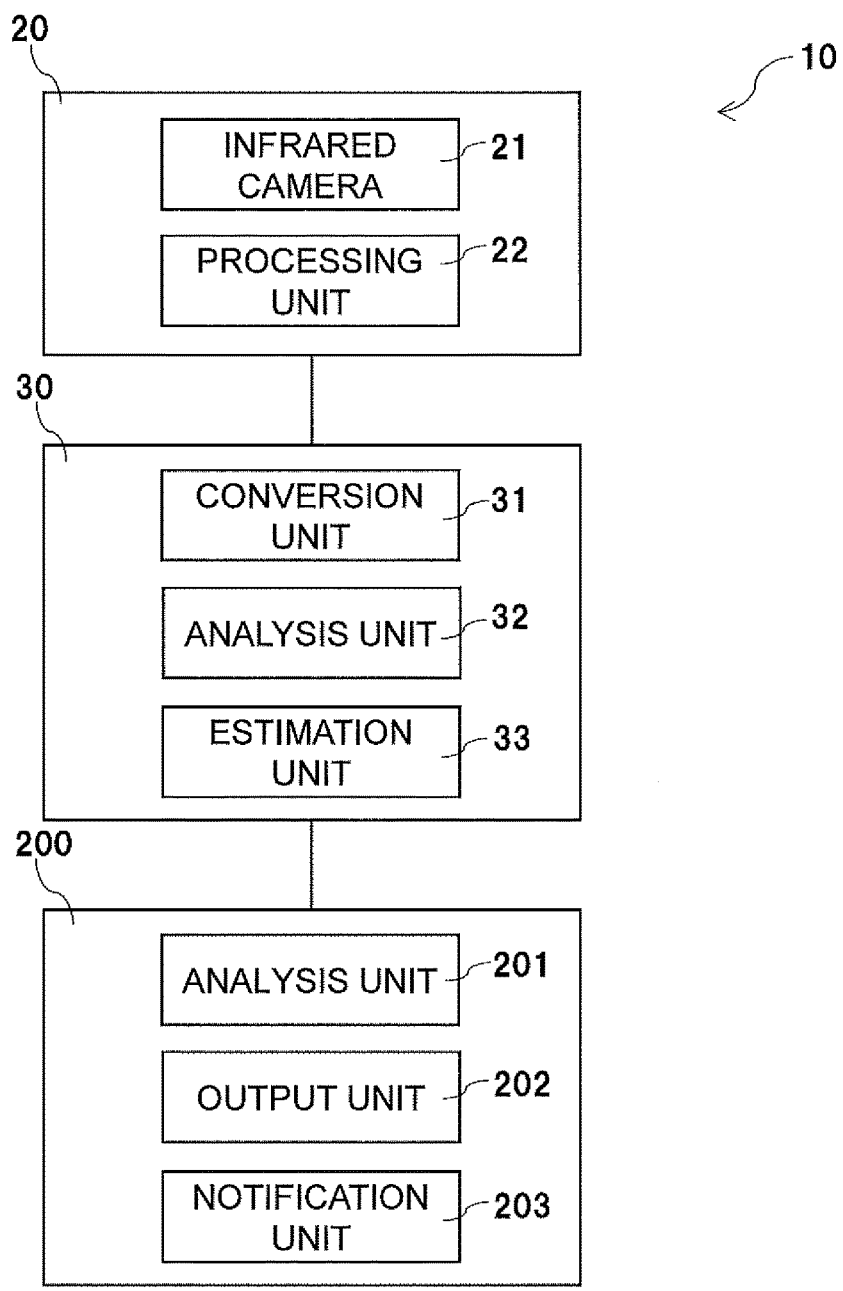
FIG. 19 is a schematic drawing of a brain activity visualization device according to an embodiment of the present invention.
Figure 20:
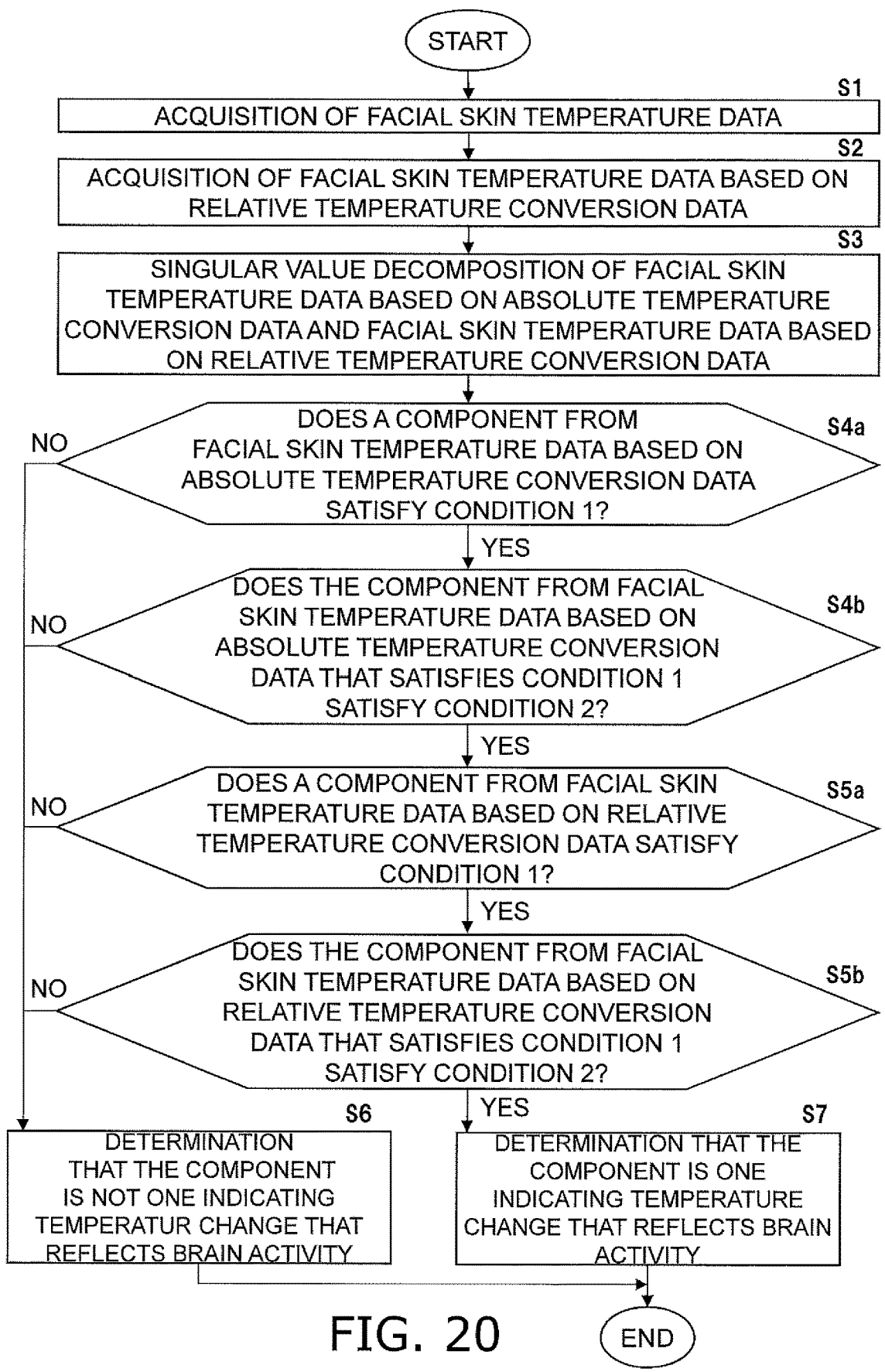
FIG. 20 is a flowchart showing the flow of processing conducted in the brain activity visualization device to identify a component indicating a change in skin temperature that reflects brain function.

(4-1) Brain Activity Estimation Means 30 that Estimate Brain Activity on the Basis of Facial Skin Temperature Data FIG. 19 is a schematic drawing of the brain activity visualization device 10 according to the embodiment of the present invention. FIG. 20 is a flowchart showing the flow of processing conducted in the brain activity visualization device 10 to identify a component indicating a change in skin temperature that reflects brain function.

The brain activity estimation means 30 of the brain activity visualization device 10 estimate the brain activity of an individual (subject) from the facial skin temperature of the individual. As illustrated in FIG. 19, the brain activity visualization device 10 includes facial skin temperature acquisition means 20, the brain activity estimation means 30, and state visualization means 200.

The facial skin temperature acquisition means 20 detect the skin temperature of at least a portion of the facial surface of the individual, and chronologically acquire facial skin temperature data including detected temperature data and position data of the detection site (step S1). Note that, in this case, the facial skin temperature acquisition means 20 is an infrared thermography device and includes an infrared camera 21 and a processing unit 22 as illustrated in FIG. 19. The infrared camera 21 is configured to detect infrared radiant energy emitted from the facial surface of the individual. Moreover, in this case, the infrared camera 21 is configured to detect infrared radiant energy emitted from the entire facial surface of the individual. The processing unit 22 converts the infrared radiant energy detected by the infrared camera 21 to temperatures to create temperature data. The processing unit 22 generates a temperature distribution diagram of the facial skin temperature of the entire facial surface, for which the sites where the infrared radiant energy was detected are used as the position data (coordinate data). The processing unit 22 processes the generated temperature distribution diagram as facial skin temperature data based on temperature conversion data. The processing unit 22 has a storage unit (not illustrated in the drawings) and the facial skin temperature data based on temperature conversion data is stored in this storage unit.

An example is described in which the temperature distribution diagram of the facial skin temperature of the whole facial surface is generated in the processing unit 22, but the present invention is not limited thereto. For example, a configuration is possible in which a temperature distribution diagram of facial skin temperature including at least the forehead and/or the area around the paranasal sinuses is generated and used as the facial skin temperature data based on temperature conversion data.

Additionally, in this case, a brain function activation task is given to the individual for a set period of time while the facial skin temperature acquisition means 20 are acquiring the facial skin temperature data based on temperature conversion data. That is, the facial skin temperature data based on temperature conversion data, acquired by the facial skin temperature acquisition means 20, contains data for a period in which the brain function activation task was being given to the individual. Note that the brain function activation task given to the individual is not particularly limited provided that the task is presumed to place the brain in an activated state, and the content thereof may be appropriately determined in accordance with the purpose of use of the brain activity visualization device 10.

The brain activity estimation means 30 estimate human brain activity on the basis of facial skin temperature data based on the temperature conversion data acquired by the facial skin temperature acquisition means 20. Specifically, the brain activity estimation means 30 include a conversion unit 31, an analysis unit 32, and an estimation unit 33 as illustrated in FIG. 19.

The conversion unit 31 converts the temperature data included in the facial skin temperature data based on temperature conversion data to relative temperature data, and generates facial skin temperature data based on the converted relative temperature data, that is, facial skin temperature data based on relative temperature conversion data (step S2). Specifically, the conversion unit 31 uses, as a reference, an average of the temperature data included in the facial skin temperature data based on temperature conversion data for every predetermined time period (e.g. 30 seconds), and converts the temperature data to relative temperature data. Then, the conversion unit 31 uses the converted relative temperature data and the position data to generate the facial skin temperature data based on relative temperature conversion data.

The analysis unit 32 decomposes each of the time-series facial skin temperature data based on temperature conversion data and the facial skin temperature data based on relative temperature conversion data into a plurality of components by singular value decomposition, principal component analysis, or independent component analysis (step S3). Here, the analysis unit 32 subjects each of the acquired facial skin temperature data based on temperature conversion data and the facial skin temperature data based on relative temperature conversion data to singular value decomposition in which the SVD of MATLAB (registered trademark) is used as the analysis tool. In the singular value decomposition, for each of the chronologically acquired facial skin temperature data based on temperature conversion data and the facial skin temperature data based on relative temperature conversion data, the factor is set to time data per predetermined time period (e.g. 30 seconds), and the measure is set to the facial skin temperature data based on temperature conversion data and the facial skin temperature data based on relative temperature conversion data in each time period. Then, the facial skin temperature data based on temperature conversion data and the facial skin temperature data based on relative temperature conversion data are each decomposed into a plurality of components by singular value decomposition. Thereafter, the analysis unit 32 calculates a time distribution, a space distribution, and a singular value representing the magnitude of each component.

Additionally, the analysis unit 32 determines whether or not each component satisfies a first condition and a second condition in order to identify a component, from the plurality of components decomposed by singular value decomposition, indicating a change in skin temperature that reflects brain activity (step S4*a*, step S4*b*, step S5*a*, and step S5*b*). Note that, in this case, the analysis unit 32 first determines whether or not each component from the facial skin temperature data based on temperature conversion data satisfies the first condition (step S4*a*). Then, for components from the facial skin temperature data based on temperature conversion data determined to satisfy the first condition in step S4*a*, the analysis unit 32 determines whether or not those components satisfy the second condition (step S4*b*). Then, the analysis unit 32 determines whether or not each component from the facial skin temperature data based on relative temperature conversion data, matching the components determined to satisfy the first condition and the second condition in step S4*a* and step S4*b*, satisfies the first condition (step S5*a*). Then, the analysis unit 32 determines whether or not the components from the facial skin temperature data based on relative temperature conversion data, which is determined to satisfy the first condition in step S5*a* satisfy the second condition (step S5*b*). However, the order of determination in the analysis unit 32 is not limited thereto and, for example a configuration is possible in which it is determined whether or not the components from the facial skin temperature data based on temperature conversion data and the components from the facial skin temperature data based on relative temperature conversion data satisfy the first condition and the second condition respectively, and the components for which the determination results match are ultimately extracted.

The first condition is that the amplitude of the component waveform of the component decomposed by singular value decomposition has correlation with changes at brain resting time and brain activated time. The analysis unit 32 extracts, from the plurality of components, components satisfying the first condition as determination components. Note that, the brain function activation task is given to the individual for a set period of time while the facial skin temperature data based on temperature conversion data is being acquired. The brain resting time is defined as the period in which the brain function activation task is not being given to the individual, and the brain activated time is defined as the period in which the brain function activation task is being given to the individual. Here, the analysis unit 32 conducts a comparative analysis of the component waveform of each component against the periods in which the brain function activation task is and is not being given. Using the results of this comparative analysis based on the component waveform data, the analysis unit 32 evaluates whether or not there is correlation between the component waveform of each component and each of the brain resting time and the brain activated time. Then, the analysis unit 32 extracts, from the plurality of components, components evaluated as having correlation as a determination component that satisfies the first condition. Meanwhile, the analysis unit 32 determines that, among the plurality of components, a component evaluated as not having correlation is the component that does not satisfy the first condition and is not the component indicating a temperature change that reflects human brain activity (step S6).

In this case, the brain function activation task is given to the individual for a set period of time while acquiring the facial skin temperature data based on temperature conversion data, and the analysis unit 32 extracts the determination components based thereon. However, the content of the first condition, that is, the means of extracting the determination component by the analysis unit 32, is not limited thereto. For example, when the components, among the plurality of components, indicating a component waveform that has correlation with the brain resting time and the brain activated time are already identified by previous experiments or the like, the analysis unit 32 may extract these identified components from the plurality of components as the determination components. Additionally, with this brain activity visualization device, in cases where human behavior, which is known to be related to the activation/resting of the brain such as eye movement and blinking are detected, the analysis unit 32 may extract the determination components from the plurality of components by comparing and analyzing the detection results against the component waveform of each component and conducting an evaluation. Note that the criterion for the analysis unit 32 to determine whether or not the first condition is satisfied is appropriately decided by simulations, experiments, theoretical calculations, or the like, in accordance with the purpose of use of the brain activity visualization device 10 or the like.

The second condition is that there is a temperature change at the predetermined site on the human facial surface in the extracted determination components. The analysis unit 32 determines that, among the determination components, the components that satisfy the second condition have a high potential of being related to human brain activity, and extracts these as candidate components. That is, the analysis unit 32 determines whether or not the determination components are related to human brain activity on the basis of the presence/absence of a temperature change at the predetermined site on a human facial surface. Specifically, the analysis unit 32 determines whether or not temperature change has occurred at the forehead and/or the area around the paranasal sinuses on the basis of the temperature distribution data of the extracted determination components. When a temperature change has occurred, the analysis unit 32 determines that there is a high possibility that the determination component satisfies the second condition and is related to human brain activity, and extracts that determination component as a candidate component. Meanwhile, when a temperature change has not occurred at the forehead or the area around the paranasal sinuses, the analysis unit 32 determines that the determination component does not satisfy the second condition and is not a component indicating a skin temperature change that reflects human brain activity (step S6). Note that the criterion for the analysis unit 32 to determine whether or not the second condition is satisfied is appropriately decided by simulations, experiments, theoretical calculations, or the like, in accordance with the purpose of use of the brain activity visualization device 10.

Then, the analysis unit 32 identifies the component which is determined to satisfy the second condition in step S5b, as a component indicating a change in skin temperature that reflects brain activity (step S7). That is, the component identified in step S7 as the component indicating a change in skin temperature that reflects brain activity is a component that is present in both the candidate components extracted by decomposing and analyzing the facial skin temperature data based on temperature conversion data by singular value decomposition and the candidate components extracted by decomposing and analyzing the facial skin temperature data based on relative temperature conversion data by singular value decomposition. Note that, the candidate components for which both analyses do not match are determined that they are not the components indicating a change in skin temperature that reflects brain activity in step S6.

The estimation unit 33 estimates human brain activity on the basis of the component identified by the analysis unit 32 as a component indicating a change in skin temperature that reflects human brain activity. Specifically, the estimation unit 33 estimates an amount of brain activity when acquiring the facial skin temperature data on the basis of the component waveform data of the component identified by the analysis unit 32.

(4-1-1) Modification Example 1A

The brain activity estimation means 30 described above includes the conversion unit 31, and the facial skin temperature data based on relative temperature conversion data is generated by the conversion unit 31. Moreover, the analysis unit 32 uses singular value decomposition to decompose, into a plurality of components, not only the facial skin temperature data based on temperature conversion data acquired by the facial skin temperature acquisition means 20, but also the facial skin temperature data based on relative temperature conversion data, which is from the temperature data that has been converted into relative temperature data. Then, the analysis unit 32 analyzes each of the components.

Instead of this, a configuration in which the brain activity estimation means 30 does not include the conversion unit 31 can be adopted. In this case, the processes for generating the facial skin temperature data based on relative temperature conversion data and analyzing the data from the facial skin temperature data based on relative temperature conversion data can be omitted.

However, in order to accurately identify the component related to human brain activity, it is preferable that the brain activity estimation means 30 include the conversion unit 31, as in the embodiment described above. Moreover, it is desirable that the analysis unit 32 conducts singular value decomposition to decompose, into a plurality of components, not only the facial skin temperature data based on temperature conversion data acquired by the facial skin temperature acquisition means 20, but also the facial skin temperature data based on relative temperature conversion data, which is from the temperature data that has been converted into relative temperature data; and analyzes each of the components.

(4-1-2) Modification Example 1B

The facial skin temperature acquisition means 20 described above is an infrared thermography device capable of acquiring temperature data in a state of non-contact with the subject.

However, the facial skin temperature acquisition means are not particularly limited to an infrared thermography device, provided that the facial skin temperature acquisition means are capable of detecting the skin temperature of at least a portion of the facial surface of the individual, and chronologically acquiring facial skin temperature data including detected temperature data and position data of the detection site.

For example, the facial skin temperature acquisition means may be a device that includes temperature sensors. Specifically, a configuration is possible in which the temperature sensors are applied to predetermined sites on the facial surface of the individual, and the time-series facial skin temperature data is acquired on the basis of temperature data detected by the temperature sensors and the position data of the sites where the temperature sensors are applied. Even in cases where the facial skin temperature data is acquired while the temperature sensors are in contact with the individual, namely the subject, there is no need to treat the temperature sensors prior to application, unlike a case in which electroencephalogram electrodes or the like are used. As a result, data can be acquired more easily compared to conventional detection methods such as electroencephalography, functional magnetic resonance imaging, and near infrared spectroscopy. As such, human brain activity can be easily estimated.

Figure 21:
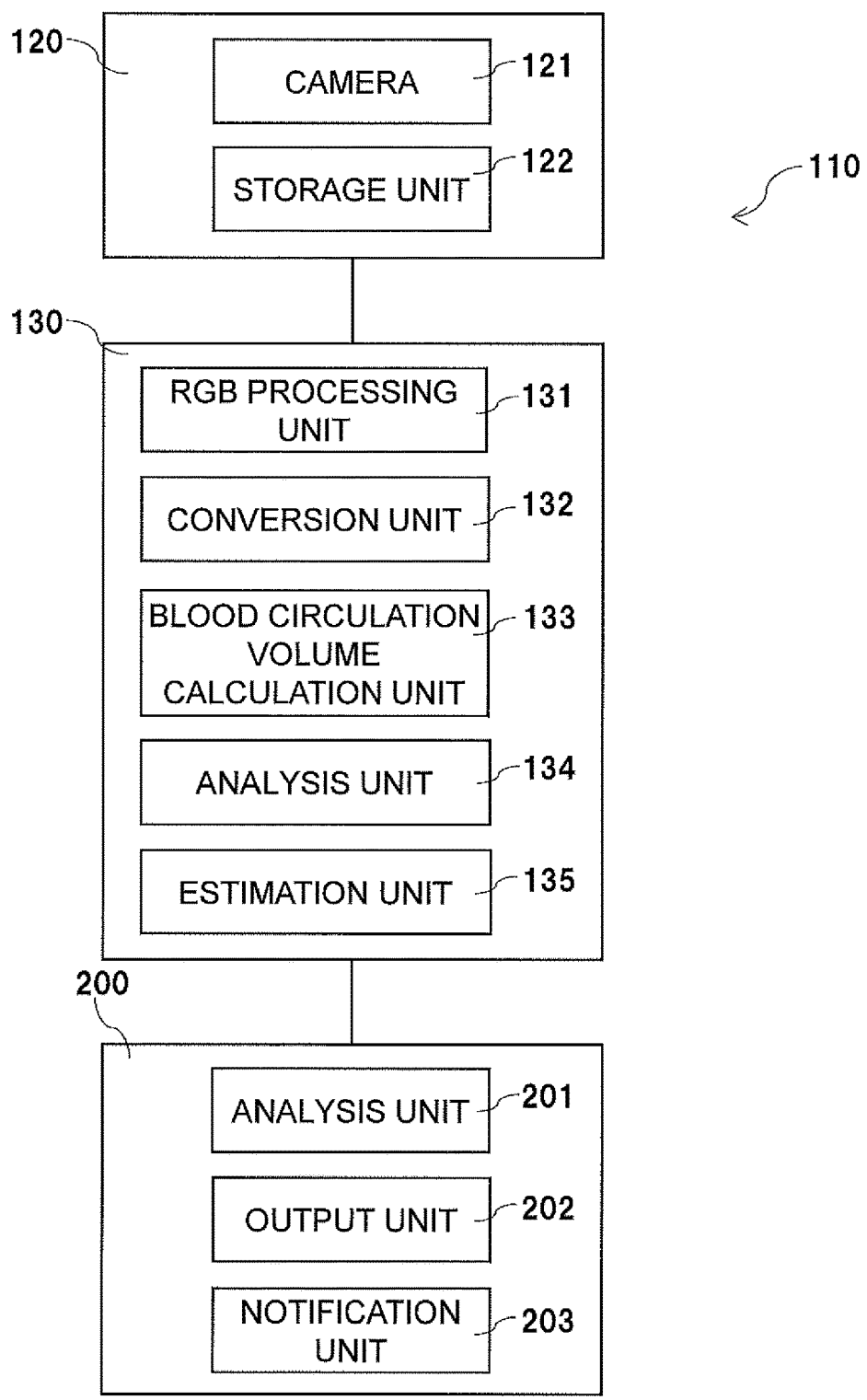
FIG. 21 is a schematic drawing of a brain activity visualization device according to an embodiment of the present invention.
Figure 22:
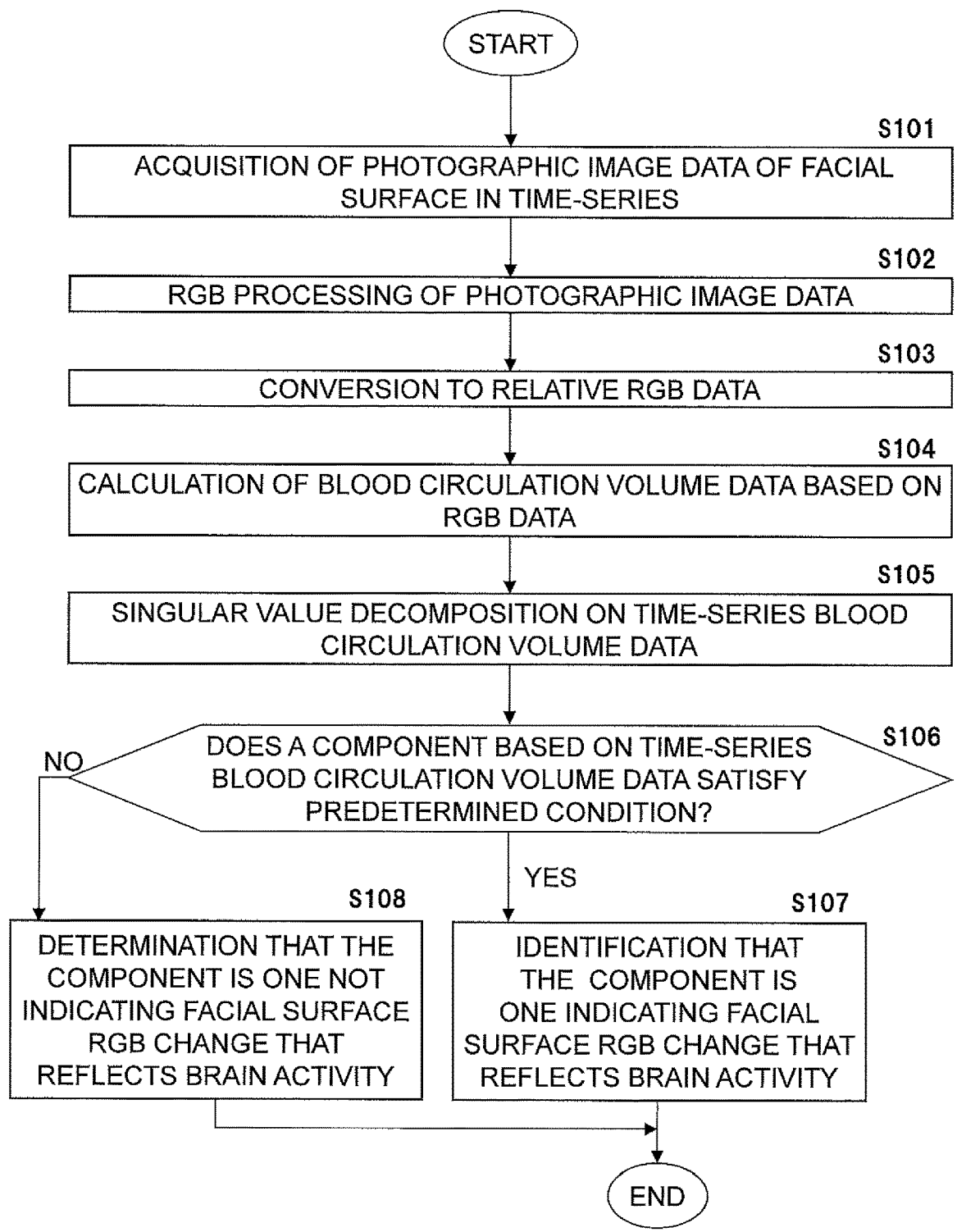
FIG. 22 is a flowchart showing an example of the flow of processing conducted in the brain activity visualization device to identify a component indicating an RGB change in the facial surface that reflects brain function.

(4-2) Brain Activity Estimation Means 130 that Estimate Brain Activity on the Basis of Photographic Image Data of Facial Surface FIG. 21 is a schematic drawing of the brain activity visualization device 110 according to the embodiment of the present invention. FIG. 22 is a flowchart showing an example of the flow of processing conducted in the brain activity visualization device 110 to identify a component indicating an RGB change in the facial surface that reflects brain function.

The brain activity estimation means 130 of the brain activity visualization device 110 estimate the brain activity of an individual (subject) from the photographic image data of the facial surface of the individual. As illustrated in FIG. 21, the brain activity visualization device 110 includes image data acquisition means 120, brain activity estimation means 130, and state visualization means 200.

The image data acquisition means 120 chronologically acquire photographic image data of at least a portion of the facial surface of the individual (step S101). Note that the image data acquisition means 120 are not particularly limited provided that they at least include an imaging device, and examples thereof include smartphones, tablets (e.g. iPad (registered trademark)), and other portable terminals with built in imaging devices. In this case, as illustrated in FIG. 21, the image data acquisition means 120 include a storage unit 122 and a camera 121 as the imaging device. The camera 121 is configured to chronologically acquire photographic image data of the facial surface of the individual. In this case, the camera 121 captures video of the entire facial surface of the individual and acquires the captured video data. The time-series photographic image data captured by the imaging device is stored in the storage unit 122. In this case, the video data acquired by the camera 121 is stored in the storage unit 122.

Note that, in this case, the camera 121 captures video of the entire facial surface, but the present invention is not limited thereto. For example, a configuration is possible in which the camera 121 captures video including images of at least the forehead and/or the area around the paranasal sinuses of the face.

Additionally, in this case, the brain function activation task is given to the individual for a set period of time while the image data acquisition means 120 are acquiring the time-series photographic image data of the facial surface. That is, the photographic image data acquired by the image data acquisition means 120 contains data for a period in which the brain function activation task is being given to the individual. Note that the brain function activation task given to the individual is not particularly limited provided that the task is presumed to place the brain in an activated state, and the content thereof may be appropriately determined in accordance with the purpose of use of the brain activity visualization device 110.

The brain activity estimation means 130 estimate human brain activity on the basis of the time-series photographic image data on the facial surface acquired by the image data acquisition means 120. Specifically, the brain activity estimation means 130 include an RGB processing unit 131, a conversion unit 132, a blood circulation volume calculation unit 133, an analysis unit 134, and an estimation unit 135 as illustrated in FIG. 21. Note that, in FIG. 21, a configuration is illustrated in which the brain activity estimation means 130 are a single device including the RGB processing unit 131, the conversion unit 132, the blood circulation volume calculation unit 133, the analysis unit 134, and the estimation unit 135. However, the present invention is not limited thereto and configurations are possible in which some or all of the RGB processing unit 131, the conversion unit 132, the blood circulation volume calculation unit 133, the analysis unit 134, and the estimation unit 135 are provided as independent devices. Additionally, in this case, facial blood circulation volume acquisition means are configured from the image data acquisition means 120, the RGB processing unit 131, the conversion unit 132, and the blood circulation volume calculation unit 133.

The RGB processing unit 131 performs RGB processing on the photographic image data acquired by the image data acquisition means 120 to decompose the photographic image data into three color components, namely an R component, a G component, and a B component (step S102). The RGB processing may be performed on the photographic image data of the entire facial surface but, in this case, the data of the forehead and/or area around the paranasal sinuses is extracted from the photographic image data and the RGB processing is performed on the extracted data in order to reduce computation load and noise.

The conversion unit 132 converts RGB data of the photographic image data obtained by the RGB processing to relative RGB data (step S103). Specifically, the conversion unit 132 uses, as a reference, an average of the RGB data obtained from the photographic image data for every predetermined time period (e.g. 30 seconds) to convert the RGB data to relative RGB data.

The blood circulation volume calculation unit 133 calculates time-series blood circulation volume data of the facial surface on the basis of the RGB data of the photographic image data obtained by the RGB processing (step S104).

The analysis unit 134 decomposes the time-series relative conversion blood circulation volume data into a plurality of components by singular value decomposition, principal component analysis, or independent component analysis (step S105). Here, the analysis unit 134 subjects each of the relative conversion blood circulation volume data to singular value decomposition in which the SVD of MATLAB (registered trademark) is used as the analysis tool. Specifically, in the singular value decomposition, for the time-series relative conversion blood circulation volume data, the factor is set to time data per predetermined time period (e.g. 30 seconds), and the measure is set to the relative conversion blood circulation volume data per pixel, as calculated from the relative RGB data at each time period. Then, the time-series relative conversion blood circulation volume data is decomposed into a plurality of components by singular value decomposition and a time distribution, a space distribution, and a singular value representing the magnitude of each component is calculated.

Additionally, the analysis unit 134 determines whether or not each component satisfies predetermined conditions in order to identify a component, from the plurality of components decomposed by the singular value decomposition, indicating an RGB change in the facial surface that reflects brain activity (step S106). The predetermined condition includes conditions such as, for example, that the amplitude of the component waveform of the component decomposed by singular value decomposition has correlation with changes at brain resting time and brain activated time (hereinafter referred to as "first condition"), and/or that there is a blood circulation volume change at a predetermined site on the human facial surface in the component decomposed by the singular value decomposition (hereinafter referred to as "second condition"). One or a plurality of conditions may be set as the predetermined condition determined by the analysis unit 134. In this case, the first condition is set as the predetermined condition.

Then, the analysis unit 134 extracts, from the plurality of components, a component that satisfies the predetermined condition as a determination component. Furthermore, the analysis unit 134 identifies, from the extracted determination components, components that satisfy all of the conditions included in the predetermined condition as components indicating an RGB change in the facial surface that reflects brain activity (step S107). Meanwhile, the analysis unit 134 determines that the components among the plurality of components that do not satisfy one or more of the conditions included in the predetermined condition are not components indicating an RGB change in the facial surface that reflects brain activity (step S108).

In this case, as described above, only one condition is set as the predetermined condition, and the brain function activation task is given to the individual for a set period of time while the time-series photographic image data is being acquired. Therefore, the brain resting time is defined as the period of time in which the brain function activation task is not being given to the individual, and the brain activated time is defined as the period of time in which the brain function activation task is being given to the individual. The analysis unit 134 conducts a comparative analysis of the component waveform of each component against the periods of time in which the brain function activation task is and is not being given. Using the results of this comparative analysis based on the component waveform data, the analysis unit 134 evaluates whether or not there is correlation between the component waveform of each component and each of the brain resting time and the brain activated time. Then, the analysis unit 134 extracts, from the plurality of components, a component evaluated as having correlation as a determination component that satisfies the predetermined condition. The analysis unit 134 identifies this determination component as a component indicating an RGB change in the facial surface that reflects brain activity. Meanwhile, the analysis unit 134 determines that, among the plurality of components, a component evaluated as not having correlation is the component that does not satisfy the predetermined condition, and is not the component indicating an RGB change in the facial surface that reflects human brain activity.

In this case, the brain function activation task is given to the individual for a set period of time while acquiring the time-series photographic image data of the facial surface, and the analysis unit 134 extracts the determination component on the basis thereof. However, the content of the first condition, that is, the means of extracting the determination component by the analysis unit 134, is not limited thereto. For example, when the component, among the plurality of components, indicating the component waveform that has correlation with the brain resting time and the brain activated time is already identified by previous experiments or the like, the analysis unit 134 extracts this identified component from the plurality of components as the determination component. Additionally, with the brain activity visualization device 110, in cases where human behavior, which is known to be related to the activation/resting of the brain such as eye movement and blinking are detected, the analysis unit 134 may extract the determination component from the plurality of components by comparing and analyzing these detection results against the component waveform of each component and conducting an evaluation. Note that the criterion for the analysis unit 134 to determine whether or not the first condition is satisfied is appropriately decided by simulations, experiments, theoretical calculations, or the like, in accordance with the purpose of use of the brain activity visualization device 110 or the like.

Additionally, in cases where the second condition is set as the predetermined condition, the analysis unit 134 extracts the determination component on the basis of the presence/absence of a change in facial blood circulation volume at the predetermined site on the human facial surface. Specifically, the analysis unit 134 determines whether or not a change in the blood circulation volume has occurred at the forehead and/or the area around the paranasal sinuses, on the basis of the blood circulation volume distribution diagrams corresponding to the plurality of components decomposed by singular value decomposition. When a change in the blood circulation volume has occurred, the analysis unit 134 determines that said component satisfies the second condition. Meanwhile, when a change in the blood circulation volume has not occurred at the forehead or the area around the paranasal sinuses, the analysis unit 134 determines that said component does not satisfy the second condition. Note that the criterion for the analysis unit 134 to determine whether or not the second condition is satisfied is appropriately determined by simulations, experiments, theoretical calculations, or the like, in accordance with the purpose of use of the brain activity visualization device 110 or the like.

Furthermore, in cases where the blood circulation volume calculation unit 133 calculates the time-series blood circulation volume data based on the RGB data prior to being converted to the relative RGB data, a configuration is possible in which the analysis unit 134 determines whether or not the first condition and/or the second condition is satisfied and extracts a determination component from the plurality of components obtained by subjecting the blood circulation volume data to singular value decomposition or the like.

The estimation unit 135 estimates human brain activity on the basis of the component identified by the analysis unit 134 as a component indicating an RGB change in the facial surface that reflects human brain activity. Specifically, the estimation unit 135 estimates an amount of brain activity when acquiring the photographic image data of the facial surface, on the basis of the component waveform data of the component identified by the analysis unit 134.

(4-2-1) Modification Example 2A

As described above, smartphones, tablets (e.g. iPad (registered trademark)), and other portable terminals with built in imaging devices may be used as the camera 121. In other words, any device that captures images in the visible light region can be used for the photographic image data described above.

Additionally, in the blood circulation volume calculation unit 133, the blood circulation volume data of the facial surface may be calculated using mainly the R component of each pixel included in the RGB data. Provided that the blood circulation volume data can be calculated on the basis of the RGB data, the blood circulation volume data need not be limited to the erythema index.

(4-2-2) Modification Example 2B

The blood circulation volume calculation unit 133 described above calculates the relative conversion blood circulation volume data on the basis of relative RGB data converted by the conversion unit 132. However, in place of or in addition to this, the blood circulation volume calculation unit 133 may calculate the blood circulation volume data on the basis of RGB data prior to being converted to relative RGB data. Components having correlation with brain activity are more likely to be identified (statistical power is high) in blood circulation volume data calculated on the basis of RGB data prior to being converted to relative RGB data. As such, the blood circulation volume data calculated on the basis of RGB data prior to being converted to relative RGB data may be analyzed prior to the relative conversion blood circulation volume data calculated on the basis of relative RGB data. Additionally, a configuration is possible in which the blood circulation volume data is analyzed and components having significant correlation are extracted first and, then, only the components of the relative conversion blood circulation volume data that correspond to the extracted components are analyzed. In this case, computation load can be reduced.

(4-2-3) Modification Example 2C

In the description given above, the camera 121 was assumed to be a typical visible light range camera, but an infrared camera may also be used. In such cases, the infrared camera captures images by emitting infrared light and capturing the reflected waves thereof. The photographic image data of changes in the facial surface of the subject may be obtained in this manner. The present inventors found that there is correlation between the blood circulation volume data calculated from the photographic image data obtained from the reflection of the infrared light and the blood circulation volume data calculated using mainly the R component of each pixel included in the RGB data captured in the visible light region. Accordingly, it is also possible to estimate human brain activity using photographic image data obtained from the reflection of such infrared light.

(4-2-4) Modification Example 2D

Although in the above-mentioned description the brain activity visualization device 110 includes the image data acquisition means 120 and the brain activity estimation means 130, the brain activity visualization device according to the present embodiment is not limited to such a configuration. That is, the brain activity visualization device according to the present embodiment may have any configuration, as long as it includes the blood circulation volume calculation unit 133, the analysis unit 134, and the estimation unit 135. Specifically, the brain activity visualization device according to the present embodiment may take a form, including not only a form in which the device itself generates the image data by photographing, but also a form in which photographic image data is received from an external device to analyze it therein.

(4-3) State Visualization Means 200

The state visualization means 200 displays and visualizes the physiological state of the subject on the basis of the brain activity of the subject estimated by the brain activity estimation means 30 and/or the brain activity estimation means 130. In one example, the state visualization means 200 may include an analysis unit 201 that analyzes changes in the amount of brain activity of the subject in order to analyze the physiological state of the subject. Specifically, the analysis unit 201 determines the physiological state of the subject by analyzing changes in the amount of brain activity in response to stimulation (e.g. visual stimulation, auditory stimulation, tactile stimulation, olfactory stimulation, or taste stimulation) applied to the subject. Note that, the type and level of the physiological state may be appropriately configured in accordance with the use of the brain activity visualization devices 10, 110, on the basis of a degree of rise and/or duration of the amount of brain activity. Moreover, the state visualization means 200 has a display unit 202 that outputs the physiological state of the subject analyzed by the analysis unit 201. As a result, an administrator can ascertain the physiological state of the subject. The display unit 202 is not particularly limited, as long as it can visualize information related to the analyzed physiological state of the subject to the administrator. Examples thereof include display devices that display images, messages, and the like.

Additionally, in cases where acquiring various types of time-series data using the facial skin temperature acquisition means 20 and/or the image data acquisition means 120 after the analysis units 32, 134 have identified the components that reflect brain activity, the additionally acquired various types of data is decomposed into a plurality of components by singular value decomposition in the brain activity visualization devices 10, 110, and only the identified components are analyzed. As a result, the physiological state of the subject can be ascertained in real time.

There are techniques for acquiring heart rate information, biological information, and so on of the subject from the skin temperature or captured images of the facial surface of the subject. In addition, conventional techniques can be applied to the components obtained by performing the singular value decomposition or the like on the various data obtained from the facial skin temperature acquisition means 20 and/or the image data acquisition means 120. As such, heart rate information, biological information, or the like can be accurately acquired. Accordingly, a configuration is possible in which the analysis unit 32 and/or the analysis unit 134 is provided with a feature for analyzing the plurality of components obtained from the singular value decomposition and acquiring heart rate information, biological information, or the like, and the estimation units 33, 135 of the embodiment described above are provided with features for estimating functions of the sympathetic nervous system/parasympathetic nervous system on the basis of the acquired heart rate information and/or biological information.

(5) Features 5-1

In the present embodiment, human brain activity is estimated on the basis of the time-series facial skin temperature data and/or facial blood circulation volume data acquired by the facial skin temperature acquisition means 20 and/or the image data acquisition means 120. As such, human brain activity can be estimated without using electroencephalogram electrodes or other sensors that require pretreatment before being applied. Accordingly, human brain activity can be easily estimated and the physiological state of the subject can be visualized on the basis of the estimated brain activity.

5-2

In cases where a situation is created in which the human brain is placed in states of activation and rest by actually giving and withholding the brain function activation task to a human while the time-series facial skin temperature data and/or the image data is being acquired, it can be said that there is a high possibility that the component having correlation between the component waveform of each component and the brain activated time and the brain resting time is a component indicating a change in skin temperature and/or blood circulation volume that reflects brain activity.

In the present embodiment, the brain function activation task is given to the individual for a certain period of time while the facial skin temperature acquisition means 20 and/or the image data acquisition means 120 is acquiring the time-series facial skin temperature data and/or the image data. That is, in the present embodiment, the brain function activation task is actually given to and withheld from the individual and, as a result, a situation is created in which the human brain is placed in an activated state and a resting state. Moreover, the various time-series data thusly acquired is decomposed into a plurality of components by the singular value decomposition, each component is evaluated whether there is correlation between the component waveform thereof and the brain activated time and the brain resting time, and a component evaluated as having correlation is extracted from the plurality of components as the determination component. Thus, compared, for example, to a case in which a predetermined component identified in prior experiments or the like is extracted from the plurality of components as the extraction component, the probability of extraction of a component, which is less related to the human brain activity, as an extraction component from the plurality of components, can be reduced.

5-3

The brain has a mechanism called the selective brain cooling system whereby the brain is cooled independently of body temperature. The selective brain cooling system is known to discharge heat generated by brain activity using the forehead and the area around the paranasal sinuses. When heat is discharged, a change in the facial skin temperature resulting from brain activity or the facial blood circulation volume that correlates to the facial skin temperature appears at the forehead and/or the area around the paranasal sinuses.

In the present embodiment, various data of the forehead and/or the area around the paranasal sinuses is analyzed and the determination component is extracted. As such, it is possible to accurately extract components related to human brain activity.

5-4

When an operator of a machine is the subject, the brain activity visualization device according to the present embodiment can be used as an operator monitoring device (driver state determination device) that monitors the state of the operator. Furthermore, in the present embodiment, when the state visualization means 200 includes an output unit, the administrator can ascertain the physiological state of the operator.

(5-4-1) When Used to Monitor a Driver

Next, an example is described of a case in which operator monitoring devices (driver state determination devices) 10, 110 according to the embodiment or the modification examples described above are applied to a driver operating an automobile, construction machinery, or the like. In this case, the operator monitoring devices 10, 110 analyze the physiological state, particularly the consciousness level, of the driver as the operator on the basis of machine operations by the driver and, depending on an analyzed consciousness level, outputs information related to the consciousness level to the administrator. For example, in a case where it is determined from the analysis that the physiological state of the driver of the construction machinery or the like is in a state of carelessness, this information is output to the administrator of the construction machinery or the like. As a result, the administrator can be made aware of the consciousness level of the driver. Additionally, a configuration is possible in which the state visualization means 200 includes a notification unit 203. In this case, the notification unit 203 issues notifications to call the driver to attention depending on the analyzed consciousness level. In cases where the state visualization means 200 includes the notification unit 203, the notification unit 203 may, for example, issue an alert to the driver of the automobile, construction machinery, or the like when the consciousness level declines to less than or equal to a certain level. More specifically, changes in the amount of brain activity (degree of rise and duration thereof) during normal machine operation is recorded and, in cases where changes occur that are equal to or greater than a predetermined amount below these changes in the amount of brain activity (degree of rise and/or duration thereof) during normal operation, it is considered that the degree of concentration has decreased, and a voice, buzzer sound, or the like is emitted from the notification unit 203. As a result, the driver can be called to attention. Thus, in cases where the operator monitoring devices 10, 110 are used to monitor a driver, the physiological state of the driver is monitored using non-contact means such as the facial skin temperature acquisition means, the image data acquisition means, or the like, and the physiological state is output to the administrator and/or the driver. As a result, the occurrence of drowsy driving, inattentive driving, and the like can be suppressed.

(5-4-2) When Used to Monitor a Pilot

Next, an example is described of a case in which the operator monitoring devices (driver state determination devices) 10, 110 according to the embodiment or the modification examples described above are applied to a pilot operating an aircraft or an aircraft simulator. In this case, the operator monitoring devices 10, 110 analyze the physiological state, particularly the consciousness level, of the pilot as the operator and, depending on the analyzed consciousness level, outputs information related to the consciousness level to the administrator. For example, in a case where it is determined from the analysis that the physiological state of the pilot is unconsciousness (e.g. the pilot has fainted), this information is output to the administrator of the aircraft or the like. As a result, the administrator can be made aware of the consciousness level of the pilot. Additionally, a configuration is possible in which, for example, the aircraft or the like is switched from manual piloting to automatic piloting when the state visualization means 200 determines that the physiological state of the pilot is unconscious. Thus, in cases where the operator monitoring devices 10, 110 are used to monitor a pilot, the physiological state of the pilot is monitored using non-contact means such as the facial skin temperature acquisition means, the image data acquisition means, or the like, and the physiological state is output to the administrator. As a result, situations in which the pilot continues to operate the aircraft or the like while unconscious can be prevented.

Additionally, in cases where the operator monitoring devices 10, 110 are applied to a pilot of a fighter aircraft as a sensor of an acceleration simulator, a configuration is possible in which, for example, an amount of brain activity of the pilot is analyzed, and the amount of brain activity of the pilot based on a change in acceleration is output to the administrator. At this time, if the amount of brain activity with respect to an increase in acceleration decreases, the administrator can assume that there is not sufficient blood flow to the brain of the pilot. Pilots of fighter aircraft and other operators that train to cope with acceleration utilize pressurized suits and special breathing methods to prevent decreases in blood flow to the brain and fainting. Therefore, in cases where the output analysis results suggest that there is not sufficient blood flow to the brain of the pilot, it can be determined that the pilot has insufficient skill or is unsuitable as a pilot.

(6) Use Examples of Brain Activity Visualization Device (Driver State Determination Device)

Next, a driver state determination device to which the brain activity visualization device according to the present invention is applied will be described.

(6-1) First Embodiment (6-11) Configuration of Driver State Determination Device 400

Figure 23:
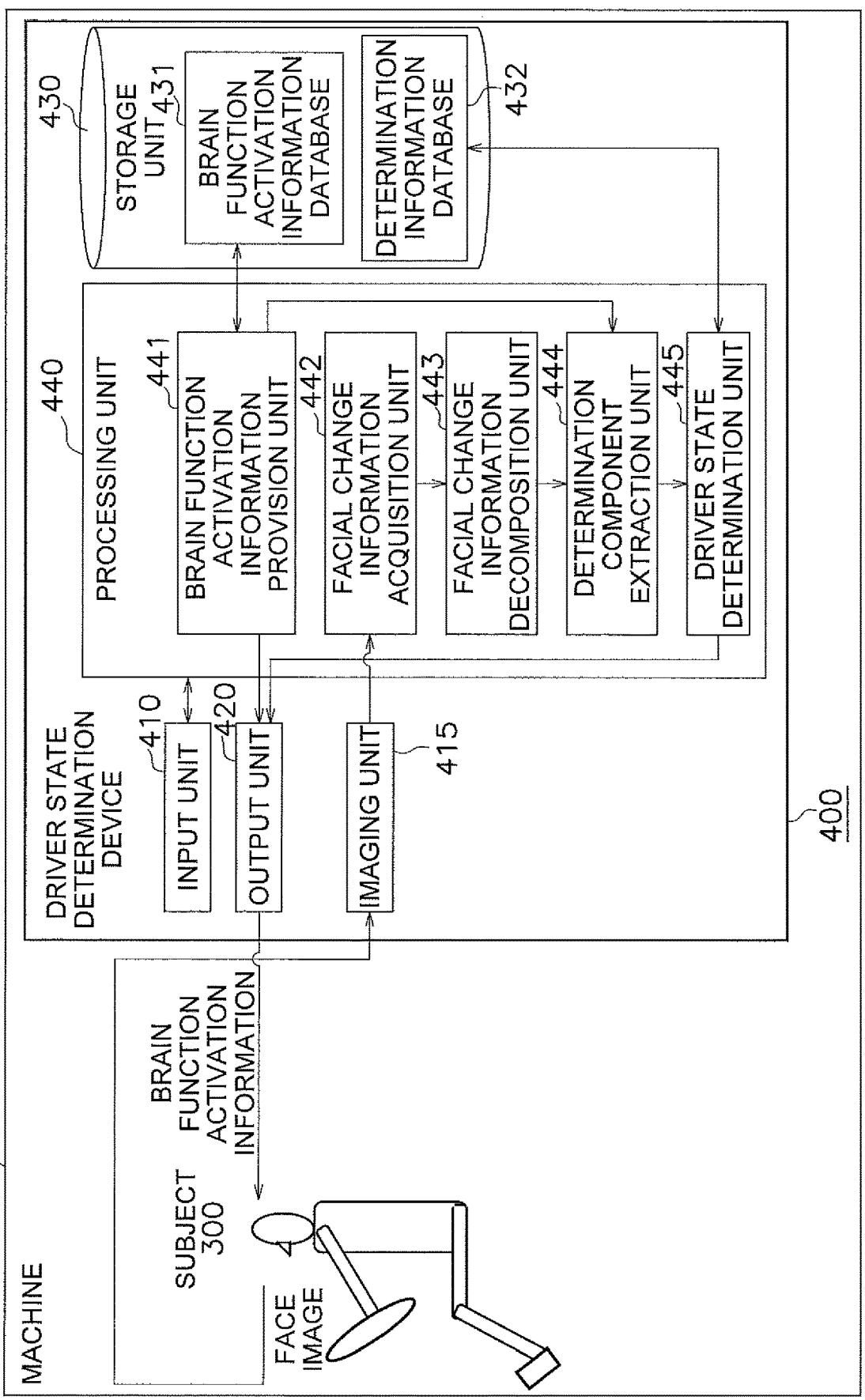
FIG. 23 is a schematic drawing illustrating a configuration of a driver state determination device 400 according to a first embodiment.

FIG. 23 is a schematic drawing illustrating an example of a driver state determination device 400 according to a first embodiment.

The driver state determination device 400 is provided with an input unit 410, an imaging unit 415, an output unit 420, a storage unit 430, and a processing unit 440. The driver state determination device 400 determines the driver state of a subject 300 driving a machine 350. Here, the term "machine" refers to transportation machines such as automobiles, railway vehicles, and aircraft, and other automatic machines such as nuclear power generation equipment and various types of plants. Additionally, the term "driver state" refers to the mental state and the physical state of the subject driving the machine. The mental state is represented by indicators corresponding to mental fatigue, mental stress, a state of carelessness, a state of concentration, and so on. The physical state is represented by indicators corresponding to physical fatigue, physical stress, and so on.

The input unit 410 is configured to input various information into the driver state determination device 400. The input unit 410 is configured from, for example, a keyboard, a mouse, and/or a touchscreen, or the like. Various commands are input into the driver state determination device 400 via the input unit 410, and processing is executed in the processing unit 440 in accordance with the commands.

The imaging unit 415 is configured to capture face images including the facial surface of the subject 300. The imaging unit 415 is configured from, for example, a CCD, CMOS, or similar solid state imaging device that acquires RGB images, and an infrared camera or the like that acquires thermograms. Using the infrared camera 415a as the imaging unit 415 enables the determination of driver states independent of ambient brightness. Accidents and the like due to fatigue are more likely to happen at night. Even in such situations, mounting the infrared camera 415a on the driver state determination device 400 according to the first embodiment enables the monitoring of driver states at night. Infrared cameras and the like preferably are capable of detection with high sensitivity under typical room temperature conditions, namely from 29.0° C. to 37.0° C. In addition, the imaging unit 415 is capable of continuous imaging at predetermined intervals. Face images are preferably captured from the front and under constant illumination. In cases where front images cannot be obtained due to posture fluctuations, the perturbation space method is used to approximate a three-dimensional shape of the facial surface for images with varying postures, and obtain a face image by rendering the three-dimensional shape in a front view. For images with illumination fluctuations, an illumination base model of the facial surface based on the diffuse reflection model is used to obtain face images under constant illumination conditions. Then, the continuously captured face images are sent from the imaging unit 415 to the processing unit 440.

The output unit 420 is configured to output various information from the driver state determination device 400. In one example, the output unit 420 is configured from a display and a speaker, or the like. In this case, brain function activation information (described later) is provided to the subject 300 via the output unit 420.

The information input into the driver state determination device 400, the information calculated by the driver state determination device 400, and the like are stored in the storage unit 430. In one example, the storage unit 430 is configured from memory, a hard disk device, or the like. Programs for realizing the various functions of the processing unit 440 (described below) are also stored in the storage unit 430. In this case, the storage unit 430 includes a brain function activation information database 431 and a determination information database 432.

Brain function activation information that activates human brain function is stored in the brain function activation information database 431. Here, the phrase "brain function activation information" refers to information obtained from arbitrary events and points in time related to the driving of automobiles, railway vehicles, and aircraft, and other automatic machines such as nuclear power generation equipment and various types of plants. When, for example, the subject 300 is the driver of a transportation machine such as an automobile, a railway vehicle, or an aircraft, an alarm sound or the like can be used as the brain function activation information.

Figure 24:
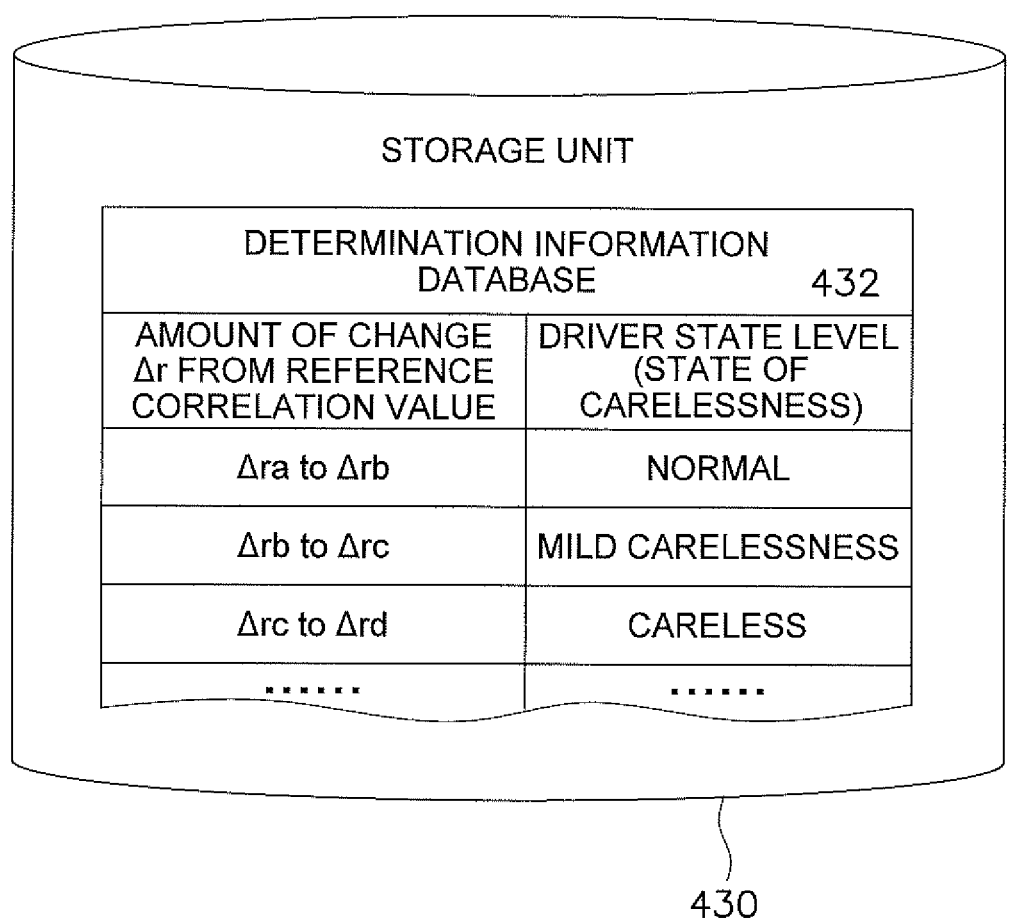
FIG. 24 is a schematic drawing illustrating a configuration of a determination information database 432 according to the first embodiment.

As illustrated in FIG. 24, in the determination information database 432, a driver state level is associated with an amount of change $\Delta r$ ($=r1-r2$) of a predetermined range and stored, in advance, as determination information. The amount of change $\Delta r$ is defined as an amount of change of a correlation value r2 of a determination component to the brain function activation information extracted by a determination component extraction unit 444 (described later) from a reference correlation value r1 of a reference determination component to the brain function activation information. The reference determination component is configured from data of determination components extracted prior to a predetermined action, data of previously extracted determination components, data of determination components provided from an external source, or the like. In the example illustrated in FIG. 24, the driver states are recorded in the determination information database 432 by level of the state of carelessness. That is, the driver state levels are stored in the determination information database 432 in accordance with the range of the value of the amount of change $\Delta r$. Specifically, $\Delta r = \Delta ra$ to $\Delta rb$ indicates a driver state level of "normal", $\Delta r = \Delta rb$ to $\Delta rc$ indicates a driver state level of "mild carelessness", and $\Delta r = \Delta rc$ to $\Delta rd$ indicates a driver state level of "careless." In this case, values increase in the order of $\Delta ra$, $\Delta rb$, $\Delta rc$, and $\Delta rd$. Note that data of the reference determination component is also stored in the determination information database 432.

The processing unit 440 is configured to execute information processing in the driver state determination device 400. Specifically, the processing unit 440 is configured from a CPU, cache memory, and the like. The processing unit 440 executes the programs incorporated into the storage unit 430 to function as a brain function activation information provision unit 441, a facial change information acquisition unit 442, a facial change information decomposition unit 443, a determination component extraction unit 444, and a driver state determination unit 445.

The brain function activation information provision unit 441 is configured to provide brain function activation information to the subject 300 driving the machine 350. In one example, in accordance with operations of the input unit 410, the brain function activation information provision unit 441 reads the brain function activation information from the brain function activation information database 431 and outputs this brain function activation information to the output unit 420.

The facial change information acquisition unit 442 is configured to acquire facial data and facial change information exhibiting time-series changes in the facial data from the face images captured by the imaging unit 415. Specifically, the facial change information acquisition unit 442 acquires the facial data from the imaging unit 415 in synchronization with the timing at which the brain function activation information provision unit 441 provides the brain function activation information. Moreover, the facial change information acquisition unit 442 acquires facial change information indicating time-series changes in the facial data of the subject 300 from continuously acquired facial data. In an example in which 60 pieces of facial data of 240×320 pixels are acquired at predetermined intervals, the facial change information is a set of 4,608,000 pieces of data. The acquired facial change information is sent to the facial change information decomposition unit 443. Note that, when the imaging unit 415 is an infrared camera, the facial change information acquisition unit 442 acquires facial skin temperature data indicating the facial skin temperature of the subject 300 as the facial data. Additionally, when the imaging unit 415 is a CCD, CMOS, or similar solid state imaging device, the facial change information acquisition unit 442 acquires facial blood circulation volume data based on RGB data of the facial surface of the subject 300 as the facial data. Note that a configuration is possible in which the facial change information acquisition unit 442 acquires data of the forehead and/or the area around the paranasal sinuses of the subject 300 as the facial data.

The facial change information decomposition unit 443 decomposes the facial change information, which is a set of multiple pieces of data, into a plurality of components 1, 2, 3 . . . by singular value decomposition, principal component analysis, or independent component analysis. Information of each of the decomposed components is sent to the determination component extraction unit 444. In this case, when the facial change information is subjected to singular value decomposition or the like, the components 1, 2, 3 . . . are numbered in descending order of the singular value. Components with higher singular values are more likely to reflect the influence of components that fluctuate greatly. As such, the influence of noise and the like of the external environment, and not the influence imparted by the brain function activation information, is often reflected in the component 1.

The determination component extraction unit 444 is configured to extract, from the plurality of components 1, 2, 3 . . . , a component related to the brain function activation information as the determination component. Additionally, the determination component extraction unit 444 calculates a correlation value r of the extracted determination component to the brain function activation information. Specifically, the determination component extraction unit 444 calculates the correlation value r between the brain function activation information and the plurality of components 1, 2, 3 . . . decomposed by the facial change information decomposition unit 443. Next, when the calculated correlation value r is greater than or equal to a predetermined value, the determination component extraction unit 444 sets the component corresponding to that correlation value r to be a component related to the brain function activation information. Then, the determination component extraction unit 444 extracts the determination component on the basis of a value of a critical rate. Specifically, the determination component extraction unit 444 extracts a component for which the critical rate is low as the determination component. The extracted determination component and calculated correlation value r are sent to the storage unit 430 or the driver state determination unit 445.

The driver state determination unit 445 is configured to determine the driver state of the subject 300 driving the machine 350 on the basis of the determination component. Specifically, the driver state determination unit 450 calculates a difference Δr between a reference correlation value r1 of the brain function activation information with respect to a reference determination component extracted at a predetermined timing and a correlation value r2 of the brain function activation information with respect to a determination component extracted thereafter. Then, the driver state determination unit 450 determines the driver state level corresponding to the difference Δr between the reference correlation value r1 and the current correlation value r2 on the basis of the determination information stored in the determination information database 432. The determined driver state level is output via the output unit 420 to a display device or the like.

(6-1-2) Operations of Driver State Determination Device 400

Figure 25A:
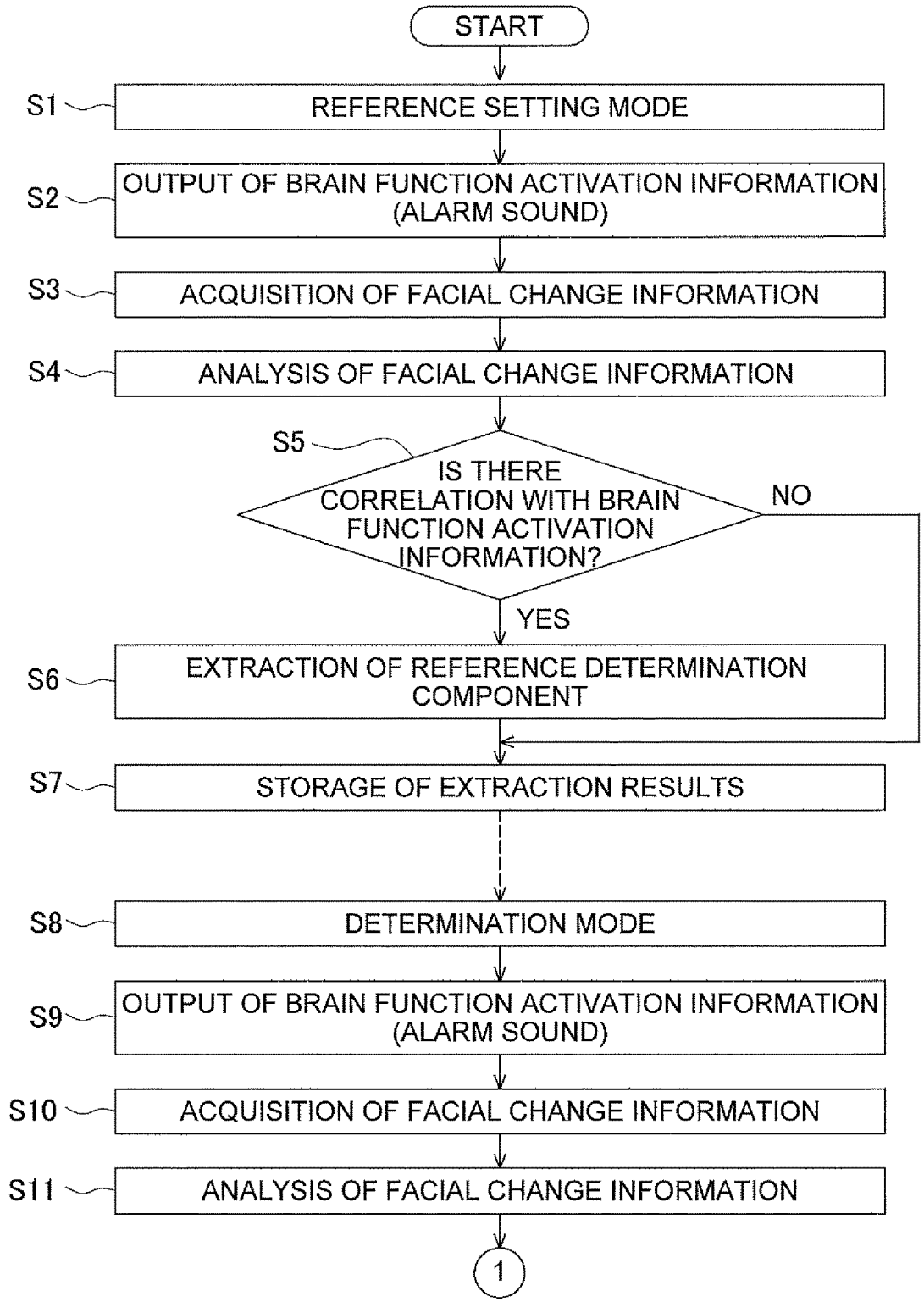
FIG. 25A is a flowchart showing operations of the driver state determination device 400 according to the first embodiment.
Figure 25B:
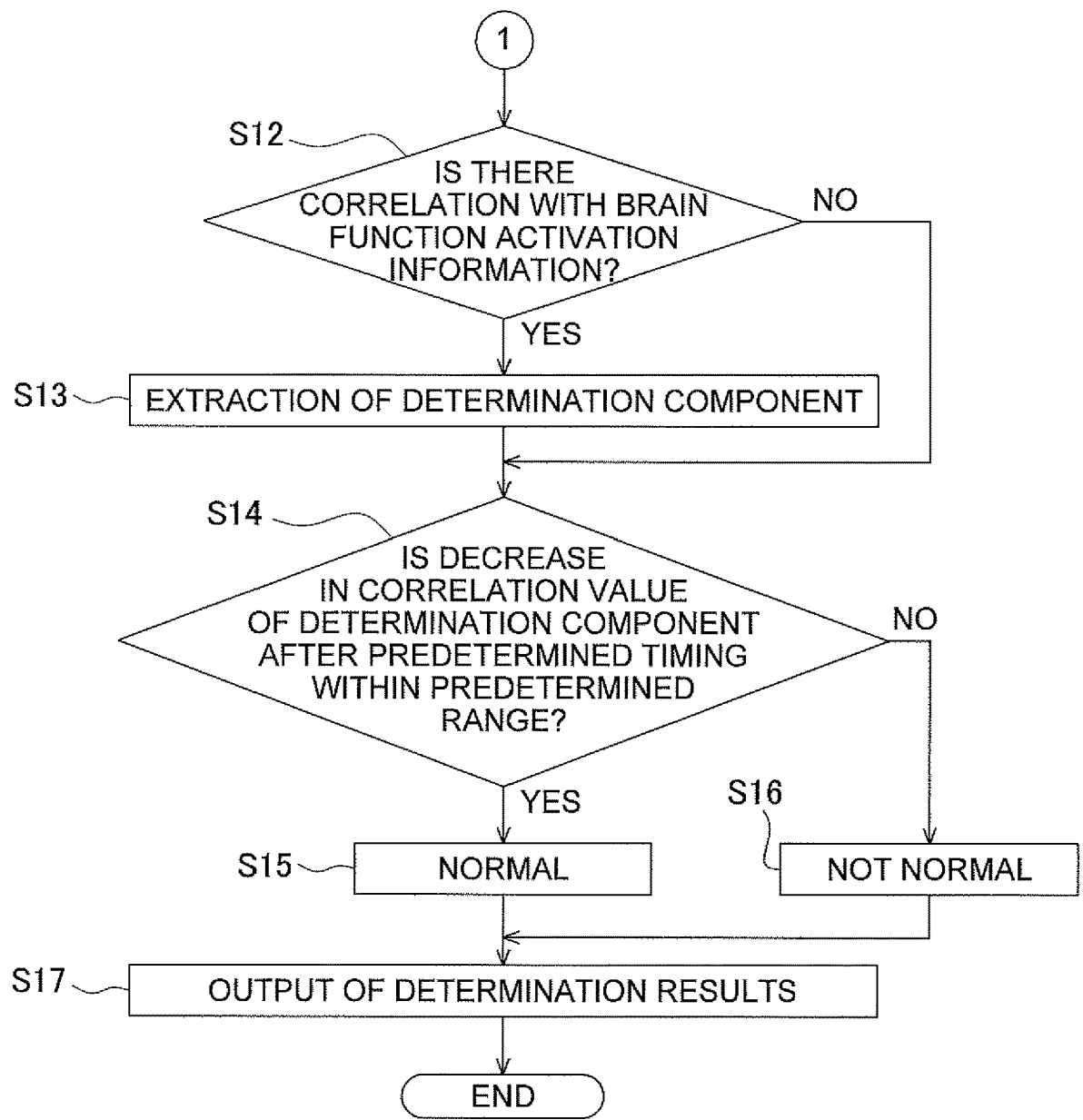
FIG. 25B is a flowchart showing operations of the driver state determination device 400 according to the first embodiment.

FIGS. 25A and 25B are flowcharts showing operations of the driver state determination device 400 according to the first embodiment.

First, at a predetermined timing during driving of the machine 350, "reference setting mode" is selected and the reference determination component is extracted (S1). Specifically, an output command of the brain function activation information is input via the input unit 410 into the driver state determination device 400. Next, the brain function activation information is read from the brain function activation information database 431 and output to the output unit 420 (S2). In one example, an alarm sound is output as the brain function activation information in this case.

Next, simultaneously with the output of the brain function activation information or at a predetermined timing, the imaging unit 415 captures face images including the facial surface of the subject 300 positioned in front of the output unit 420. The face images are captured at predetermined intervals (S3). The captured face images are sent to the facial change information acquisition unit 442.

Next, the facial change information acquisition unit 442 acquires facial change information indicating time-series changes in the facial data of the subject 300 from acquired facial data. Then, the facial change information decomposition unit 443 decomposes the facial change information into the plurality of components 1, 2, 3 . . . by singular value decomposition, principal component analysis, or independent component analysis (S4).

Next, the determination component extraction unit 444 calculates the correlation value between the brain function activation information and the plurality of components 1, 2, 3 . . . decomposed by the facial change information decomposition unit 443. Then, the determination component extraction unit 444 determines whether or not the correlation value is greater than or equal to the predetermined value (S5). When the correlation value is determined to be greater than or equal to the predetermined value, it is determined that there is correlation between the brain function activation information and that component (S5—Yes). Then, the determination component extraction unit 444 extracts, from among the components having correlation, a component for which the critical rate is low as the "reference determination component" (S6). Additionally, the determination component extraction unit 444 sets the correlation value between the reference determination component and the brain function activation information as the reference correlation value r1. Information of these reference determination components is stored in the storage unit 430 (S7). Meanwhile, when the correlation value between the brain function activation information and each of the components 1, 2, 3 . . . is less than the predetermined value, it is determined that there is no correlation therebetween, and that information is stored in the storage unit 430 (S5—No, S7).

Thereafter, at a desired timing during driving of the machine 350, "determination mode" is selected and the subsequent driver state is determined (S8). The determination mode may be automatically or manually selected.

First, the same processing as in S2 to S6 is executed, and the correlation value r2 between the brain function activation information and the determination component extracted from the facial change information is calculated (S9 to S13).

Then, the driver state determination unit 445 calculates the amount of change Δr, which is the difference between the reference correlation value r1 of the brain function activation information with respect to the reference determination component extracted in the reference setting mode and the correlation value r2 of the brain function activation information with respect to the determination component extracted in the determination mode (S14). Next, the driver state determination unit 450 determines whether or not the amount of change Δr of the correlation value r2 with respect to the reference correlation value r1 is within a predetermined range. Whether or not the amount of change Δr is within the predetermined range is determined on the basis of the determination information stored in the determination information database 432. When the amount of change Δr of the correlation value r2 with respect to the reference correlation value r1 is within a predetermined range, the driver state determination unit 445 determines that the driver state of the subject 300 driving the machine 350 is normal (S14—Yes, S15). When the amount of change Δr of the correlation value r2 with respect to the reference correlation value r1 is not within the predetermined range, the driver state determination unit 445 determines that the driver state of the subject 300 driving the machine 350 is not normal (S14—No, S16). In one example, the driver state determination unit 445 determines that the driver state is normal when the amount of change Δr is in the range Δra to Δrb described above, and that the driver state is not normal when the amount of change Δr exceeds Δrb. These determination results are output via the output unit 420 to a display device or the like (S17).

(6-1-3) Features of Driver State Determination Device 400

6-1-3-1

As described above, the driver state determination device 400 according to the first embodiment includes the brain function activation information provision unit 441, the facial change information acquisition unit 442, the facial change information decomposition unit 443, the determination component extraction unit 444, and the driver state determination unit 445. The brain function activation information provision unit 441 provides the brain function activation information, which activates human brain function, to the subject 300 driving the machine 350. The facial change information acquisition unit 422 acquires the facial change information indicating time-series changes in the facial data of the subject 300. The facial change information decomposition unit 433 decomposes the facial change information into the plurality of components 1, 2, 3 . . . by singular value decomposition, principal component analysis, or independent component analysis. The determination component extraction unit 444 extracts, from the plurality of components 1, 2, 3 . . . , a component related to the brain function activation information as the determination component. The driver state determination unit 445 determines the driver state of the subject 300 driving the machine 350 on the basis of the determination component.

Accordingly, with the driver state determination device 400 according to the first embodiment, the plurality of components are obtained by subjecting the facial change information to singular value decomposition, principal component analysis, or independent component analysis, and the determination component related to the provided brain function activation information is extracted from the plurality of components. As such, the presence/absence of brain activity of the subject 300 can be easily estimated without using electrodes or the like that require pretreatment before being applied. As a result, the driver state of the subject 300 driving the machine 350 can be easily determined on the basis of the determination component corresponding to the brain function of the subject 300.

Figure 26:
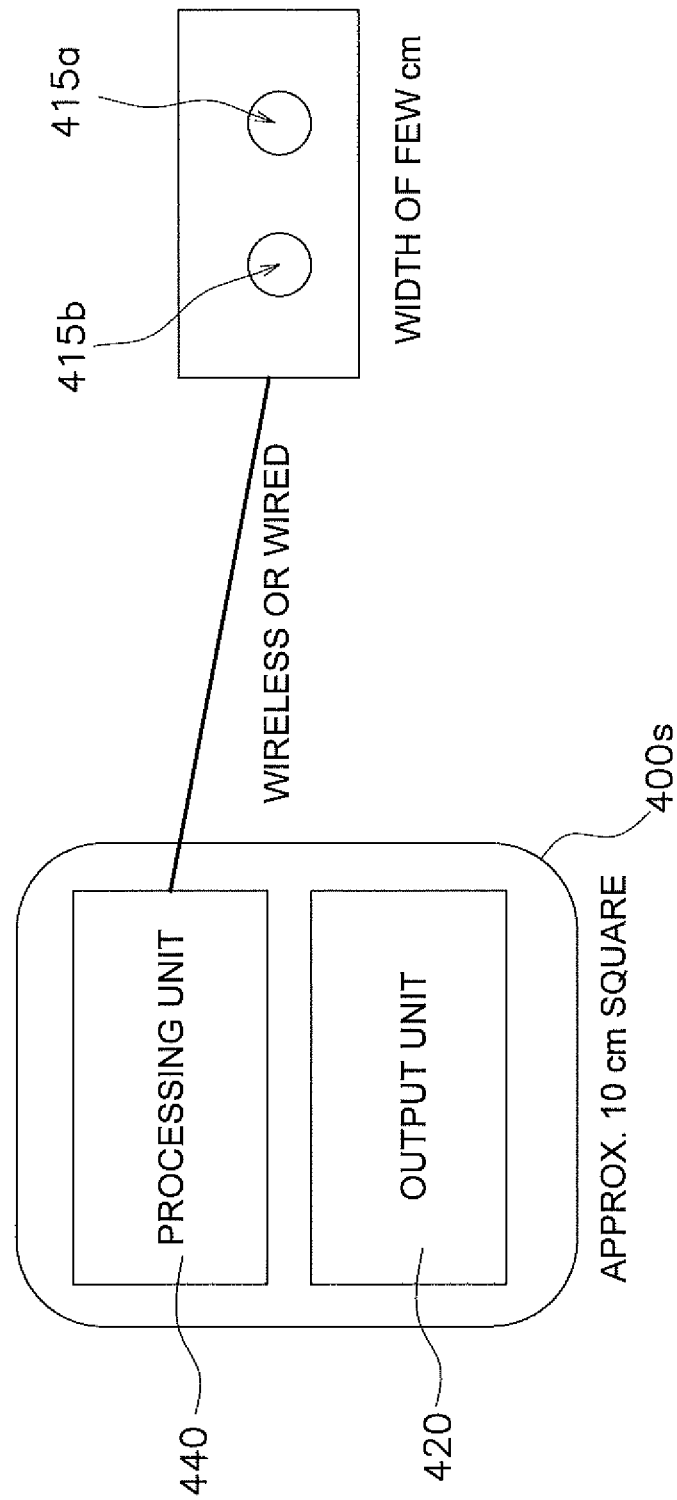
FIG. 26 is a drawing illustrating an example of a specific configuration of the driver state determination device 400 according to the first embodiment.

Note that when the machine 350 is an automobile, a configuration is possible in which, as illustrated in FIG. 26, the imaging unit 415 configured from a video camera 415b and the infrared camera 415a is installed in front of the subject 300 so as to fit in a width of a few centimeters. Typically, drivers face forward and, as such, with this configuration, face images with little movement can be captured and the extraction accuracy of the determination component can be enhanced. Additionally, a configuration is possible in which the imaging unit 415 is connected wirelessly or by wire to a touch panel device 400s in which the output unit 420 and the processing unit 440 are integrated. For example, installation in an automobile is facilitated by configuring a display screen of the device 400s to be a 10 cm square.

Additionally, a configuration is possible in which the driver state determination device 400 according to the first embodiment is incorporated into a smart device. In this case, driver state determination can be easily executed by connecting the smart device to the vehicle equipment.

6-1-3-2

With the driver state determination device 400 according to the first embodiment, the facial change information acquisition unit 442 acquires data of the forehead and/or the area around the paranasal sinuses of the subject 300 as the facial data. As a result, the determination component related to brain activity can be extracted with high accuracy. The brain has a mechanism called the selective brain cooling system whereby the brain is cooled independently of body temperature. The selective brain cooling system is known to discharge heat generated by brain activity using the areas around the forehead and the paranasal sinuses. Thus, the component related to brain activity can be extract with high accuracy by analyzing data from these sites. As a result, the driver state determination device 400 according to the first embodiment can execute driver state determination with high accuracy.

6-1-3-3

Figure 27:
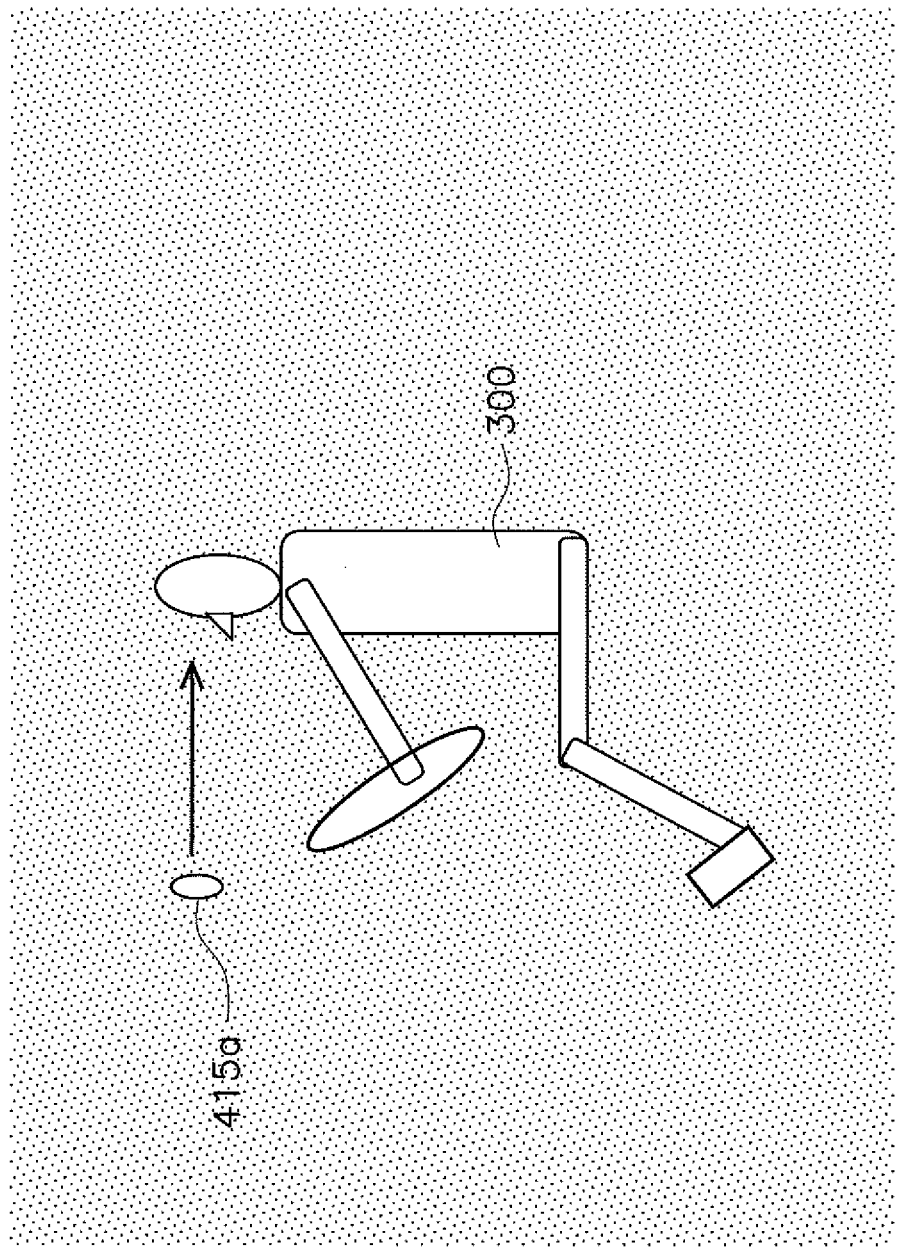

With the driver state determination device 400 according to the first embodiment, the facial change information acquisition unit 442 acquires facial skin temperature data indicating the facial skin temperature of the subject 300 as the facial data. In other words, the driver state determination device 400 is configured to be capable of using an infrared camera or the like to determine the driver state. For example, as illustrated in FIG. 27, using the infrared camera 415a as the imaging unit 415 enables the determination of the driver state independent of ambient brightness. With automobiles, careless driving is particularly more likely to occur at night. Even in such situations, mounting the infrared camera 415a on the driver state determination device 400 according to the first embodiment enables the monitoring of driver states at night. Using the infrared camera 415a also provides a benefit of being able to determine the driver state even if there is a tunnel.

6-1-3-4

With the driver state determination device 400 according to the first embodiment, the facial change information acquisition unit 442 acquires facial blood circulation volume data based on RGB data of the facial surface of the subject 300 as the facial data. In other words, the driver state determination device 400 can use a solid state imaging device (CCD, CMOS) to determine the driver state. As a result, driver state determination can be executed with a simple configuration.

6-1-3-5

With the driver state determination device 400 according to the first embodiment, the determination component extraction unit 444 extracts the determination component on the basis of the value of the critical rate. With the driver state determination device 400, the determination component related to the brain function activation information is extracted on the basis of the value of the critical rate. As such, the reliability of the driver state determination can be enhanced.

6-1-3-6

The driver state determination device 400 according to the first embodiment includes the determination information database 432. The amount of change $\Delta r$ of the predetermined range is associated with the driver state level and stored as the determination information in the determination information database 432. The amount of change $\Delta r$ is defined as the amount of change, of the correlation value r2 of the determination component calculated for the brain function activation information, from the reference correlation value r1 of the reference determination component calculated for the brain function activation information. Moreover, the driver state determination unit 445 calculates the correlation value r2 of the determination component to the brain function activation information, and can easily determine the driver state level of the subject 300 on the basis of the calculated correlation value r2 and the determination information.

As a result of this configuration, the driver state determination device 400 can easily determine the driver state level by using the reference determination component obtained at the predetermined timing. That is, the driver state determination device 400 is capable of not only simply determining whether or not the driver state is normal, but can also easily determine and output the driver state level.

6-1-3-7

With the driver state determination device 400 according to the first embodiment, the machine 350 driven by the subject 300 is a transportation machine such as an automobile, a railway vehicle, and an aircraft, or another automatic machine such as nuclear power generation equipment and various types of plants. Accordingly, with the driver state determination device 400 according to the first embodiment, the driver state of the subject 300 driving these types of automatic machines can be determined.

6-1-3-8

A driver state determination method according the first embodiment does not necessarily require the driver state determination device 400. That is, regardless of whether or not the driver state determination device 400 is provided, it is sufficient that the driver state determination method according to the present embodiment include a brain function activation information provision step for providing, at a predetermined timing, the subject 300 with brain function activation information that activates human brain function; then, a facial change information acquisition step for acquiring facial change information indicating time-series changes in the facial data of the subject 300; a facial change information decomposition step for decomposing the facial change information into a plurality of components by singular value decomposition, principal component analysis, or independent component analysis; a determination component extraction step for extracting a component related to the brain function activation information from the plurality of components as a determination component; and a driver state determination step for determining, on the basis of the determination component, a driver state of the subject 300 driving the machine 350.

According to this driver state determination method, the plurality of components is obtained by subjecting the facial change information to singular value decomposition, principal component analysis, or independent component analysis after the predetermined timing, and the determination component related to the brain function activation information is extracted from the plurality of components. As such, the driver state of the subject 300 driving the machine 350 can be easily determined.

(6-1-4) Modification Example of Driver State Determination Device 400

Figure 28:
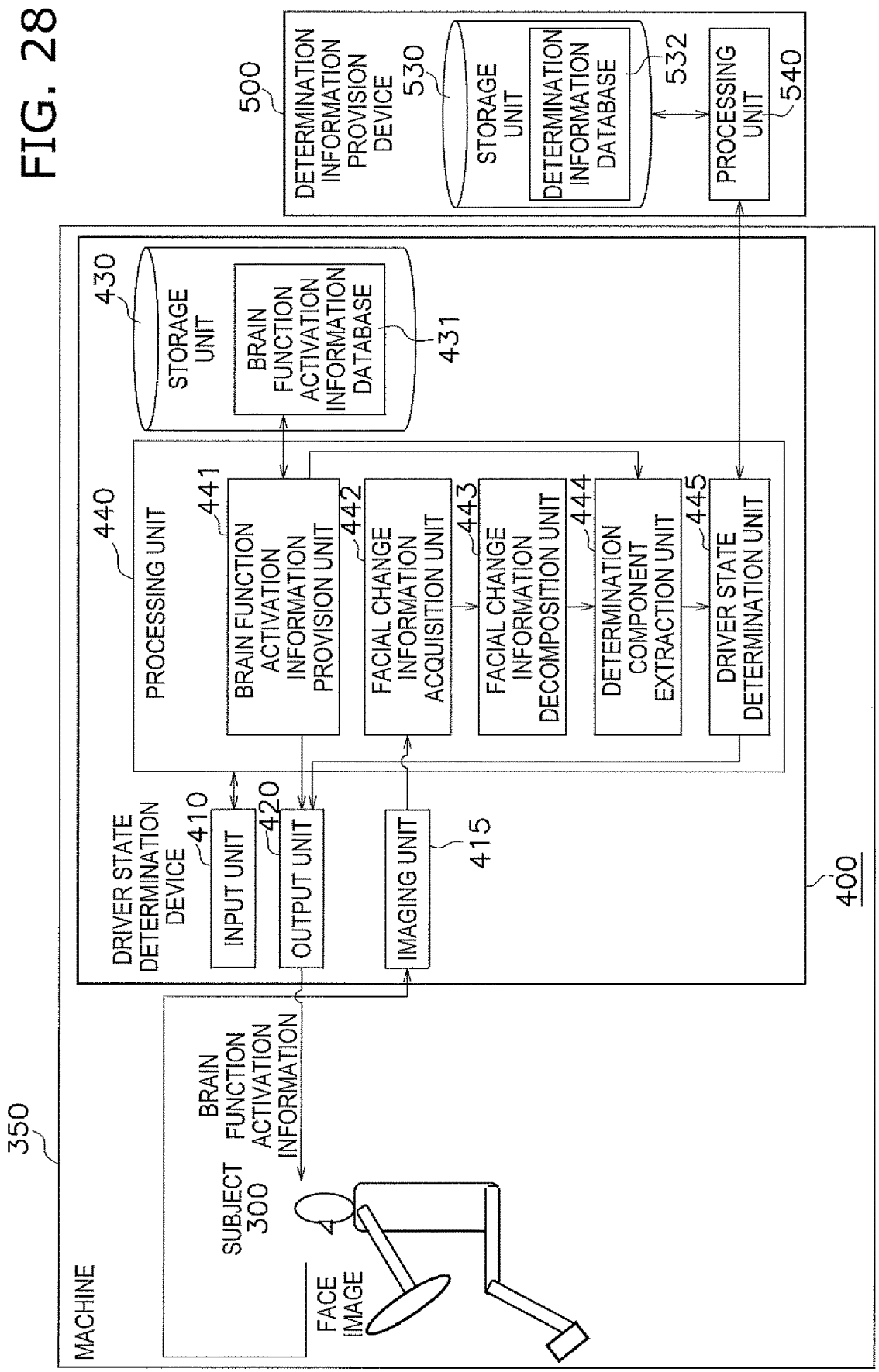
FIG. 28 is a schematic drawing illustrating a configuration of a modified example of the driver state determination device 400 according to the first embodiment.

As illustrated in FIG. 28, a configuration is possible in which a determination information provision device 500 or the like provided on a network is used in the driver state determination device 400 according to the present embodiment.

In this case, the determination information provision device 500 includes a storage unit 530 and a processing unit 540.

The storage unit 530 includes a determination information database 532. This determination information database 532 has the same configuration as the determination information database 432 described above. Specifically, an amount of change Δr of a predetermined range is associated with a driver state level and stored as determination information in the determination information database 532. The amount of change Δr is defined as the amount of change, of a correlation value r2 of the determination component calculated for the brain function activation information, from a reference correlation value r1 of a reference determination component calculated for the brain function activation information.

The processing unit 540 sends the determination information stored in the determination information database 532 in accordance with requests from the driver state determination device 400. Note that, a configuration is possible in which the processing unit 540 has a function for generating, on the basis of predetermined information, determination information as big data, independent of the determination component extracted by the driver state determination device 400. Additionally, in cases where the reference correlation value r1 is calculated by the driver state determination device 400, the processing unit 540 executes, at all times, processing for updating the reference correlation value r1 stored in the determination information database 432.

In the present modification example, the driver state determination unit 445 issues requests to the determination information provision device 500 for the provision of the determination information. Specifically, in the present modification example, the determination information database 532 is stored in the determination information provision device 500, which is on the network, and the driver state determination unit 445 accesses the determination information provision device 500 when the driver state level is determined. Moreover, the driver state determination unit 445 determines the driver state level of the subject 300 on the basis of the calculated correlation value r2 and the determination information.

Figure 29:
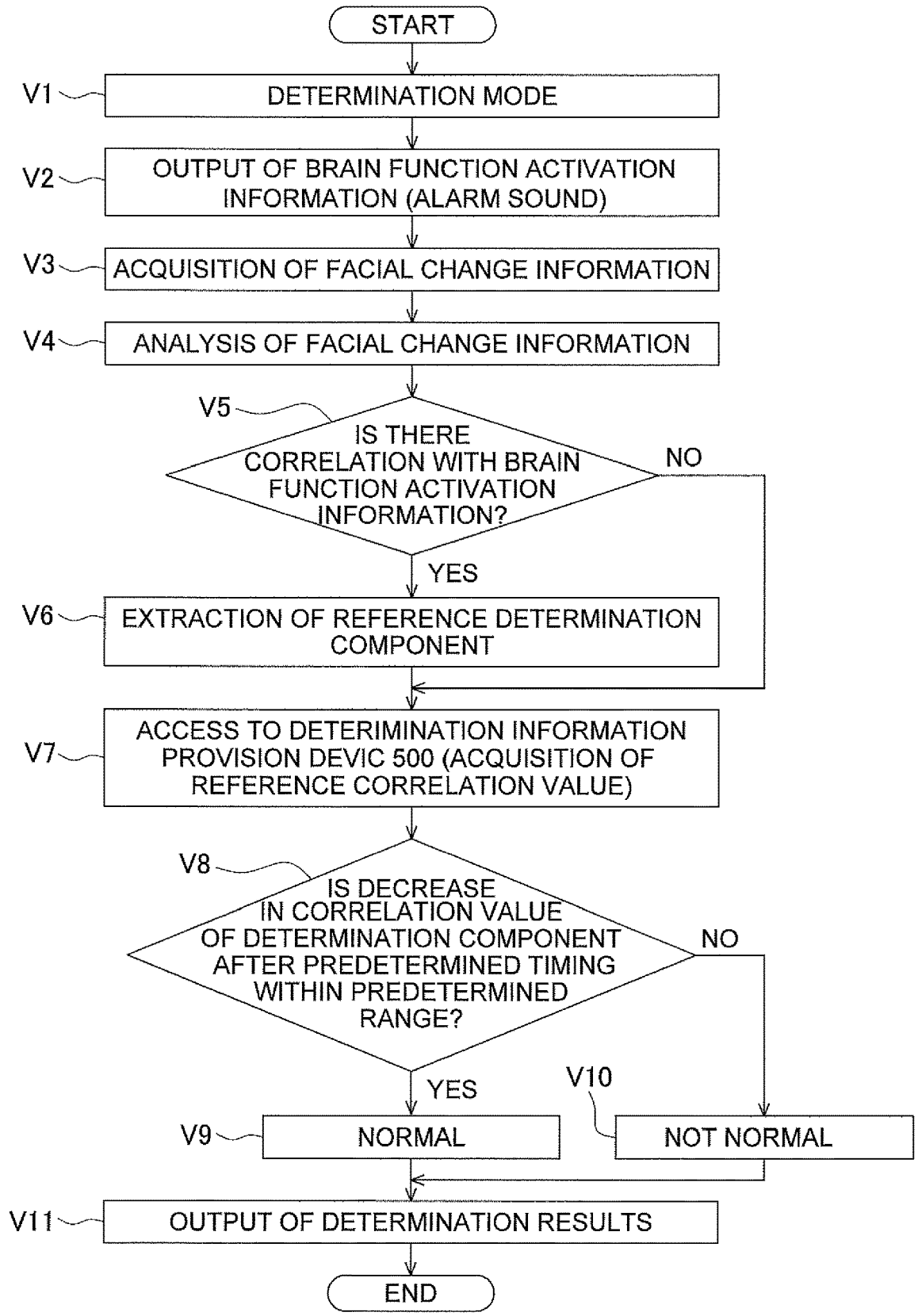
FIG. 29 is a flowchart showing operations of the modified example of the driver state determination device 400 according to the first embodiment.

Accordingly, with the driver state determination device 400 of the present modification example, the driver state determination unit 445 can use an external network to determine the driver state level of the subject 300. Additionally, the driver state determination unit 445 determines the driver state using the reference determination component stored in the determination information provision device 500, which is on the external network. As such, it is possible to streamline reference setting work. That is, as illustrated in FIG. 29, a configuration is possible in which the reference setting mode described above is omitted and only the determination mode is executed. In this case, the processing described above for steps S8 to S17 is performed in steps V1 to V6 and V8 to V11. Additionally, in step V7, the driver state determination device 400 issues a send request to the determination information provision device 500 for the determination information. Note that the steps described above may be executed in part without using the driver state determination device 400.

Additionally, the method of the present modification example enables the determination of the driver state using big data. That is, the reference correlation value r1 and the predetermined amount of change Δr are obtained from big data. Specifically, the brain function activation information is provided to a person other than the subject to obtain a reference determination component, and a reference correlation value r1 calculated on the basis of this reference determination component is used. As a result, the determination information can be optimized at all times.

(6-2) Second Embodiment (6-2-1) Configuration of Driver State Determination Device 400A In the following, constituents identical to those described previously are assigned the same reference signs and redundant description thereof is foregone. To distinguish from the other embodiments, some constituents that differ in the present embodiment are marked with the letter "A."

Figure 30:
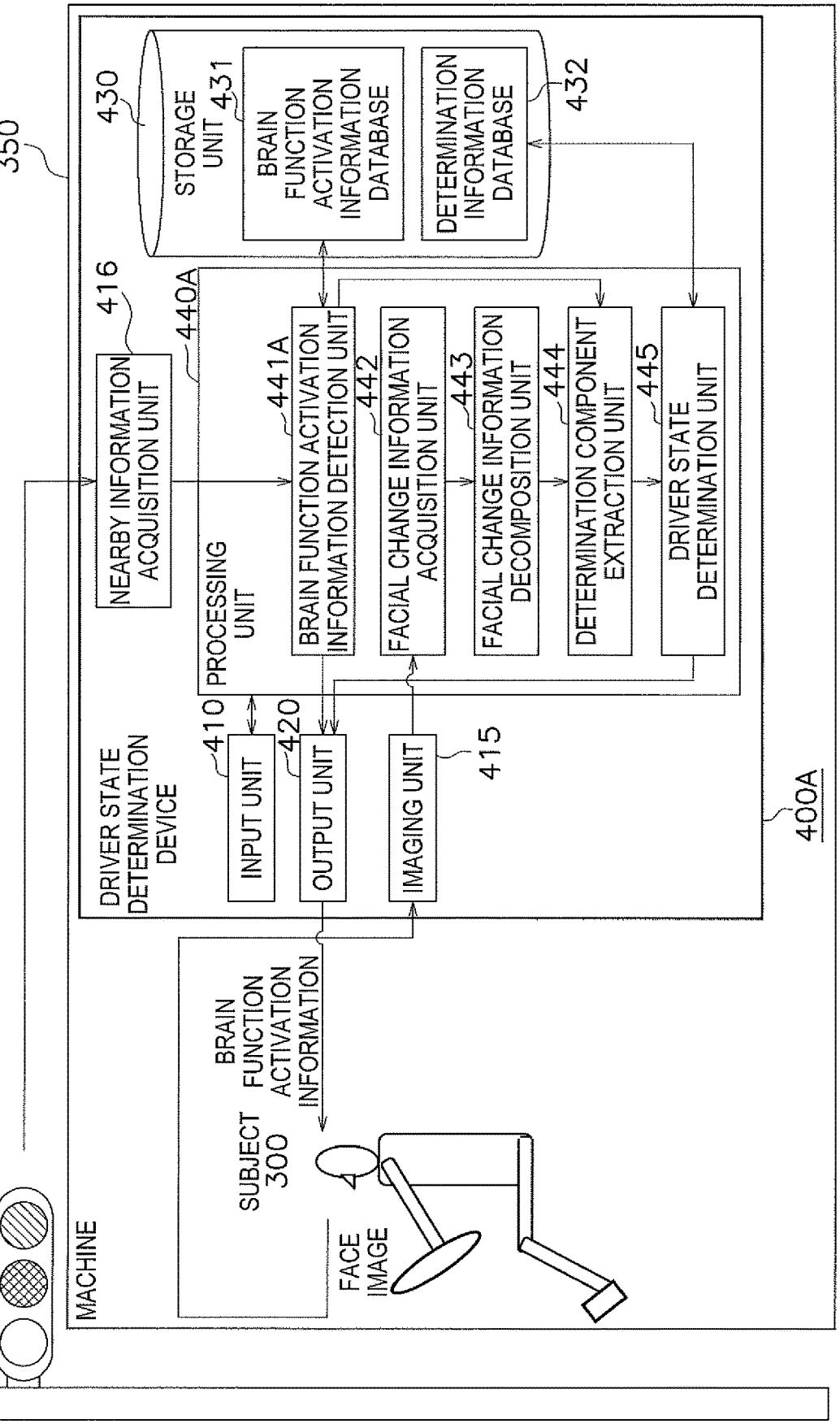
FIG. 30 is a schematic drawing illustrating a configuration of a driver state determination device 400A according to a second embodiment.

FIG. 30 is a schematic drawing illustrating an example of a driver state determination device 400A according to a second embodiment. The second embodiment differs from the first embodiment in that the brain function activation information is detected from an external source.

The driver state determination device 400A is provided with an input unit 410, an imaging unit 415, a nearby information acquisition unit 416, an output unit 420, a storage unit 430, and a processing unit 440A. The driver state determination device 400A determines the driver state of a subject 300 driving a machine 350. Here, the term "machine" refers to transportation machines such as automobiles, railway vehicles, and aircraft, and other automatic machines such as nuclear power generation equipment and various types of plants.

In the second embodiment, a brain function activation information provision object 600 is present near the machine 350. The brain function activation information provision object 600 is configured to provide brain function activation information that activates human brain function. Here, the phrase "brain function activation information" refers to information obtained from arbitrary events and points in time related to the driving of transportation machines such as automobiles, railway vehicles, and aircraft, and other automatic machines such as nuclear power generation equipment and various types of plants. When, for example, the subject 300 is the driver of an automobile, a display of a red traffic light or the like can be used as the brain function activation information. In this case, the brain function activation information provision object 600 is a traffic light.

The nearby information acquisition unit 416 is configured to detect the brain function activation information provided from the brain function activation information provision object 600 near the machine 350. When, for example, the display of a red traffic light is used as the brain function activation information, the nearby information acquisition unit 416 acquires nearby images of the machine 350. The information acquired by the nearby information acquisition unit 416 is sent to a brain function activation information detection unit 441A of the processing unit 440A.

The processing unit 440A is configured to execute information processing in the driver state determination device 400A. Specifically, the processing unit 440A is configured from a CPU, cache memory, and the like. The processing unit 440A executes the programs incorporated into the storage unit 430 to function as the brain function activation information detection unit 441A, the facial change information acquisition unit 442, the facial change information decomposition unit 443, the determination component extraction unit 444, and the driver state determination unit 445.

The brain function activation information detection unit 441A is configured to detect brain function activation information that activates human brain function. The brain function activation information is provided from the brain function activation information provision object 600 to the subject 300 operating the machine 350. Specifically, the brain function activation information detection unit 441A detects the brain function activation information via the nearby information acquisition unit 416. When, for example, the display of a red traffic light is used as the brain function activation information, the brain function activation information detection unit 441A issues a send request to the nearby information acquisition unit 416 for the nearby images. When the nearby images are sent from the nearby information acquisition unit 416 in accordance with this send request, the brain function activation information detection unit 441A detects whether or not a red traffic light is displayed in the nearby images. When the brain function activation information detection unit 441A detects the brain function activation information, the determination component extraction unit 444 calculates the correlation value r between the detected brain function activation information and the determination component.

(6-2-2) Operations of Driver State Determination Device 400A

Figure 31A:
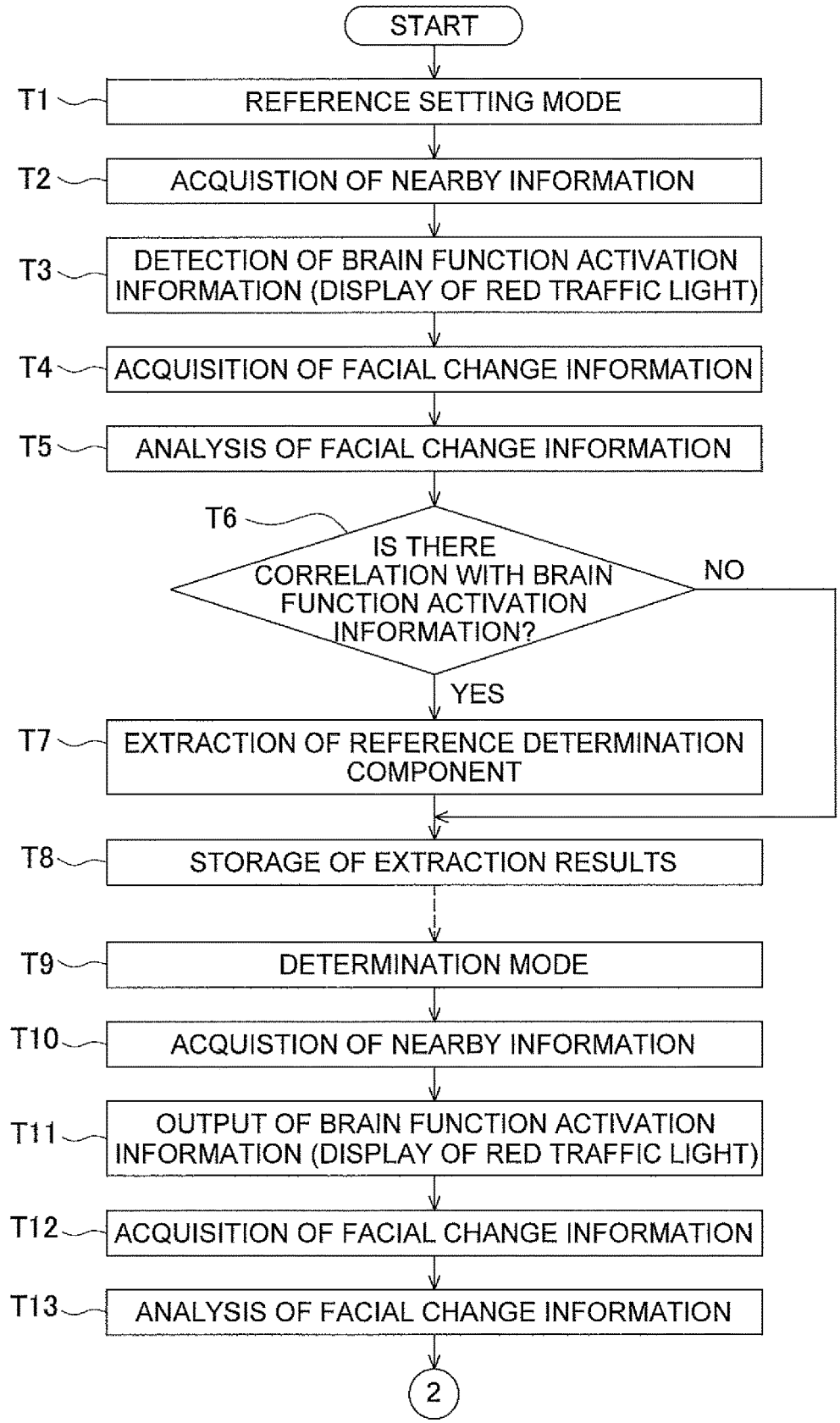
FIG. 31A is a flowchart showing operations of the driver state determination device 400A according to the second embodiment.
Figure 31B:
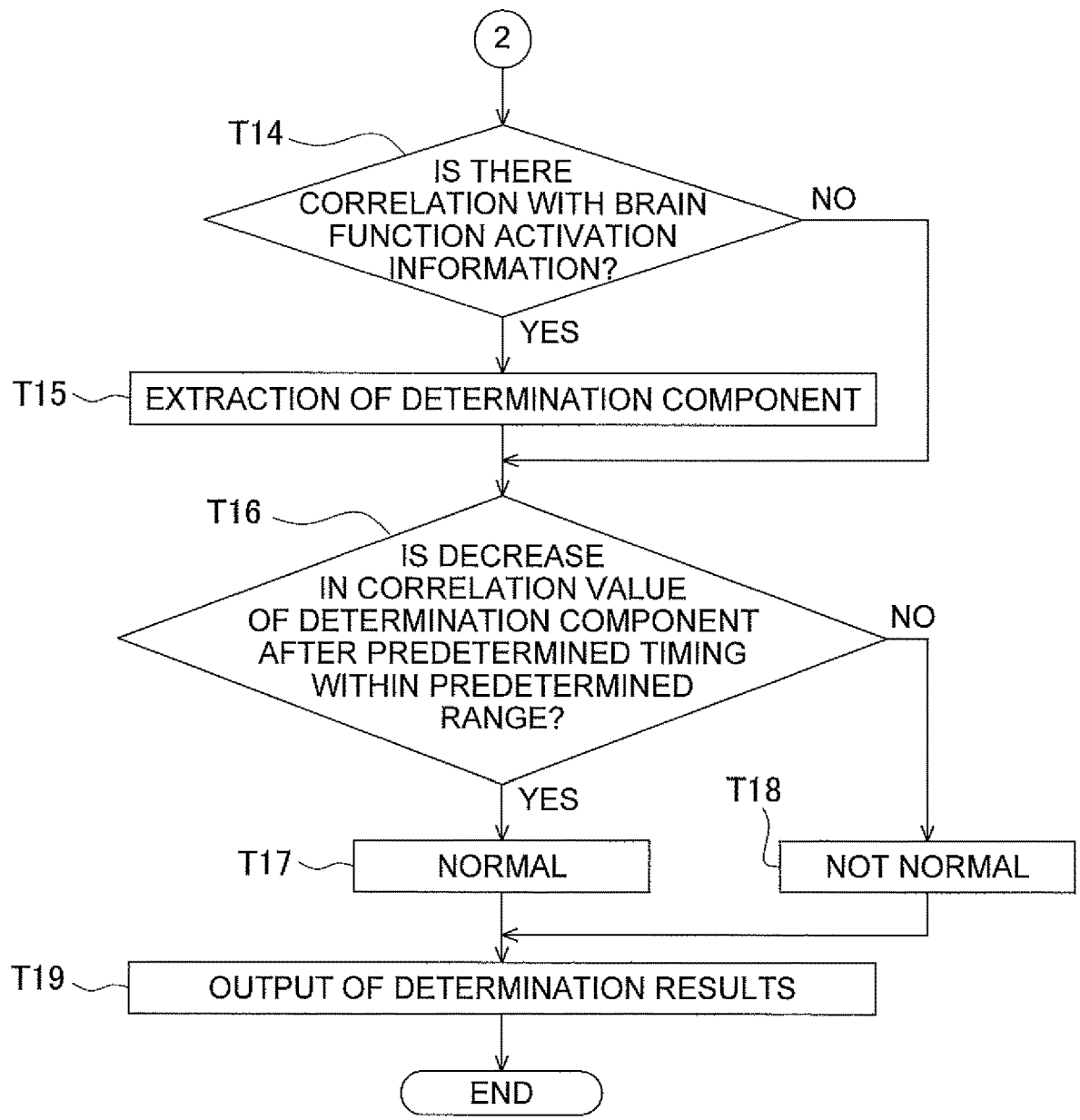
FIG. 31B is a flowchart showing operations of the driver state determination device 400A according to the second embodiment.

FIG. 31 is a flowchart showing operations of the driver state determination device 400A according to the second embodiment.

First, at a predetermined timing during driving of the machine 350, "reference setting mode" is selected and the reference determination component is extracted (T1). Specifically, the nearby information acquisition unit 416 acquires nearby information showing conditions near the machine 350 (T2). Next, the brain function activation information detection unit 441A references the information stored in the brain function activation information database 431 and detects the brain function activation information from the nearby information (T3). In one example, the display of a red traffic light is detected as the brain function activation information at this point.

Meanwhile, at a predetermined timing, the imaging unit 415 captures face images including the facial surface of the subject 300 positioned in front of the output unit 420. The face images are captured at predetermined intervals (T4). The captured face images are sent to the facial change information acquisition unit 442.

Moreover, the facial change information acquisition unit 442 acquires the facial change information indicating time-series changes in the facial data of the subject 300 from the acquired facial data. Then, the facial change information decomposition unit 443 decomposes the facial change information into the plurality of components 1, 2, 3 . . . by singular value decomposition, principal component analysis, or independent component analysis (T5).

Next, the determination component extraction unit 444 calculates the correlation value between the brain function activation information and the plurality of components 1, 2, 3 . . . decomposed by the facial change information decomposition unit 443. Then, the determination component extraction unit 444 determines whether or not the correlation value is greater than or equal to the predetermined value (T6). When the correlation value is determined to be greater than or equal to the predetermined value, it is determined that there is correlation between the brain function activation information and that component (T6—Yes). Then, the determination component extraction unit 444 extracts, from among the components having correlation, a component for which the critical rate is low as the "reference determination component" (T7). Additionally, the determination component extraction unit 444 sets the correlation value between the reference determination component and the brain function activation information as the reference correlation value r1. Information of these reference determination components is stored in the storage unit 430 (T8). Meanwhile, when the correlation value between the brain function activation information and each of the components 1, 2, 3 . . . is less than the predetermined value, it is determined that there is no correlation therebetween, and that information is stored in the storage unit 430 (T6—No, T8).

Then, at a desired timing during driving of the machine 350, "determination mode" is selected and the subsequent driver state is determined (T9). First, the same processing as in steps T2 to T8 is executed, and the correlation value r between the determination component extracted from the facial change information and the brain function activation information is calculated (T10 to T15). The determination mode may be automatically or manually selected.

Then, the driver state determination unit 445 calculates the amount of change Δr, which is the amount of change between the reference correlation value r1 of the brain function activation information with respect to the reference determination component extracted in the reference setting mode and the correlation value r2 of the brain function activation information with respect to the determination component extracted in the determination mode (T16). Next, the driver state determination unit 450 determines whether or not the amount of change Δr of the correlation value r2 with respect to the reference correlation value r1 is within a predetermined range. Whether or not the amount of change Δr is within the predetermined range is determined on the basis of the determination information stored in the determination information database 432. When the amount of change Δr of the correlation value r2 with respect to the reference correlation value r1 is within a predetermined range, the driver state determination unit 445 determines that the driver state of the subject 300 driving the machine 350 is normal (T16—Yes, T17). When the amount of change Δr of the correlation value r2 with respect to the reference correlation value r1 is not within the predetermined range, the driver state determination unit 445 determines that the driver state of the subject 300 driving the machine 350 is not normal (T16—No, T18). In one example, the driver state determination unit 445 determines that the driver state is normal when the amount of change Δr is in the range Δra to Δrb described above, and that the driver state is not normal when the amount of change Δr exceeds Δrb. These determination results are output via the output unit 420 to a display device or the like (T19).

(6-2-3) Features of Driver State Determination Device 400A 6-2-3-1

As described above, the driver state determination device 400A according to the second embodiment includes the brain function activation information detection unit 441A, the facial change information acquisition unit 442, the facial change information decomposition unit 443, the determination component extraction unit 444, and the driver state determination unit 445. The brain function activation information detection unit 441A detects brain function activation information that activates human brain function from the brain function activation information provision object 600. The facial change information acquisition unit 422 acquires the facial change information indicating time-series changes in the facial data of the subject 300. The facial change information decomposition unit 433 decomposes the facial change information into the plurality of components 1, 2, 3 . . . by singular value decomposition, principal component analysis, or independent component analysis. The determination component extraction unit 444 extracts, from the plurality of components 1, 2, 3 . . . , a component related to the brain function activation information as the determination component. The driver state determination unit 445 determines the driver state of the subject 300 driving the machine 350 on the basis of the determination components.

Accordingly, with the driver state determination device 400A according to the second embodiment, the plurality of components are obtained by subjecting the facial change information to singular value decomposition, principal component analysis, or independent component analysis, and the determination component related to the detected brain function activation information is extracted from the plurality of components. As such, the presence/absence of brain activity of the subject 300 can be easily estimated without using electrodes or the like that require pretreatment before being applied. As a result, the driver state of the subject 300 driving the machine 350 can be easily determined on the basis of the determination component corresponding to the brain function of the subject 300.

6-2-3-2

A driver state determination method according to the second embodiment does not necessarily require the driver state determination device 400A. That is, regardless of whether or not the driver state determination device 400A is provided, it is sufficient that the driver state determination method according to the present embodiment include a brain function activation information detection step for detecting, at a predetermined timing, brain function activation information that activates human brain function from the brain function activation information provision object 600; then, a facial change information acquisition step for acquiring facial change information indicating time-series changes in the facial data of the subject 300; a facial change information decomposition step for decomposing the facial change information into a plurality of components by singular value decomposition, principal component analysis, or independent component analysis; a determination component extraction step for extracting a component related to the brain function activation information from the plurality of components as a determination component; and a driver state determination step for determining, on the basis of the determination component, a driver state of the subject 300 driving the machine 350.

According to this driver state determination method, the plurality of components is obtained by subjecting the facial change information to singular value decomposition, principal component analysis, or independent component analysis after the predetermined timing, and the determination component related to the brain function activation information is extracted from the plurality of components. As such, the driver state of the subject 300 driving the machine 350 can be easily determined.

6-2-3-3

In addition, the second embodiment provides features similar to those described for the first embodiment in (6-1-3).

(6-2-4) Modification Example of Driver State Determination Device 400A

Figure 32:
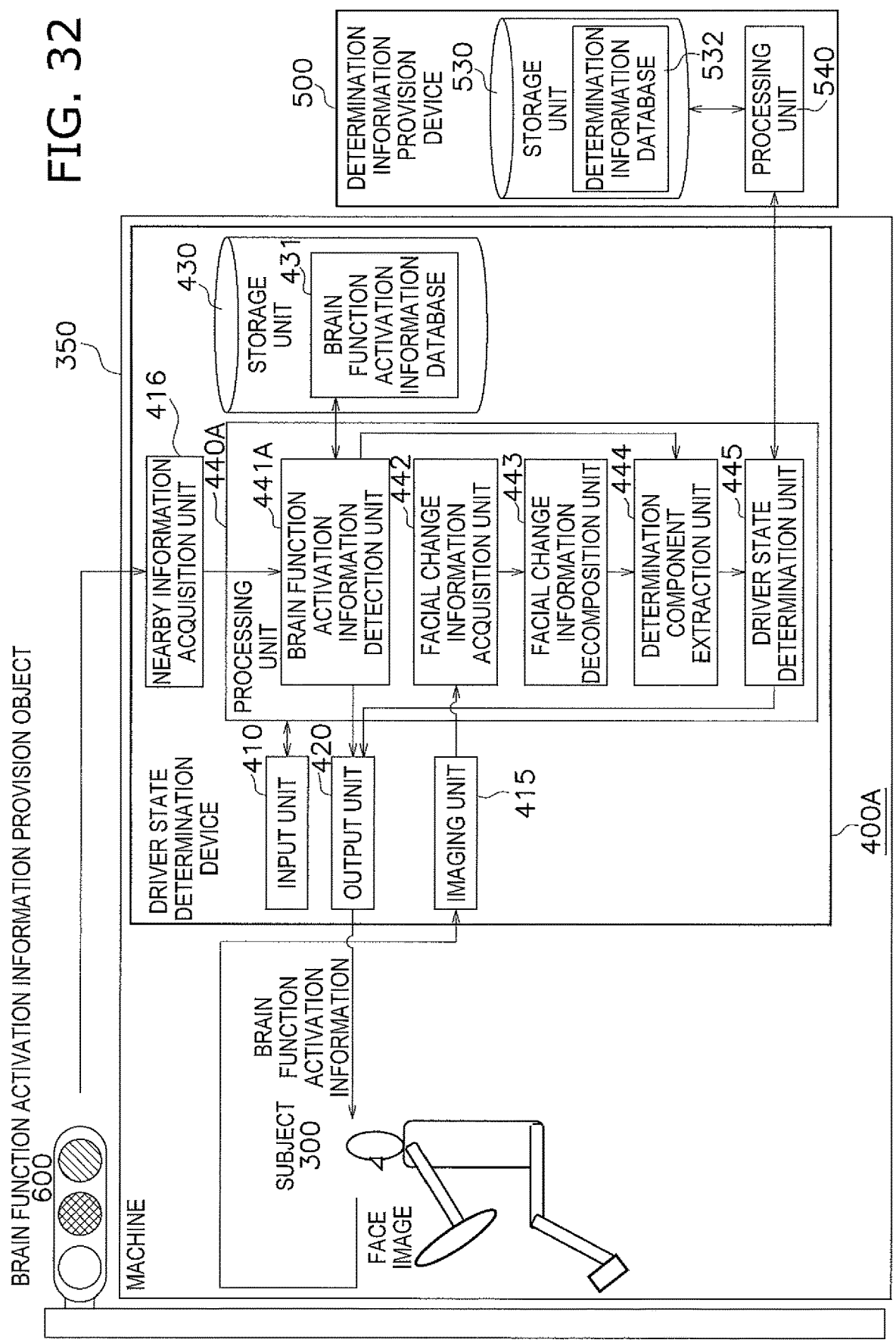
FIG. 32 is a schematic drawing illustrating a configuration of a modified example of the driver state determination device 400A according to the second embodiment.

As illustrated in FIG. 32, a configuration is possible in which the determination information provision device 500 or the like provided on a network is used in the driver state determination device 400A according to the second embodiment.

In the present modification example, the driver state determination device 400A issues requests to the determination information provision device 500 described above for the provision of the determination information. Specifically, in the present modification example, the determination information database 532 is stored in the determination information provision device 500, which is on the network, and the driver state determination unit 445 accesses the determination information provision device 500 when the driver state level is determined. Moreover, the driver state determination unit 445 determines the driver state level of the subject 300 on the basis of the calculated correlation value r2 and the determination information.

Figure 33:
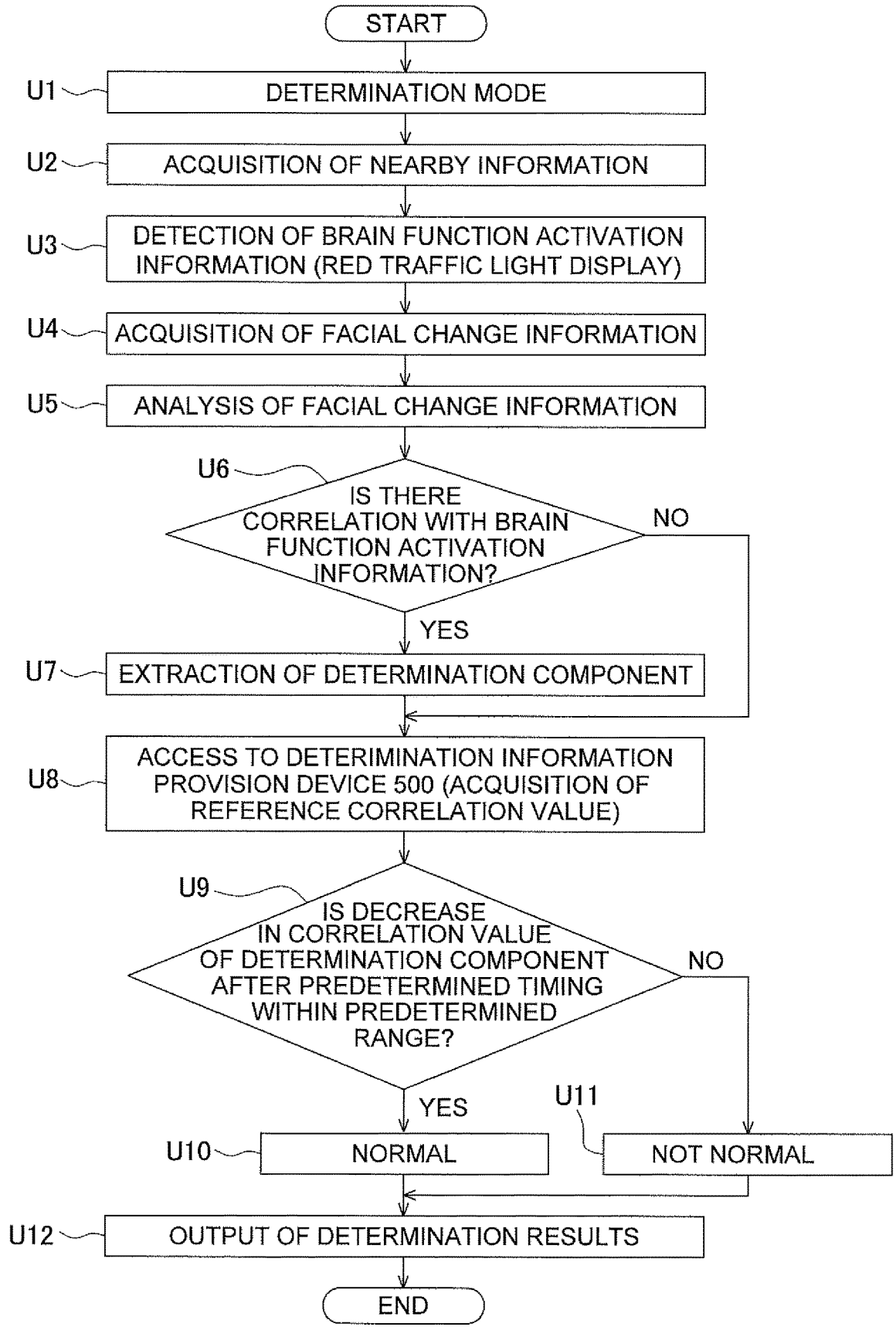
FIG. 33 is a flowchart showing operations of the modified example of the driver state determination device 400A according to the second embodiment.

Accordingly, with the driver state determination device 400A of the present modification example, the driver state determination unit 445 can use an external network to determine the driver state level of the subject 300. Additionally, the driver state determination unit 445 determines the driver state using the reference determination component stored in the determination information provision device 500, which is on the external network. As such, it is possible to streamline reference setting work. That is, as illustrated in FIG. 33, a configuration is possible in which the reference setting mode described above is omitted and only the determination mode is executed. In this case, the processing described above for steps T9 to T19 is performed in steps U1 to U7 and U9 to U12. Additionally, in step U8, the driver state determination device 400A issues a send request to the determination information provision device 500 for the determination information. Note that the steps described above may be executed in part without using the driver state determination device 400A.

Additionally, with the method of the present modification example, the driver state can be determined using big data. That is, the reference correlation value r1 and the predetermined amount of change Δr are obtained from big data. Specifically, the brain function activation information is provided to a person other than the subject to acquire a reference determination component, and a reference correlation value r1 that is calculated on the basis of this reference determination component is used. As a result, the determination information can be optimized in a timely manner.

(6-3) Third Embodiment

(6-3-1) Configuration of Driver State Determination Device 400B

In the following, constituents identical to those described previously are assigned the same reference signs and redundant description thereof is foregone. To distinguish from the other embodiments, constituents that differ in the present embodiment are marked with the letter "B."

Figure 34:
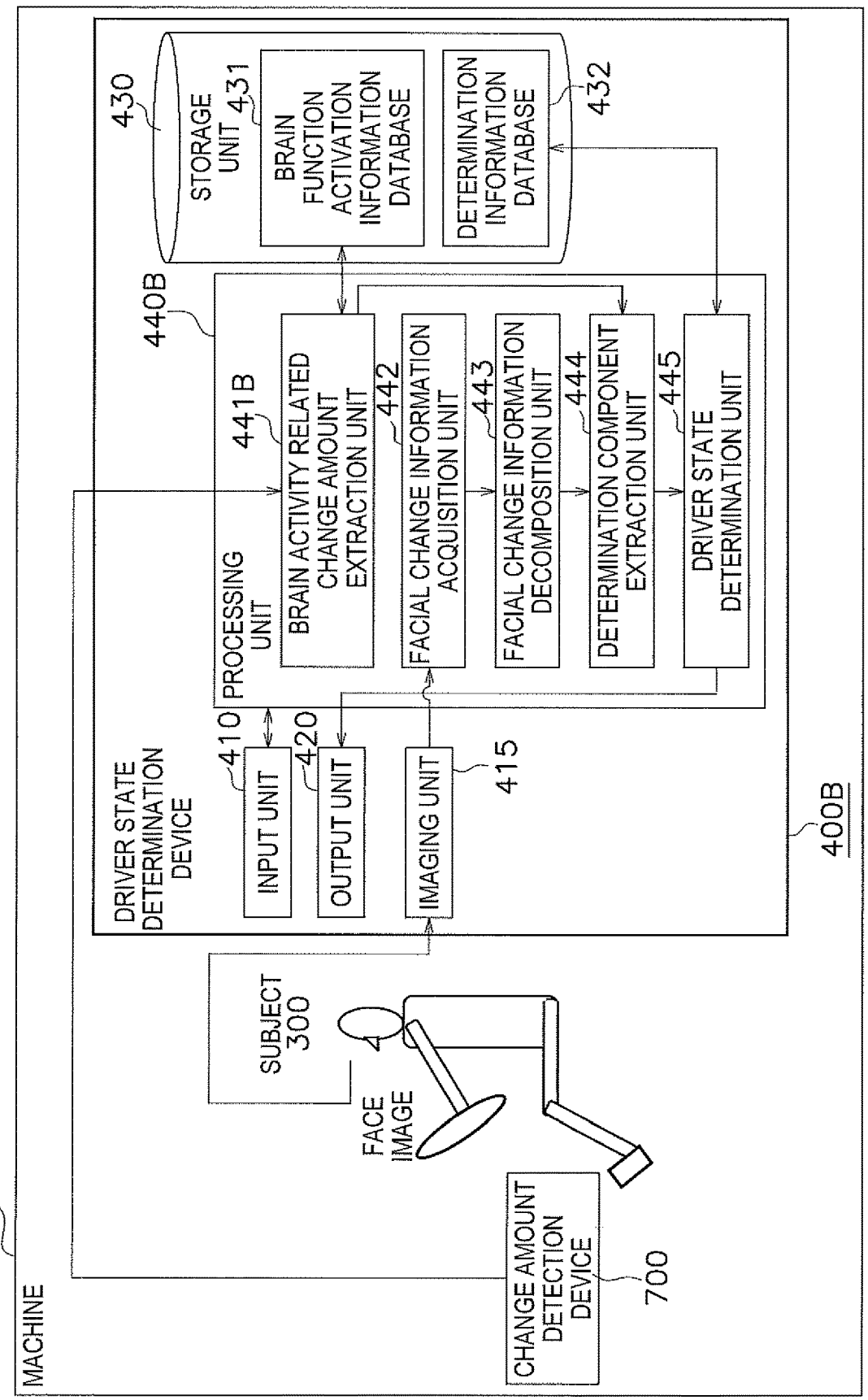
FIG. 34 is a schematic drawing illustrating a configuration of a driver state determination device 400B according to a third embodiment.

FIG. 34 is a schematic drawing illustrating an example of a driver state determination device 400B according to a third embodiment. The third embodiment differs from the first embodiment in that brain function is considered to be activated when a predetermined operation on the machine 350 occurs. Examples of the predetermined operation include steering wheel operation and brake pedal depressing of an automobile.

The driver state determination device 400B is provided with the input unit 410, the imaging unit 415, the output unit 420, the storage unit 430, and the processing unit 440B. The driver state determination device 400B determines the driver state of the subject 300 driving the machine 350. Here, the term "machine" refers to an automatic machine such as an automobile, a railway vehicle, an aircraft, nuclear power generation equipment, and various types of plants.

In the third embodiment, the machine 350 includes a change amount detection device 700. The change amount detection device 700 detects a predetermined amount of change caused by the predetermined operation on the machine 350. In one example, when the machine 350 is an automobile, an acceleration change amount is used as the predetermined amount of change. The detected amount of change is sent to a brain activity related change amount extraction unit 441B.

The processing unit 440B is configured to execute information processing in the driver state determination device 400B. Specifically, the processing unit 440B is configured from a CPU, cache memory, and the like. The processing unit 440B executes the programs incorporated into the storage unit 430 to function as the brain activity related change amount extraction unit 441B, the facial change information acquisition unit 442, the facial change information decomposition unit 443, the determination component extraction unit 444, and the driver state determination unit 445.

The brain activity related change amount extraction unit 441B is configured to extract, as a brain activity related change amount, an amount of change related to human brain activity from the predetermined amount of change caused by the predetermined operation on the machine 350. Specifically, the brain activity related change amount extraction unit 441B extracts the brain activity related change amount from information sent from a change amount detection unit 75. In one example, when the acceleration change amount is used as the predetermined amount of change, the brain activity related change amount extraction unit 441B extracts, as the brain activity related change amount, acceleration change amounts greater than or equal to a predetermined value and acceleration change amounts that meet a predetermined condition from the measured acceleration change amounts. When the brain activity related change amount extraction unit 441B extracts the brain activity related change amount, the determination component extraction unit 444 calculates the correlation value r between the extracted brain activity related change amount and the determination component.

(6-3-2) Operations of Driver State Determination Device 400B

Figure 35A:
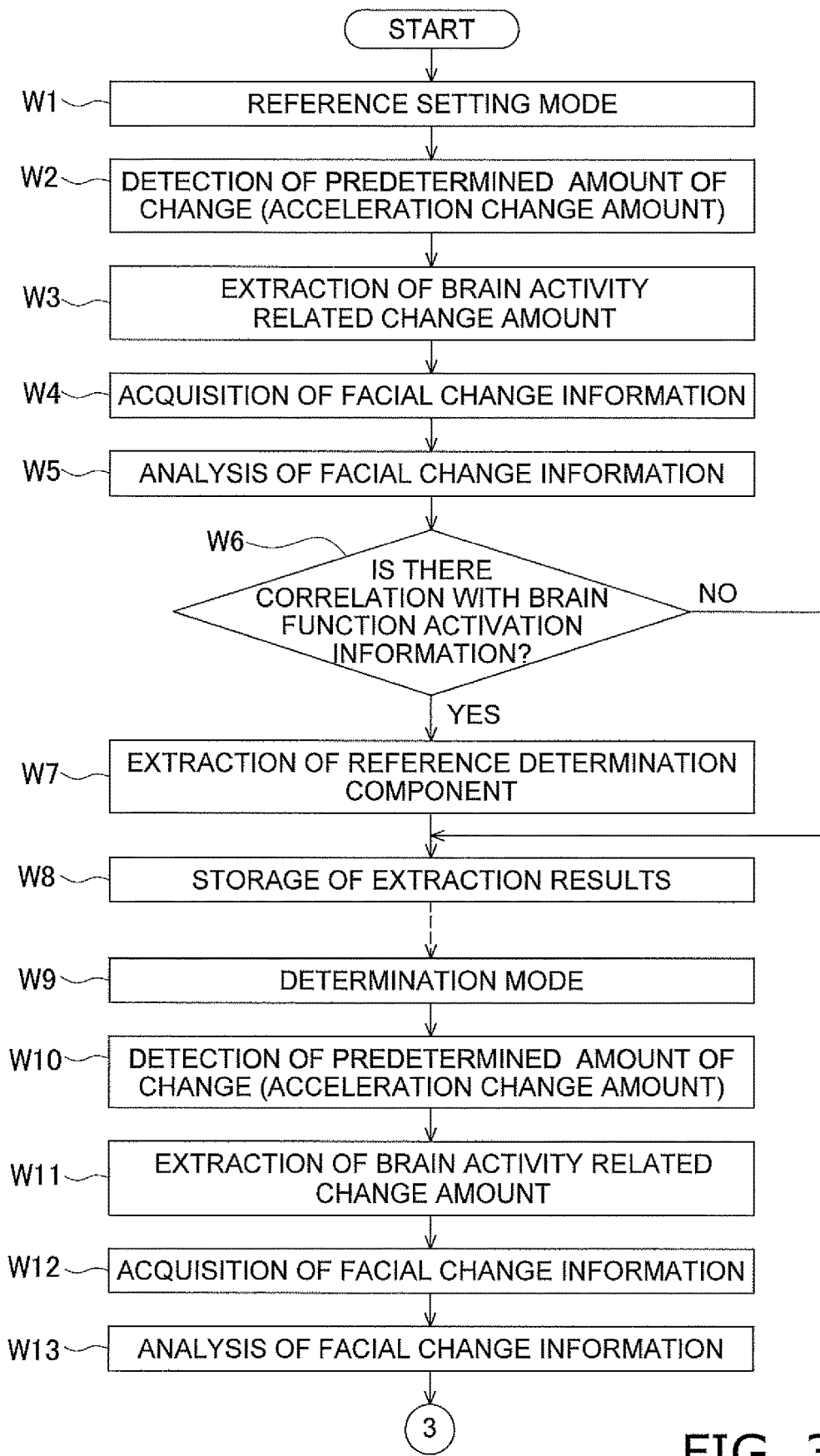
FIG. 35A is a flowchart showing operations of the driver state determination device 400B according to the third embodiment.
Figure 35B:
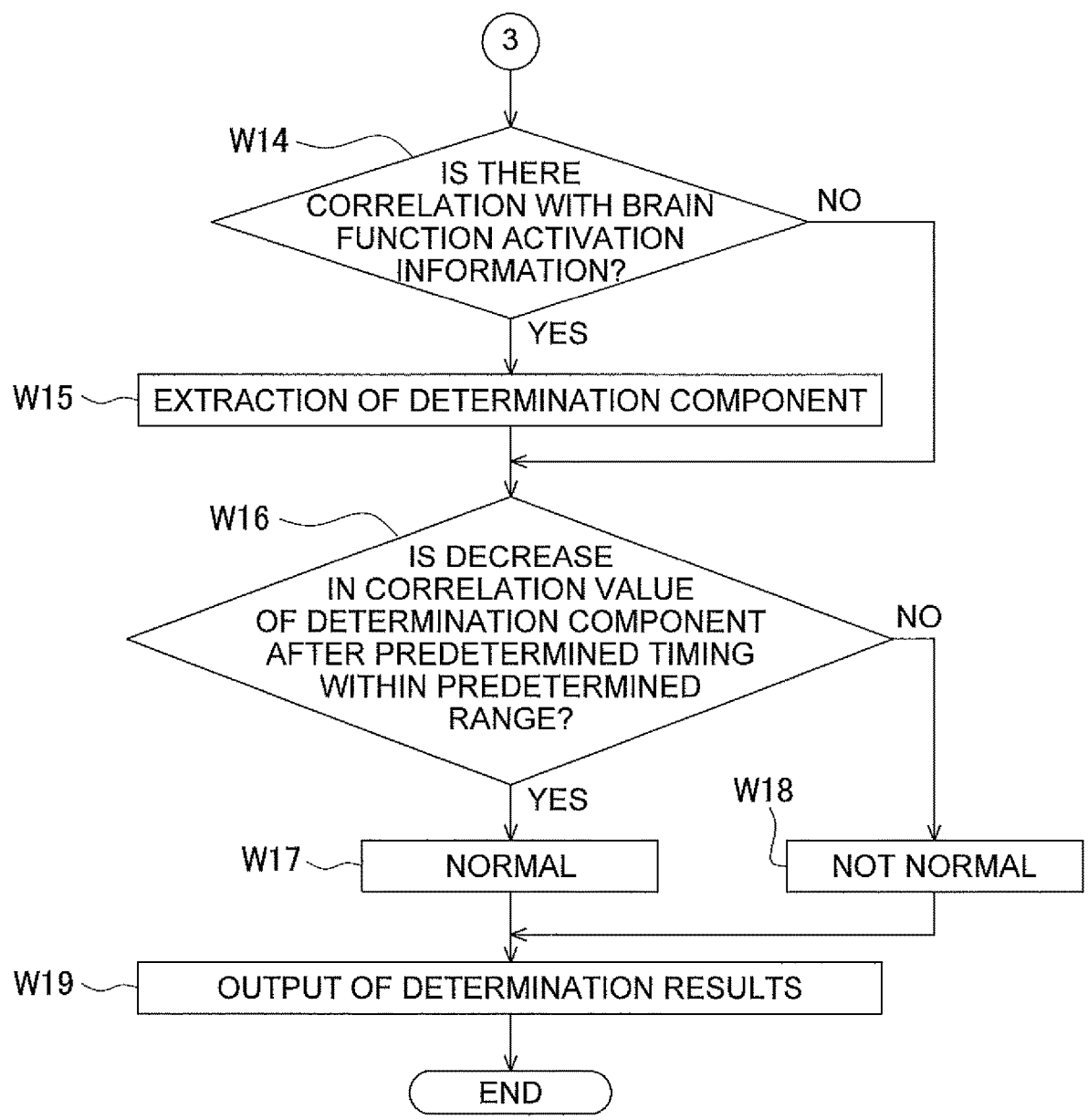
FIG. 35B is a flowchart showing operations of the driver state determination device 400B according to the third embodiment.

FIG. 35 is a flowchart showing operations of the driver state determination device 400B according to the second embodiment.

First, at a predetermined timing during driving of the machine 350, "reference setting mode" is selected and the reference determination component is extracted (W1). Specifically, the change amount detection device 700 detects the predetermined amount of change caused by the predetermined operation on the machine 350 (W2). In one example, the acceleration change amount of a transportation machine is detected. Next, the brain activity related change amount extraction unit 441B compares the detected predetermined amount of change with the information in the brain function activation information database 431, and extracts the brain activity related change amount from the information of the predetermined amount of change (W3).

Meanwhile, at a predetermined timing, the imaging unit 415 captures face images including the facial surface of the subject 300 positioned in front of the output unit 420. The face images are captured at predetermined intervals (W4). The captured face images are sent to the facial change information acquisition unit 442.

Moreover, the facial change information acquisition unit 442 acquires facial change information indicating time-series changes in the facial data of the subject 300 from acquired facial data. Then, the facial change information decomposition unit 443 decomposes the facial change information into the plurality of components by singular value decomposition, principal component analysis, or independent component analysis (W5).

Next, the determination component extraction unit 444 calculates the correlation value between the brain activity related change amount and the plurality of components 1, 2, 3 . . . decomposed by the facial change information decomposition unit 443. Then, the determination component extraction unit 444 determines whether or not the correlation value is greater than or equal to the predetermined value (W6). When the correlation value is determined to be greater than or equal to the predetermined value, it is determined that there is correlation between the brain activity related change amount and that component (W6—Yes). Then, the determination component extraction unit 444 extracts, from among the components having correlation, a component for which the critical rate is low as the "reference determination component" (W7). Additionally, the determination component extraction unit 444 sets the correlation value between the reference determination component and the brain activity related change amount as the reference correlation value r 1. Information of these reference determination components is stored in the storage unit 430 (W8). Meanwhile, when the correlation value between the brain activity related change amount and each of the components 1, 2, 3 . . . is less than the predetermined value, it is determined that there is no correlation therebetween, and that information is stored in the storage unit 430 (W6—No, W8).

Then, at a desired timing during driving of the machine 350, "determination mode" is selected and the subsequent driver state is determined (W9). First, the same processing as in steps W2 to W7 is executed, and the correlation value r2 between the determination component extracted from the facial change information and the brain activity related change amount is calculated (W10 to W15). The determination mode may be automatically or manually selected.

Then, the driver state determination unit 445 calculates the amount of change Δr, which is the difference between the reference correlation value r1 of the brain activity related change amount with respect to the reference determination component extracted in the reference setting mode and the correlation value r2 of the brain activity related change amount with respect to the determination component extracted in the determination mode (W16). Next, the driver state determination unit 450 determines whether or not the amount of change Δr of the correlation value r2 with respect to the reference correlation value r1 is within a predetermined range. Whether or not the amount of change Δr is within the predetermined range is determined on the basis of the determination information stored in the determination information database 432. When the amount of change Δr of the correlation value r2 with respect to the reference correlation value r1 is within a predetermined range, the driver state determination unit 445 determines that the driver state of the subject 300 driving the machine 350 is normal (W16—Yes, W17). When the amount of change Δr of the correlation value r2 with respect to the reference correlation value r1 is not within the predetermined range, the driver state determination unit 445 determines that the driver state of the subject 300 driving the machine 350 is not normal (W16—No, W18). In one example, it is determined that the driver state is normal when the amount of change Δr is in the range Δra to Δrb described above, and that the driver state is not normal when the amount of change Δr exceeds Δrb. These determination results are output via the output unit 420 to a display device or the like (W19).

(6-3-3) Features of Driver State Determination Device 400B

6-3-3-1

As described above, the driver state determination device 400B according to the third embodiment includes the brain activity related change amount extraction unit 441B, the facial change information acquisition unit 442, the facial change information decomposition unit 443, the determination component extraction unit 444, and the driver state determination unit 445. The brain activity related change amount extraction unit 441B acquires, from the change amount detection device 700, the predetermined amount of change caused by the predetermined operation on the machine 350. Then, the brain activity related change amount extraction unit 441B extracts, as the brain activity related change amount, the amount of change related to human brain activity from the acquired amounts of change. The facial change information acquisition unit 442 acquires the facial change information indicating time-series changes in the facial data of the subject 300. The facial change information decomposition unit 443 decomposes the facial change information into the plurality of components 1, 2, 3 . . . by singular value decomposition, principal component analysis, or independent component analysis. The determination component extraction unit 444 extracts, from the plurality of components 1, 2, 3 . . . , a component related to the brain activity related change amount as the determination component. The driver state determination unit 445 determines the driver state of the subject 300 driving the machine 350 on the basis of the determination component.

Accordingly, with the driver state determination device 400B according to the third embodiment, the plurality of components are obtained by subjecting the facial change information to singular value decomposition, principal component analysis, or independent component analysis, and the determination component related to the brain activity related change amount is extracted from the plurality of components. As such, the presence/absence of brain activity of the subject 300 can be estimated without using electrodes or the like that require pretreatment before being applied. As a result, the driver state of the subject 300 driving the machine 350 can be easily determined on the basis of the components corresponding to the brain function of the subject 300.

6-3-3-2

A driver state determination method according to the third embodiment does not necessarily require the driver state determination device 400B. That is, regardless of whether or not the driver state determination device 400B is provided, it is sufficient that the driver state determination method according to the present embodiment include, at a predetermined timing, a machine change amount detection step for detecting the predetermined amount of change caused by the predetermined operation on the machine 350; a brain function activation information extraction step for extracting, as the brain activity related change amount, the amount of change related to the brain activity of the subject 300 operating the machine 350; the facial change information acquisition step for acquiring facial change information indicating time-series changes in the facial data of the subject 300; the facial change information decomposition step for decomposing the facial change information into the plurality of components 1, 2, 3 . . . by singular value decomposition, principal component analysis, or independent component analysis; the determination component extraction step for extracting a component related to the brain activity related change amount from the plurality of components 1, 2, 3 . . . as the determination component; and the driver state determination step for determining, on the basis of the determination component, the driver state of the subject 300 driving the machine 350.

According to this driver state determination method, the plurality of components is obtained by subjecting the facial change information to singular value decomposition, principal component analysis, or independent component analysis after the predetermined timing, and a determination component related to the brain activity related change amount is extracted from the plurality of components. As such, the driver state of the subject 300 driving the machine 350 can be easily determined.

6-3-3-3

In addition, the third embodiment provides features similar to those described for the first embodiment in (6-1-3).

(6-3-4) Modification Example of Driver State Determination Device 400B

Figure 36:
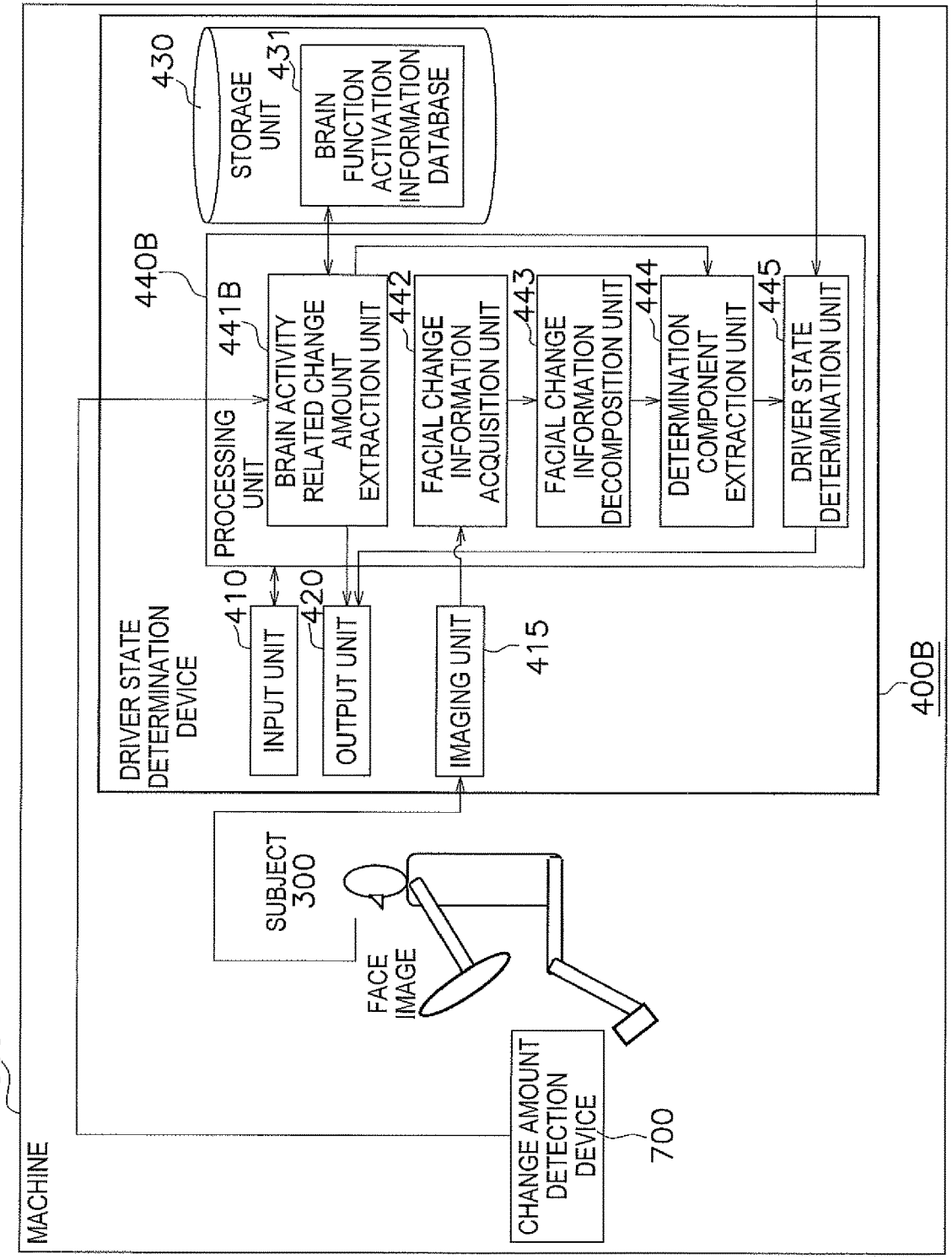
FIG. 36 is a schematic drawing illustrating a configuration of a modified example of the driver state determination device 400B according to the third embodiment.

As illustrated in FIG. 36, a configuration is possible in which the determination information provision device 500 or the like provided on a network is used in the driver state determination device 400B according to the third embodiment.

In the present modification example, the driver state determination device 400B issues requests to the determination information provision device 500 described above for the provision of the determination information. Specifically, in the present modification example, the determination information database 532 is stored in the determination information provision device 500, which is on the network, and the driver state determination unit 445 accesses the determination information provision device 500 when the driver state level is determined. Moreover, the driver state determination unit 445 determines the driver state level of the subject 300 driving the machine 350 on the basis of the calculated correlation value r2 and the determination information.

Figure 37:
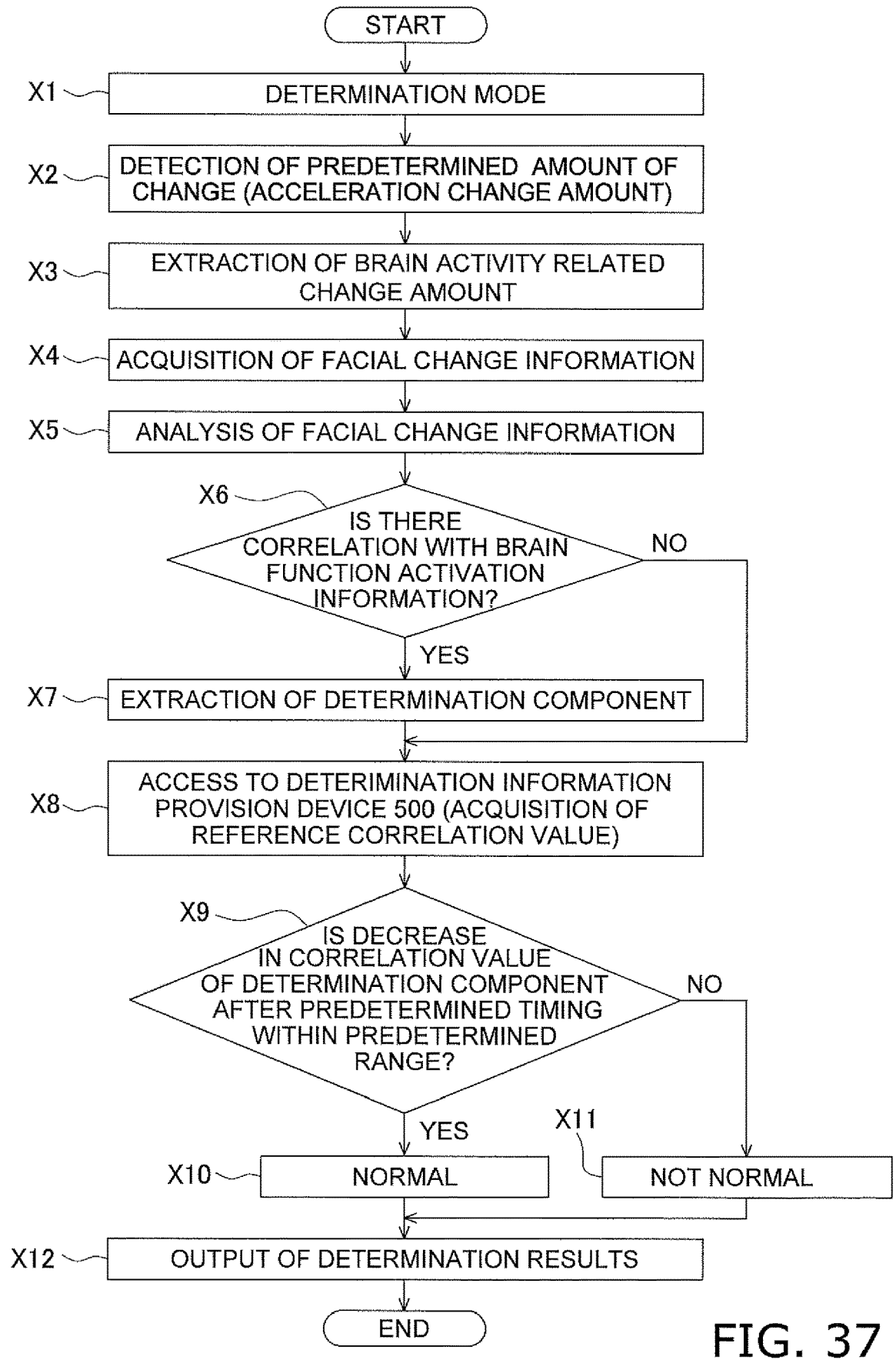
FIG. 37 is a flowchart showing operations of the modified example of the driver state determination device 400B according to the third embodiment.

Accordingly, with the driver state determination device 400B of the present modification example, the driver state determination unit 445 can use an external network to determine the driver state level of the subject 300. Additionally, the driver state determination unit 445 determines the driver state level using the reference determination component stored in the determination information provision device 500, which is on the external network. As such, it is possible to streamline reference setting work. That is, as illustrated in FIG. 37, a configuration is possible in which the reference setting mode described above is omitted and only the determination mode is executed. In this case, the processing described above for steps W9 to W19 is performed in steps X1 to X7 and X9 to X12. Additionally, in step X8, the driver state determination device 400B issues a send request to the determination information provision device 500 for the determination information. Note that the steps described above may be executed in part without using the driver state determination device 400B.

Additionally, with the method of the present modification example, the driver state can be determined using big data. That is, the reference correlation value r1 and the predetermined amount of change Δr are obtained from big data. Specifically, the reference determination component is acquired from the brain activity related change amount during normal driving, and a reference correlation value r1 that is calculated on the basis of this reference determination component is used. As a result, the determination information can be optimized at all times.

(6-3-5) Verification of Driver State Determination Method 6-3-5-1

Figure 38:
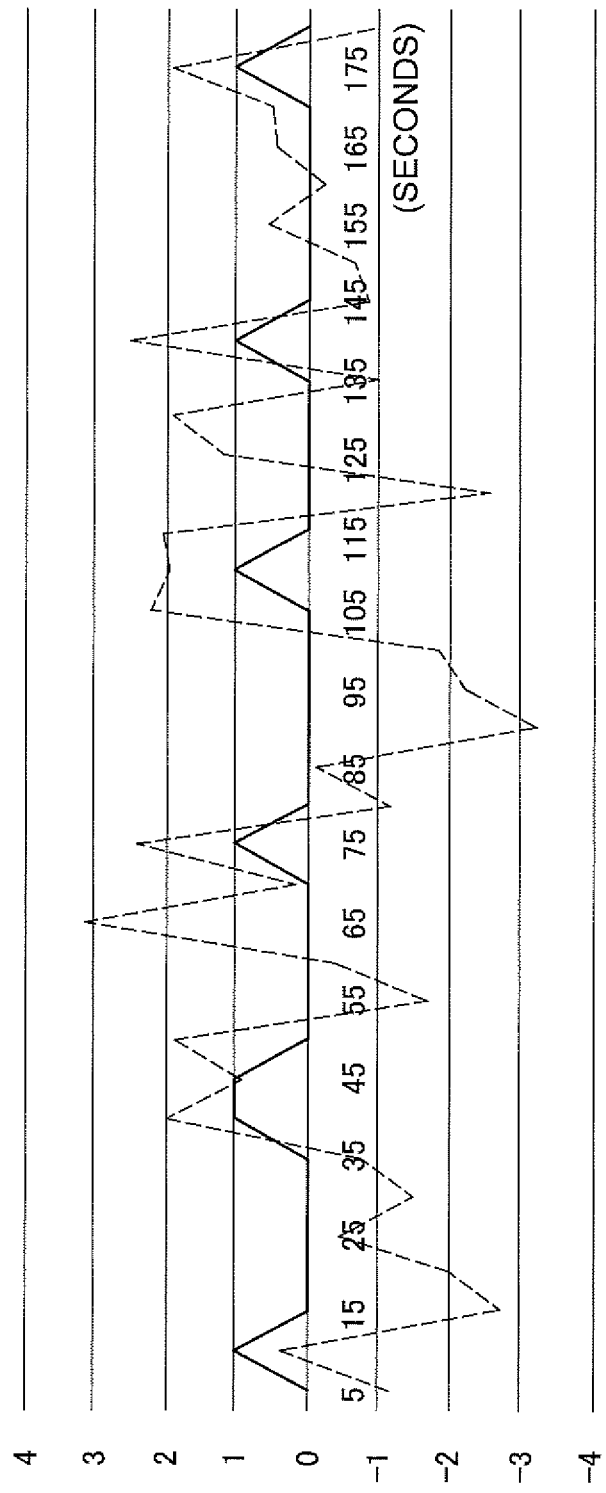
FIG. 38 is a chart illustrating verification results of a driver state determination method according to the third embodiment.

FIG. 38 illustrates changes of the determination component when the machine 350 is an automobile and the predetermined operation is emergency braking. The solid line represents changes in emergency braking, and the dashed line represents changes of the determination component. Note that the determination component is calculated from the erythema index. As illustrated in FIG. 38, correlation was identified between the emergency braking and the determination component. Accordingly, it was confirmed that the driver state can be determined on the basis of the amount of change of braking.

6-3-5-2

Figure 39:
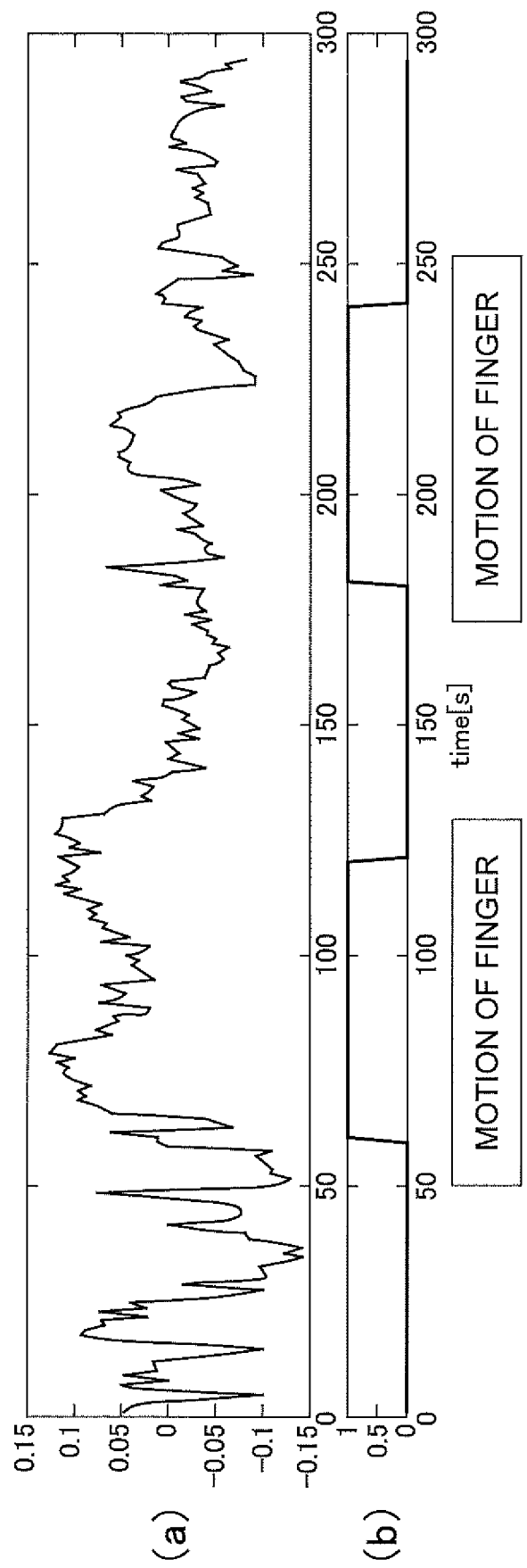
FIG. 39 is a chart illustrating verification results of the driver state determination method according to the third embodiment.

FIG. 39 illustrates changes of the determination component when the machine 350 is an automobile and the predetermined operation is finger tapping. Section (b) illustrates a state in which tapping actions are being performed, and section (a) illustrates changes of the determination component. In this case, the tapping action was defined as using the thumb of the right hand to sequentially touch each finger, from the little finger to the index finger. The determination component is calculated from the erythema index. As illustrated in FIG. 39, correlation was identified between the finger tapping and the determination component. Accordingly, it was confirmed that the driver state can be determined on the basis of the amount of change of finger tapping.

(6-4) Fourth Embodiment

A driver state determination device according to a fourth embodiment is a combination of the driver state determination devices according to the first to the third embodiments. As a result of this configuration, the driver states for various types of automatic machines can be determined, as illustrated in FIG. 40.

When, for example, the subject 300 is the driver of an automobile, signals indicating the start and end of driving, amounts of operation of the steering wheel or brakes, travel distance, information outside the vehicle, traffic light information, information of the oncoming vehicle, pedestrian information, and the like can be used as the brain function activation information or the predetermined operation to determine the driver state. When the subject 300 is the operator of an automatic machine such as a nuclear power plant, signals of the automatic machine corresponding to the starting, stopping, no abnormality, and other states of operation can be used as the brain function activation information to determine the driver state. When the subject 300 is the driver of a train, signals installed on the side of the track, railway signs, stopping position targets, and the like can be used as the brain function activation information to determine the driver state. When the subject 300 is the pilot of an aircraft, signals from instruments, commands from control towers, and the like can be used as the brain function activation information to determine the driver state.

Furthermore, the brain activity of a person intending to carry out an act of terror is in an excited state, and tends to exhibit strong responses to information about damage intended to be inflicted. For example, such a person will exhibit high response to information about the number of passengers, the location where the act of terrorism is to be carried out, and so on. As such, information about the damage intended to be inflicted can be used as the brain function activation information to determine whether or not the subject 300 intends to carry out an act of terror.

INDUSTRIAL APPLICABILITY

The present invention can easily estimate brain activity and, as such, is useful for applications to brain activity visualization devices that visualize the physiological state of subjects on the basis of brain activity.

What is claimed is:

1. A driver state determination device, comprising:
   a camera acquiring facial change information indicating a time-series change in facial data of one selected from the group consisting of
     a subject driving a machine at a time when brain function activation information that activates human brain function is provided to the subject or surroundings of the subject,
     a subject driving a machine at a time when the brain function activation information provided to the subject driving the machine is detected, and
     a subject performing a predetermined operation on a machine; and
   a CPU determining the driver state of the subject based on the facial change information.

2. The driver state determination device according to claim 1, wherein
   the CPU decomposes the facial change information into a plurality of components corresponding to at least a plurality of time distributions,
   the CPU determines the driver state of the subject based on a determination component extracted from the plurality of components.

3. The driver state determination device according to claim 2, wherein
   the CPU decomposes the facial change information into a plurality of components corresponding to time distributions and space distributions.

4. The driver state determination device according to claim 2, wherein
   the CPU decomposes the facial change information into a plurality of components by singular value decomposition, principal component analysis, or independent component analysis.

5. The driver state determination device according to claim 2, wherein
   the CPU extracts, as a determination component, a component related to the brain function activation information that activates human brain activity or a brain activity related change amount from the plurality of components,
   the brain activity related change amount being extracted from a predetermined amount of change caused by a predetermined operation on the machine.

6. The driver state determination device according to claim 5, wherein
   the CPU extracts the determination component based on a value of a critical rate.

7. The driver state determination device according to claim 5, further comprising:
   a memory associating, with a driver state level, an amount of change of a predetermined range, of a correlation value of a determination component calculated for the brain function activation information or a brain activity related change amount, from a reference correlation value of a reference determination component calculated for the brain function activation information or the brain activity related change amount,
   the memory storing the amount of change as determination information,
   the CPU calculating the correlation value of the determination component to the brain function activation information or the brain activity related change amount, and
   the CPU determining the driver state level of the subject based on the calculated correlation value and the determination information.

8. The driver state determination device according to claim 5, further comprising:
   a determination information provision device on a network including a determination information storage unit that stores an amount of change associated with a driver state level of a predetermined range as determination information,
   the amount of change being defined as an amount of change, of a correlation value of a determination component calculated for the brain function activation information or a brain activity related change amount, from a reference correlation value of a reference determination component calculated for the brain function activation information or the brain activity related change amount,
   the CPU calculating the correlation value of the determination component to the brain function activation information or the brain activity related change amount, and
   the CPU determining the driver state level of the subject based on the calculated correlation value and the determination information.

9. The driver state determination device according to claim 1, wherein
the machine is an automatic machine including at least one selected from the group consisting of an automobile, a railway vehicle, an aircraft, a nuclear power generation equipment, and a plant machine.

10. The driver state determination device according to claim 1,
the CPU provides the brain function activation information to the subject driving the machine.

11. The driver state determination device according to claim 1, wherein
the CPU detects the brain function activation information provided to the subject driving the machine.

12. The driver state determination device according to claim 1, wherein
the CPU extracts, as a brain activity related change amount, an amount of change related to human brain activity from a predetermined amount of change caused by the predetermined operation on the machine.

13. The driver state determination device according to claim 12, wherein
the machine is an automatic machine including at least one selected from the group consisting of an automobile, a railway vehicle, an aircraft, a nuclear power generation equipment, and a plant machine, and
the CPU extracts the brain activity related change amount from an amount of change in a command signal to the automatic machine.

14. The driver state determination device according to claim 12, wherein
the machine is a transportation machine including at least one selected from the group consisting of an automobile, a railway vehicle, and an aircraft, and
the CPU extracts the brain activity related change amount from an amount of change in an acceleration of the transportation machine.

15. The driver state determination device according to claim 1, wherein
the CPU further
estimates brain activity of the subject based on the facial change information, and
monitors a physiological state of the subject based on the brain activity of the subject estimated.

16. The driver state determination device according to claim 15, wherein
the CPU, in order to estimate brain activity,
decomposes the facial change information into a plurality of components by singular value decomposition, principal component analysis, or independent component analysis, and
estimates the brain activity of the subject based on the plurality of components.

17. The driver state determination device according to claim 15, wherein
the the CPU, in order to monitor the physiological state of the subject, analyzes a consciousness level of the subject with respect to an operation based on the brain activity of the subject.

18. The driver state determination device according to claim 17, wherein
the CPU further gives notice to the subject to pay attention when the consciousness level analyzed by the CPU declines to less than or equal to a certain level.

19. The driver state determination device according to claim 15, further comprising:
a display enabling an administrator managing the machine operated by the subject to acquire information related to the physiological state of the subject.

20. A driver state determination method comprising:
a step selected from the group consisting of:
a brain function activation information provision step providing brain function activation information, which activates human brain activity, to a subject driving a machine,
a brain function activity activation information detection step detecting brain function activation information, which activates human brain activity, provided to the subject driving the machine, and
a machine change amount detection step detecting a predetermined amount of change caused by a predetermined operation on the machine and a brain activity related change amount extraction step extracting, as a brain activity related change amount, an amount of change related to brain activity of the subject driving the machine from the amount of change detected in the machine change amount detecting step;
a facial change information acquisition step acquiring facial change information indicating a time-series change in facial data of the subject;
a facial change information decomposition step decomposing the facial change information into a plurality of components by singular value decomposition, principal component analysis, or independent component analysis;
a determination component extraction step extracting, from the plurality of components, a component related to the brain function activation information or the brain activity related change amount as a determination component; and
a driver state determination step determining a driver state of the subject based on the determination component.

21. The driver state determination method according to claim 20, wherein
an amount of change of a predetermined range is associated with a driver state level and stored in a determination information storage unit as determination information,
the amount of change is defined as an amount of change, of a correlation value of a determination component calculated for the brain function activation information or the brain activity related change amount, from a reference correlation value of a reference determination component calculated for the brain function activation information or the brain activity related change amount, and
in the driver state determination step, a correlation value of the determination component to the brain function activation information or the brain activity related change amount is calculated, and the driver state level of the subject is determined based on the calculated correlation value and the determination information.

22. The driver state determination method according to claim 21, wherein
the brain function activation information detection step, the brain function activation information provision step, or the machine change amount detection step and the brain activity related change amount extraction step,
the facial change information acquisition step,
the facial change information decomposition step, and
the determination component extraction step are executed at a predetermined timing, and
a component related to the brain function activation information or the brain activity related change amount is extracted as a reference determination component.

23. The driver state determination method according to claim 21, wherein
the determination information storage unit is stored in a determination information provision device on a network, and
in the driver state determination step, the determination information provision device is accessed when the driver state level is determined.

24. The driver state determination method according to claim 23, wherein
the reference correlation value is calculated based on a reference determination component, and the reference determination component is obtained by providing the brain function activation information to a person other than the subject, or
the reference correlation value is calculated based on a brain activity related change amount during normal operation.

* * * * *